United States Patent
Lindsley et al.

(10) Patent No.: US 9,505,729 B2
(45) Date of Patent: Nov. 29, 2016

(54) ISOXAZOLE ANALOGS AS MEDIATORS OF TRANSCRIPTIONAL INDUCTION OF E-CADHERIN

(71) Applicant: Vanderbilt University, Nashville, TN (US)

(72) Inventors: Craig W. Lindsley, Brentwood, TN (US); Alex G. Waterson, Murfreesboro, TN (US); R. Daniel Beauchamp, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 14/828,286

(22) Filed: Aug. 17, 2015

(65) Prior Publication Data
US 2016/0052896 A1    Feb. 25, 2016

Related U.S. Application Data
(60) Provisional application No. 62/040,984, filed on Aug. 22, 2014.

(51) Int. Cl.
| | | |
|---|---|---|
| C07D 261/18 | (2006.01) | |
| C07D 413/14 | (2006.01) | |
| A61K 31/42 | (2006.01) | |
| C07D 413/12 | (2006.01) | |
| C07D 403/12 | (2006.01) | |
| C07D 471/04 | (2006.01) | |
| C07D 231/14 | (2006.01) | |
| C07D 401/12 | (2006.01) | |

(52) U.S. Cl.
CPC .......... *C07D 261/18* (2013.01); *C07D 231/14* (2013.01); *C07D 401/12* (2013.01); *C07D 403/12* (2013.01); *C07D 413/12* (2013.01); *C07D 413/14* (2013.01); *C07D 471/04* (2013.01)

(58) Field of Classification Search
None
See application file for complete search history.

(56) References Cited

FOREIGN PATENT DOCUMENTS

WO    WO 2007/078113 A1  *  7/2007

OTHER PUBLICATIONS

Project 2 of GI Cancer SPORE grant No. P50CA095103. (Aug. 17, 2015).
Al-Greene, N. T., et al. (2013) Four jointed box 1 promotes angiogenesis and is associated with poor patient survival in colorectal carcinoma. *PLoS One* 8: 369660.
An, H., et al. (2015) Small molecule/ML327 mediated transcriptional de-repression of E-cadherin and inhibition of epithelial-to-mesenchymal transition. *Oncotarget.* 6(26): 22934-22948.
Diehl, J. A., et al. (1998) Glycogen synthase kinase-3beta regulates cyclin D1 poteolysis and subcellular localization. *Genes & Development* 12: 3499-3511.
Freeman, T. J. et al. (2012) Smad4-Mediated Signaling Inhibits Intestinal Neoplasia by Inhibiting Expression of β-Catenin. *Gastroenterology* 142: 562-572.
GI Cancer SPORE grant No. P50CA095103. (Abstract) (Aug. 17, 2015).
Grant No. U54MH084659 awarded by the National Institute of Health (NIH). (Aug. 17, 2015).
Gupta, G. P. and Massague, J. (2006) Cancer metastasis: building a framework. *Cell* 127: 679-695.
Heldin, C. H., et al. (2012) Regulation of EMT by TGFβ in cancer. *FEBS Lett.* 586: 1959-1970.
Iwatsuki, M., et al. (2010) Epithelial-mesenchymal transition in cancer development and its clinical significance. *Cancer Sci.* 101: 293-299.
Jemal, A., et al. (2007). Cancer statistics, 2007. *CA: A Cancer Journal for Clinicians* 57: 43-66.
Kain, K. H., et al. (2014) The chick embryo as an expanding experimental model for cancer and cardiovascular research. *Dev. Dyn.* 243(2): 216-228.
Kakihana, M., et al. (2009) Induction of E-cadherin in lung cancer and interaction with growth suppression by histone deacetylase inhibition. *Journal of Thoracic Oncology* 4: 1455-1465.
Katsuno, Y., et al. (2013) TGF-β signaling and epithelial-mesenchymal transition in cancer progression. *Current Opinion in Oncology* 25: 76-84.
Lim, J., et al. (2012) Epithelial-mesenchymal transitions: insights from development. *Development* 139: 3471-3486.
Liu, Y.N. et al. (2005) Regulatory mechanisms controlling human E-cadherin gene expression. *Oncogene* 24: 8277-8290.
Miettinen, P. J., et al. (1994) TGF-beta induced transdifferentiation of mammary epithelial cells to mesenchymal cells: involvement of type I receptors. *J. Cell Biol.* 127: 2021-2036.
Stevens, T., et al. (2000) Mechanisms regulating endothelial cell barrier function. *American Journal of Physiology Lung Cellular and Molecular Physiology* 279: L419-422.
Stoops, S. L., et al. (2011) Identification and optimization of small molecules that restore E-cadherin expression and reduce invasion in colorectal carcinoma cells. *ACS Chemical Biology* 6: 452-465.
Suzuki, H., et al. (2002) A genomic screen for genes upregulated by demethylation and histone deacetylase inhibition in human colorectal cancer. *Nat. Genet.* 31: 141-149.
Unger, R. E., et al. (2002) In vitro expression of the endothelial phenotype: comparative study of primary isolated cells and cell lines, including the novel cell line HPMEC-ST1.6R. *Microvascular Research* 64: 384-397.

(Continued)

*Primary Examiner* — Zinna Northington Davis
(74) *Attorney, Agent, or Firm* — Ballard Spahr LLP

(57) ABSTRACT

In one aspect, the invention relates to N-((arylamino)alkyl)-5-arylisoxazole-3-carboxamide analogs, derivatives thereof, and related compounds, which are useful as mediators of transcriptional induction of E-cadherin; synthesis methods for making the compounds; pharmaceutical compositions comprising the compounds; and methods of treating disorders associated with E-cadherin activity using the compounds and compositions. This abstract is intended as a scanning tool for purposes of searching in the particular art and is not intended to be limiting of the present invention.

20 Claims, No Drawings

(56) References Cited

OTHER PUBLICATIONS

Valastyan, S., et al. (2011) Activation of miR-31 function in already-established metastases elicits metastatic regression. *Genes Dev.* 25: 646-659.

Vestweber, D. (2008) VE-cadherin: the major endothelial adhesion molecule controlling cellular junctions and blood vessel formation. *Arteriosclerosis, Thrombosis, and Vascular Biology* 28: 223-232.

Wang, Y. and Shang, Y. (2013) Epigenetic control of epithelial-to-mesenchymal transition and cancer metastasis. *Experimental Cell Research* 319: 160-169.

Zijlstra, A., et al. (2008) The inhibition of tumor cell intravasation and subsequent metastasis via regulation of in vivo tumor cell motility by the tetraspanin CD151. *Cancer Cell* 13(3): 221-234.

U.S. Appl. No. 62/040,972, filed Aug. 22, 2014, Craig W. Lindsley.

U.S. Appl. No. 62/040,984, filed Aug. 22, 2014, Craig W. Lindsley.

* cited by examiner

ISOXAZOLE ANALOGS AS MEDIATORS OF TRANSCRIPTIONAL INDUCTION OF E-CADHERIN

CROSS-REFERENCE TO RELATED APPLICATIONS

This Application claims the benefit of U.S. Provisional Application No. 62/040,984, filed on Aug. 22, 2014, which is incorporated herein by reference in its entirety.

STATEMENT REGARDING FEDERALLY SPONSORED RESEARCH

This invention was made with U.S. Government support under grant numbers U54MH084659 and P50CA095103, awarded by the National Institute of Health (NIH). The U.S. government has certain rights in the invention.

BACKGROUND

Cancer is a leading cause of death in in the United States (~25% of the population), and the vast majority of these cancers are of epithelial cell origin (Jemal, A., et al. (2007) *CA: A Cancer Journal for Clinicians* 57, 43-66). Over 90% of cancer deaths related to solid malignancies are due to metastatic dissemination of cancer to secondary organs (Gupta, G. P. and Massague, J. (2006) *Cell* 127, 679-695; Valastyan, S., et al. (2011) *Genes Dev.* 25, 646-659). A hallmark of tumor malignancy, and a requirement for metastasis, is the acquired ability of cells to detach from the primary tumor mass and invade into surrounding stromal tissues. This capacity is highly associated with the loss of expression of epithelial cadherin (E-cadherin), since most solid tumors are carcinomas that are derived from epithelial cells/tissues. E-cadherin is a key adhesion molecule that plays a pivotal role in maintaining cell polarity, epithelial architecture, and cell differentiation. The epithelial-mesenchymal transition (EMT) is a reversible process whereby epithelial cells undergo coordinated reprogramming of their gene expression and lose the epithelial characteristics of tight cell-cell adhesiveness and apical-basal polarity, while gaining mesenchymal properties, including increased motility and capacity for invasion through the basement membrane (Valastyan, S., et al. (2011) *Genes Dev.* 25, 646-659; Katsuno, Y., et al. (2013) *Current Opinion in Oncology* 25, 76-84; Lim, J., et a. (2012) *Development* 139, 3471-3486). Gene expression profiling has indicated that de-differentiated cancer cells combine the EMT properties with a stem-cell like phenotype.

As a feature of the reprogramming of gene expression during EMT, an invariable hallmark of EMT is the marked decrease of E-cadherin expression and function. Alterations in E-cadherin expression have a major impact on cell-cell interactions, resulting in disturbed epithelial tissue homeostasis. Indeed, upon loss of functional E-cadherin, cells become more prone to acquire a motile and invasive phenotype, accounting for the metastatic potential of many epithelial cancer cells. The expression of E-cadherin is frequently lost in human cancers, and while this can be due to mutational inactivation (as in familial gastric cancer syndrome), more frequently the loss of expression is due to transcriptional inhibition or silencing (as occurs in EMT). Several developmentally important transcriptional regulatory proteins, such as ZEB1, ZEB2, Snai1, Snai2/SLUG, TWIST 1, and E47/TCF3, induce EMT and are directly involved in repression of E-cadherin expression (Wang, Y. and Shang, Y. (2013) *Experimental Cell Research* 319, 160-169).

Despite knowledge that the acquisition of EMT features is associated with chemoresistance, often leading to recurrence and metastasis after standard chemotherapeutic treatment (Iwatsuki, M., et al. (2010) *Cancer Sci.* 101, 293-299), very few experimental therapeutic agents are known to inhibit the EMT phenotype. These needs and other needs are addressed by the present invention.

SUMMARY

In accordance with the purpose(s) of the invention, as embodied and broadly described herein, the invention, in one aspect, relates to N-(3-(arylamino)alkyl)-5-arylisoxazole-3-carboxamide analogs useful as mediators of transcriptional induction of E-cadherin (E-cad), methods of making same, pharmaceutical compositions comprising same, and methods of treating cancers associated with functional loss of E-cadherin using same.

Disclosed are compound having a structure represented by a formula:

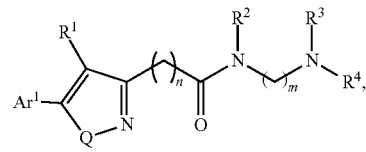

wherein m is an integer selected from 3 and 4; wherein n is an integer selected from 0 and 1; wherein Q is selected from $NR^5$, O, and S; wherein $R^5$, when present, is selected from hydrogen and C1-C4 alkyl; wherein each of $R^1$ and $R^2$ is independently selected from hydrogen and C1-C4 alkyl; wherein $R^3$ is selected from hydrogen and $(CHR^6)_pAr^2$; wherein p, when present, is an integer selected from 0 and 1; wherein $R^6$, when present, is selected from hydrogen and C1-C4 alkyl; wherein $Ar^2$, when present, is selected from aryl and heteroaryl, and $Ar^2$ is substituted with 0, 1, 2, or 3 groups independently selected from halogen, —OH, —CN, —$N_3$, —$NH_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino; wherein $R^4$ is selected from $CH_2Ar^3$ and $Ar^4$; wherein $Ar^3$, when present, is selected from aryl and heteroaryl, and $Ar^3$ is substituted with 0, 1, 2, or 3 groups independently selected from halogen, —OH, —CN, —$N_3$, —$NH_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino, provided that when $R^2$ is hydrogen then $Ar^3$, when present, cannot be a structure selected from:

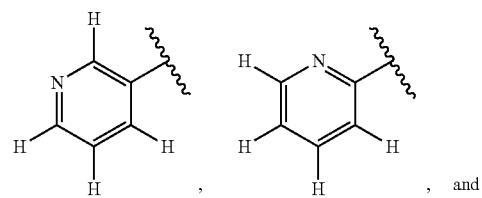

and

-continued

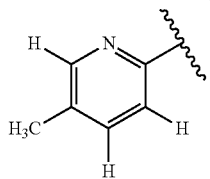

wherein Ar⁴, when present, is selected from aryl and heteroaryl, and Ar⁴ is substituted with 0, 1, 2, or 3 groups independently selected from halogen, —OH, —CN, —NH₂, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino, provided that when R² is hydrogen then Ar³, when present, cannot be a structure selected from:

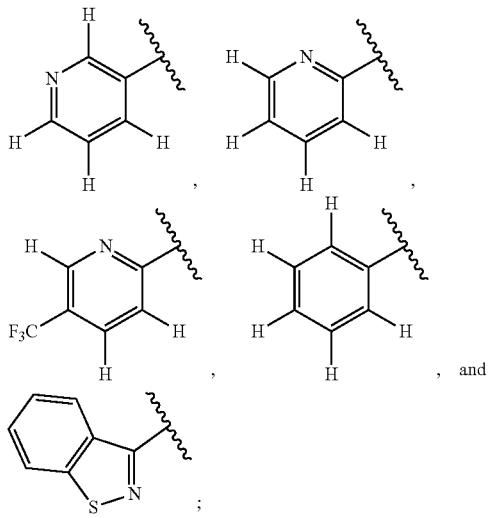

and wherein Ar¹, when present, is selected from aryl and heteroaryl, and wherein Ar¹, when present, is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino, or a pharmaceutically acceptable salt thereof.

Also disclosed are pharmaceutical compositions comprising an effective amount of at least one disclosed compound, or a pharmaceutically acceptable salt thereof, and a pharmaceutically acceptable carrier.

Also disclosed are methods for manufacturing a medicament comprising combining at least one disclosed compound with a pharmaceutically acceptable carrier or diluent.

Also disclosed are methods for modulating the expression of E-cadherin in at least one cell, the method comprising the step of contacting the at least one cell with at least one compound having a structure represented by a formula:

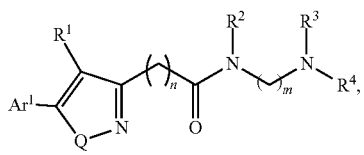

wherein m is an integer selected from 2, 3, and 4; wherein n is an integer selected from 0 and 1; wherein Q is selected from NR⁵, O, and S; wherein R⁵, when present, is selected from hydrogen and C1-C4 alkyl; wherein each of R¹ and R² is independently selected from hydrogen and C1-C4 alkyl; wherein R³ is selected from hydrogen and (CHR⁶)ₚAr²; wherein p, when present, is an integer selected from 0 and 1; wherein R⁶, when present, is selected from hydrogen and C1-C4 alkyl; from hydrogen and C1-C4 alkyl; wherein Ar², when present, is selected from aryl and heteroaryl, and Ar² is substituted with 0, 1, 2, or 3 groups independently selected from halogen, —OH, —CN, —N₃, —NH₂, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino; wherein R⁴ is selected from CH₂Ar³ and Ar⁴; wherein Ar³, when present, is selected from aryl and heteroaryl, and Ar³ is substituted with 0, 1, 2, or 3 groups independently selected from halogen, —OH, —CN, —N₃, —NH₂, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino; wherein Ar⁴, when present, is selected from aryl and heteroaryl, and Ar⁴ is substituted with 0, 1, 2, or 3 groups independently selected from halogen, —OH, —CN, —N₃, —NH₂, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino; and wherein Ar¹, when present, is selected from aryl and heteroaryl, and wherein Ar¹, when present, is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino, or a pharmaceutically acceptable salt thereof.

Also disclosed are methods for treating a disorder associated with E-cadherin activity in a subject, the method comprising administering to the subject an effective amount of at least one compound having a structure represented by a formula:

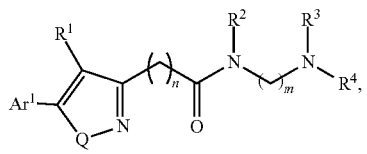

wherein m is an integer selected from 2, 3, and 4; wherein n is an integer selected from 0 and 1; wherein Q is selected from NR⁵, O, and S; wherein R⁵, when present, is selected from hydrogen and C1-C4 alkyl; wherein each of R¹ and R² is independently selected from hydrogen and C1-C4 alkyl; wherein R³ is selected from hydrogen and (CHR⁶)ₚAr²; wherein p, when present, is an integer selected from 0 and 1; wherein R⁶, when present, is selected from hydrogen and C1-C4 alkyl; wherein Ar², when present, is selected from aryl and heteroaryl, and Ar² is substituted with 0, 1, 2, or 3 groups independently selected from halogen, —OH, —CN, —N₃, —NH₂, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino; wherein R⁴ is selected from CH₂Ar³ and Ar⁴; wherein Ar³, when present, is selected from aryl and heteroaryl, and Ar³ is substituted with 0, 1, 2, or 3 groups independently selected from halogen, —OH, —CN, —N₃, —NH₂, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino;

wherein Ar⁴, when present, is selected from aryl and heteroaryl, and Ar⁴ is substituted with 0, 1, 2, or 3 groups independently selected from halogen, —OH, —CN, —N₃, —NH₂, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino; and wherein Ar¹, when present, is selected from aryl and heteroaryl, and wherein Ar¹, when present, is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino, or a pharmaceutically acceptable salt thereof, thereby treating the disorder in the subject.

Also disclosed are kits comprising at least one compound having a structure represented by a formula:

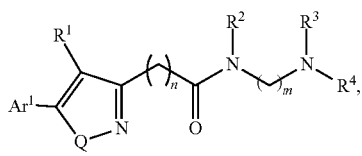

wherein m is an integer selected from 2, 3, and 4; wherein n is an integer selected from 0 and 1; wherein Q is selected from NR⁵, O, and S; wherein R⁵, when present, is selected from hydrogen and C1-C4 alkyl; wherein each of R¹ and R² is independently selected from hydrogen and C1-C4 alkyl; wherein R³ is selected from hydrogen and (CHR⁶)$_p$Ar²; wherein p, when present, is an integer selected from 0 and 1; wherein R⁶, when present, is selected from hydrogen and C1-C4 alkyl; wherein Ar², when present, is selected from aryl and heteroaryl, and Ar² is substituted with 0, 1, 2, or 3 groups independently selected from halogen, —OH, —CN, —N₃, —NH₂, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino; wherein R⁴ is selected from CH₂Ar³ and Ar⁴; wherein Ar³, when present, is selected from aryl and heteroaryl, and Ar³ is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino; wherein Ar⁴, when present, is selected from aryl and heteroaryl, and Ar⁴ is substituted with 0, 1, 2, or 3 groups independently selected from halogen, —OH, —CN, —N₃, —NH₂, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino; and wherein Ar¹, when present, is selected from aryl and heteroaryl, and wherein Ar¹, when present, is substituted with 0, 1, 2, or 3 groups independently selected from halogen, —OH, —CN, —N₃, —NH₂, C1-C4 alkyl, C1-C4 alkoxy, C1-C4 monohaloalkyl, C1-C4 polyhaloalkyl, C1-C4 alkylamino, and C1-C4 dialkylamino, or a pharmaceutically acceptable salt thereof, and one or more of: (a) at least one agent known to increase E-cadherin expression; (b) at least one agent known to decrease E-cadherin expression; (c) at least one agent known to treat a disorder of uncontrolled cellular proliferation; or (d) instructions for treating a disorder of uncontrolled cellular proliferation.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of a cancer prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a cancer treatable by restoration of E-cadherin expression" means having been subjected to a physical examination by a person of skill, for example, a physician, and found to have a condition that can be diagnosed or treated by a compound or composition that can restore E-cadherin expression. As a further example, "diagnosed with a need for restoration of E-cadherin expression" refers to having been subjected to a physical examination by a person of skill, for example, a physician, and found to have a condition characterized by loss of E-cadherin expression. Such a diagnosis can be in reference to a disease, such as a cancer, and the like, as discussed herein.

As used herein, the phrase "identified to be in need of treatment for a disease," or the like, refers to selection of a subject based upon need for treatment of the disease. For example, a subject can be identified as having a need for treatment of a disease (e.g., a disease related to E-cadherin expression) based upon an earlier diagnosis by a person of skill and thereafter subjected to treatment for the disease. It is contemplated that the identification can, in one aspect, be performed by a person different from the person making the diagnosis. It is also contemplated, in a further aspect, that the administration can be performed by one who subsequently performed the identification.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell or other biological entity together in such a manner that the compound can affect the activity of the target (e.g., spliceosome, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "$EC_{50}$," is intended to refer to the concentration of a substance (e.g., a compound or a drug) that is required for 50% potentiation of a biological process, or component of a process, including a protein, subunit, organelle, ribonucleoprotein, etc. In a further aspect, $EC_{50}$ refers to the concentration of agonist that provokes a response halfway between the baseline and maximum response. In a yet further aspect, the response is in vitro.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions that are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible groups of organic compounds. In a broad aspect, the permissible groups include acyclic and cyclic, branched and unbranched, carbocyclic and heterocyclic, and aromatic and nonaromatic groups of organic compounds. Illustrative groups include, for example, those described below. The permissible groups can be one or more and the same or different for appropriate organic compounds. For purposes of this disclosure, the heteroatoms, such as nitrogen, can have hydrogen groups and/or any permissible groups of organic compounds described herein which satisfy the valences of the heteroatoms. This disclosure is not intended to be limited in any manner by the permissible groups of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual groups can be further optionally substituted (i.e., further substituted or unsubstituted).

In defining various terms, "$A^1$," "$A^2$," "$A^3$," and "$A^4$" are used herein as generic symbols to represent various specific groups. These symbols can be any substituent, not limited to those disclosed herein, and when they are defined to be certain groups in one instance, they can, in another instance, be defined as some other groups.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bond. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2)π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide", as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further nonlimiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of groups envisioned by this invention are preferably those that result in the formation of stable or chemically feasible compounds. It is also contemplated that, in certain aspects, unless expressly indicated to the contrary, individual groups can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent groups on a substitutable carbon atom of an "optionally substituted" group is independently halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}$ $SR°$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$(CH_2)_{0-4}O(CH_2)_{0-1}$-pyridyl which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —C(S)R°; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —C(S)SR°; —SC(S)SR°, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)O—$N(R°)_2$; or —$(C_{1-4}$ straight or branched alkylene)C(O)O—$N(R°)_2$, wherein each $R°$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent groups on $R°$ (or the ring formed by taking two independent occurrences of $R°$ together with their intervening atoms), is independently halogen, —$(CH_2)_{0-2}R^●$, -(haloR$^●$), —$(CH_2)_{0-2}OH$, —$(CH_2)_{0-2}OR^●$, —$(CH_2)_{0-2}CH(OR^●)_2$; —O(haloR$^●$), —CN, —$N_3$, —$(CH_2)_{0-2}C(O)R^●$, —$(CH_2)_{0-2}C(O)OH$, —$(CH_2)_{0-2}C(O)OR^●$, —$(CH_2)_{0-2}SR^●$, —$(CH_2)_{0-2}SH$, —$(CH_2)_{0-2}NH_2$, —$(CH_2)_{0-2}NHR^●$, —$(CH_2)_{0-2}NR^●_2$, —$NO_2$, —$SiR^●_3$, —$OSiR^●_3$, —$C(O)SR^●$, —$(C_{1-4}$ straight or branched alkylene)C(O)OR$^●$, or —SSR$^●$ wherein each $R^●$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent groups on a saturated carbon atom of $R°$ include =O and =S.

Suitable divalent groups on a saturated carbon atom of an "optionally substituted" group include the following: =O, =S, =$NNR^*_2$, =$NNHC(O)R^*$, =$NNHC(O)OR^*$, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent groups that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable groups on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable groups on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable groups on the aliphatic group of R$^\dagger$ is independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon-containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited to alkyl or substituted alkyls, alkoxy or substituted alkoxy, mono or di-substituted amino, amide groups, etc. Organic residues can preferably comprise 1 to 18 carbon atoms, 1 to 15 carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15 carbon atoms, 2 to 12 carbon atoms, 2 to 8 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

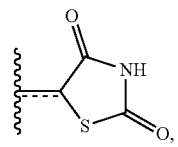

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include, but are not limited to, an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules that owe their stability through non-covalent interaction. One or more components of this molecular complex provide a stable framework in the crystalline lattice. In certain instances, the guest molecules are incorporated in the crystalline lattice as anhydrates or solvates, see e.g., "Crystal Engineering of the Composition of Pharmaceutical Phases. Do Pharmaceutical Co-crystals Represent a New Path to Improved Medicines?" Almarasson, O. et al. (2004) The Royal Society of Chemistry, 1889-1896. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

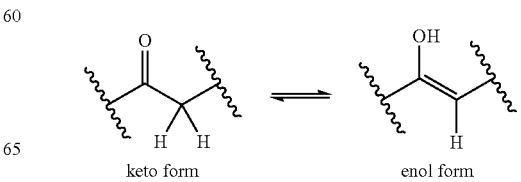

keto form          enol form

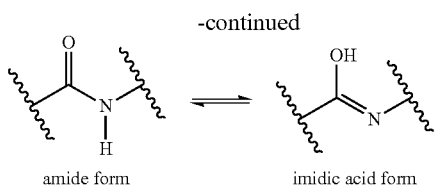

amide form     imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

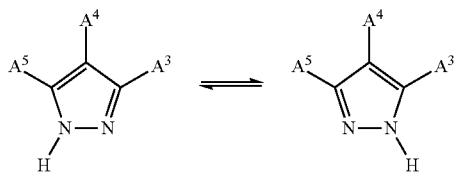

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

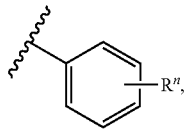

which is understood to be equivalent to a formula:

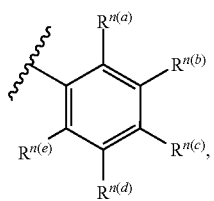

wherein n is typically an integer. That is, $R^n$ is understood to represent five independent groups, $R^{n(a)}$, $R^{n(b)}$, $R^{n(c)}$, $R^{n(d)}$, $R^{n(e)}$. By "independent groups," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental Volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful as mediators of transcriptional induction of E-cadherin. More specifically, in one aspect, the present invention relates to compounds that promote E-cadherin expression.

In one aspect, the disclosed compounds exhibit an increase in E-cadherin mRNA levels as an increase in E-cadherin mRNA expression in SW620 colon cancer cells in the presence of the compound, compared to E-cadherin mRNA expression in the absence of the compound. In a further aspect, the disclosed compounds exhibit an increase in E-cadherin protein levels as an increase in E-cadherin protein levels in SW620 colon cancer cells in the presence of the compound, compared to E-cadherin mRNA protein expression in the absence of the compound.

In one aspect, the compounds of the invention are useful in the treatment of cancers and other diseases associated with loss of E-cadherin expression, as described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, compound can have a structure represented by a formula:

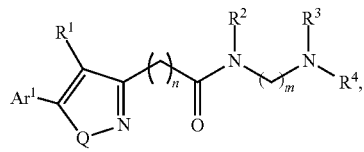

wherein m is an integer selected from 3 and 4; wherein n is an integer selected from 0 and 1; wherein Q is selected from $NR^5$, O, and S; wherein $R^5$, when present, is selected from hydrogen and C1-C4 alkyl; wherein each of $R^1$ and $R^2$ is independently selected from hydrogen and C1-C4 alkyl; wherein $R^3$ is selected from hydrogen and $(CHR^6)_pAr^2$; wherein p, when present, is an integer selected from 0 and 1; wherein $R^6$, when present, is selected from hydrogen and C1-C4 alkyl; wherein $Ar^2$, when present, is selected from aryl and heteroaryl, and $Ar^2$ is substituted with 0, 1, 2, or 3 groups independently selected from halogen, —OH, —CN, —$N_3$, —$NH_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino; wherein $R^4$ is selected from $CH_2Ar^3$ and $Ar^4$; wherein $Ar^3$, when present, is selected from aryl and heteroaryl, and $Ar^3$ is substituted with 0, 1, 2, or 3 groups independently selected from halogen, —OH, —CN, —$N_3$, —$NH_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino, provided that when $R^2$ is hydrogen then $Ar^3$, when present, cannot be a structure selected from:

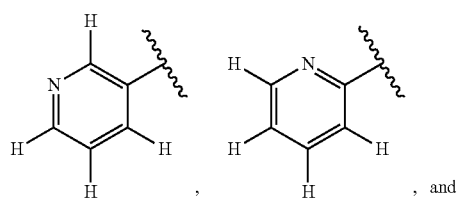

, and

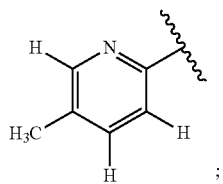

;

wherein $Ar^4$, when present, is selected from aryl and heteroaryl, and $Ar^4$ is substituted with 0, 1, 2, or 3 groups independently selected from halogen, —OH, —CN, —$NH_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino, provided that when $R^2$ is hydrogen then $Ar^3$, when present, cannot be a structure selected from:

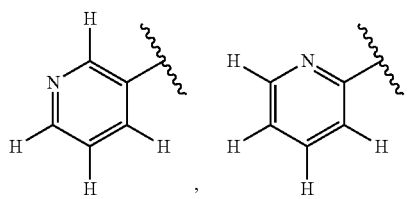

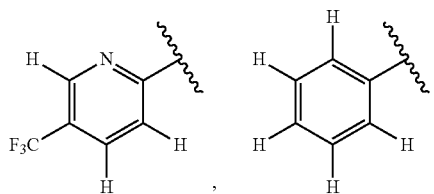

, and

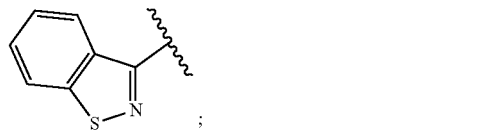

;

and wherein $Ar^1$, when present, is selected from aryl and heteroaryl, and wherein $Ar^1$, when present, is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino, or a pharmaceutically acceptable salt thereof.

In a further aspect, a compound can have a structure listed herein. In a further aspect, the compounds can be selected from two or more of the structures listed herein.

In a further aspect, the invention relates to a compound having a structure represented by a formula:

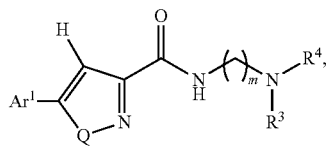

wherein all other variables are as defined herein; or a pharmaceutically acceptable salt thereof.

In a further aspect, the invention relates to a compound having a structure represented by a formula:

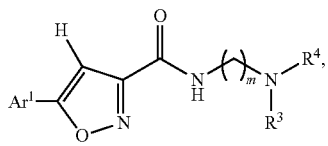

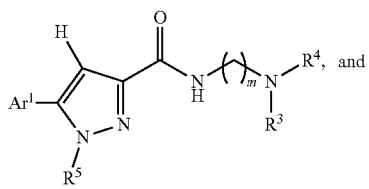

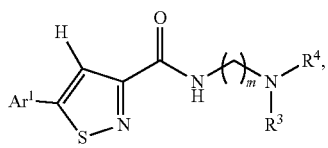

wherein all other variables are as defined herein; or a pharmaceutically acceptable salt thereof.

In a further aspect, the invention relates to a compound having a structure represented by a formula:

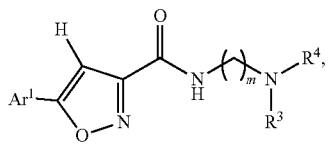

wherein all other variables are as defined herein; or a pharmaceutically acceptable salt thereof.

In a further aspect, the invention relates to a compound having a structure represented by a formula:

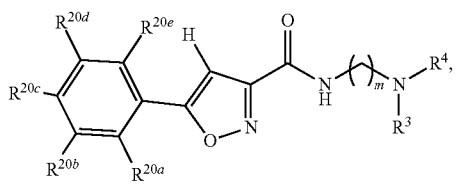

wherein each of $R^{20a}$, $R^{20b}$, $R^{20c}$, $R^{20d}$, and $R^{20e}$ are independently selected from hydrogen, halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino, provided that at least two of $R^{20a}$, $R^{20b}$, $R^{20c}$, $R^{20d}$, and $R^{20e}$ are hydrogen; and wherein all other variables are as defined herein; or a pharmaceutically acceptable salt thereof.

In a further aspect, the invention relates to a compound having a structure represented by a formula:

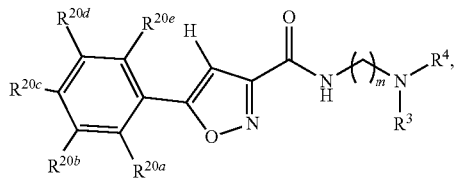

wherein each of $R^{20a}$, $R^{20b}$, $R^{20c}$, $R^{20d}$, and $R^{20e}$ are independently selected from hydrogen, halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino, provided that at least three of $R^{20a}$, $R^{20b}$, $R^{20c}$, $R^{20d}$, and $R^{20e}$ are hydrogen; and wherein all other variables are as defined herein; or a pharmaceutically acceptable salt thereof.

In a further aspect, the invention relates to a compound having a structure represented by a formula:

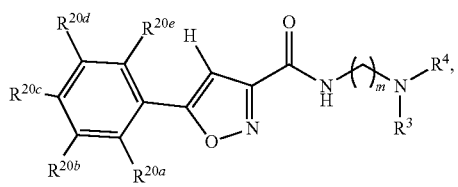

wherein each of $R^{20a}$, $R^{20b}$, $R^{20c}$, $R^{20d}$, and $R^{20e}$ are independently selected from hydrogen, halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino, provided that at least four of $R^{20a}$, $R^{20b}$, $R^{20c}$, $R^{20d}$, and $R^{20e}$ are hydrogen; and wherein all other variables are as defined herein; or a pharmaceutically acceptable salt thereof.

In a further aspect, the invention relates to a compound having a structure represented by a formula:

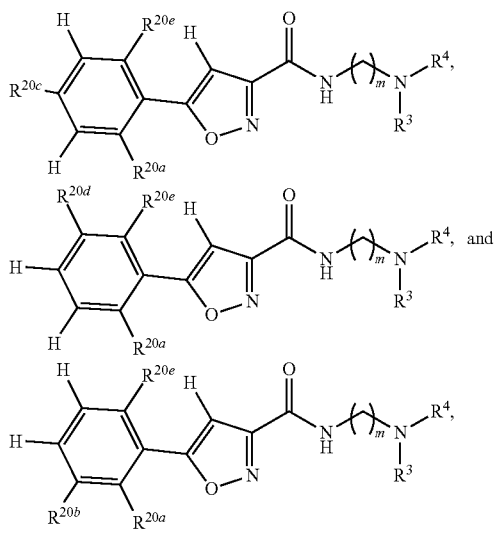

wherein each of $R^{20a}$, $R^{20b}$, $R^{20c}$, $R^{20d}$, and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

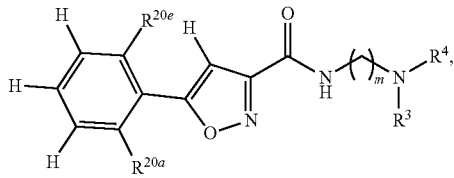

wherein each of $R^{20a}$ and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

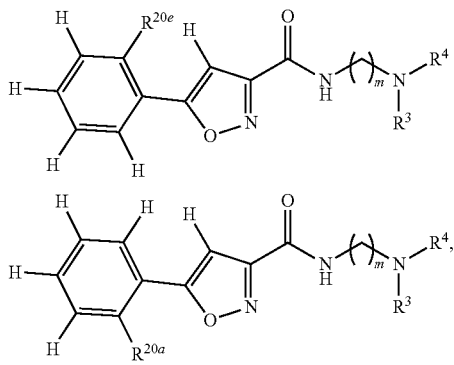

wherein each of $R^{20a}$, $R^{20b}$, $R^{20c}$, $R^{20d}$, and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

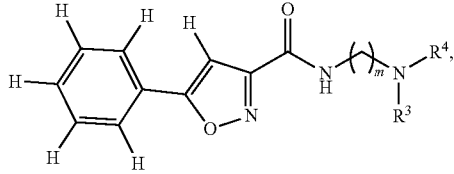

wherein all other variables are as defined herein; or a pharmaceutically acceptable salt thereof.

In a further aspect, the invention relates to a compound having a structure represented by a formula:

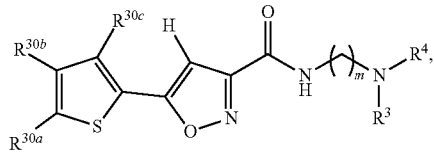

wherein each of $R^{30a}$, $R^{30b}$, and $R^{30c}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; wherein all other variables are as defined herein; or a pharmaceutically acceptable salt thereof.

In a further aspect, the invention relates to a compound having a structure represented by a formula:

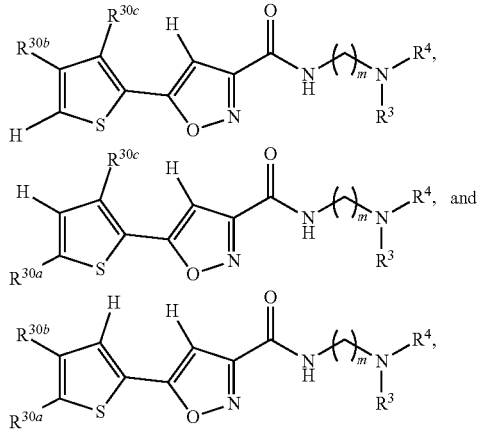

wherein each of $R^{30a}$, $R^{30b}$, and $R^{30c}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; wherein all other variables are as defined herein; or a pharmaceutically acceptable salt thereof.

In a further aspect, the invention relates to a compound having a structure represented by a formula:

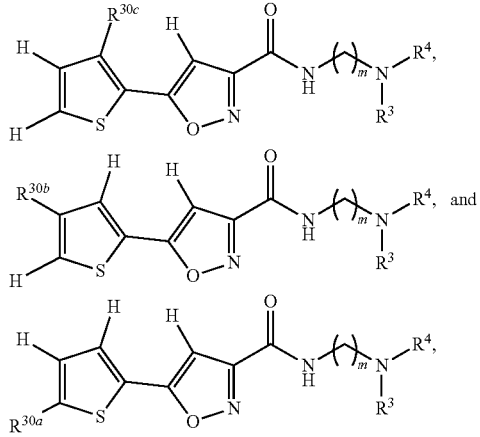

wherein each of $R^{30a}$, $R^{30b}$, and $R^{30c}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; wherein all other variables are as defined herein; or a pharmaceutically acceptable salt thereof.

In a further aspect, the invention relates to a compound having a structure represented by a formula:

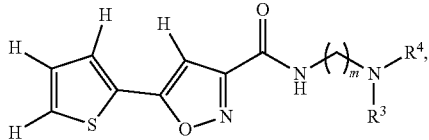

wherein all other variables are as defined herein; or a pharmaceutically acceptable salt thereof.

In a further aspect, the invention relates to a compound having a structure represented by a formula:

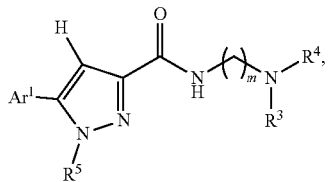

wherein all other variables are as defined herein; or a pharmaceutically acceptable salt thereof.

In a further aspect, the invention relates to a compound having a structure represented by a formula:

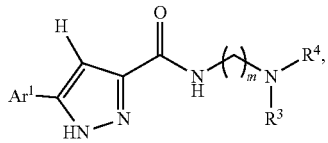

wherein all other variables are as defined herein; or a pharmaceutically acceptable salt thereof.

In a further aspect, the invention relates to a compound having a structure represented by a formula:

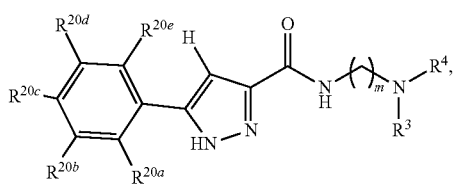

wherein each of $R^{20a}$, $R^{20b}$, $R^{20c}$, $R^{20d}$, and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino, provided that at least two of $R^{20a}$, $R^{20b}$, $R^{20c}$, $R^{20d}$, and $R^{20e}$ are hydrogen; and wherein all other variables are as defined herein; or a pharmaceutically acceptable salt thereof.

In a further aspect, the invention relates to a compound having a structure represented by a formula:

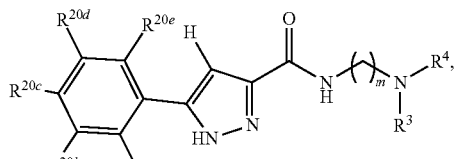

wherein each of $R^{20a}$, $R^{20b}$, $R^{20c}$, $R^{20d}$, and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino, provided that at least three of $R^{20a}$, $R^{20b}$, $R^{20c}$, $R^{20d}$ and $R^{20e}$ are hydrogen; and wherein all other variables are as defined herein; or a pharmaceutically acceptable salt thereof.

In a further aspect, the invention relates to a compound having a structure represented by a formula:

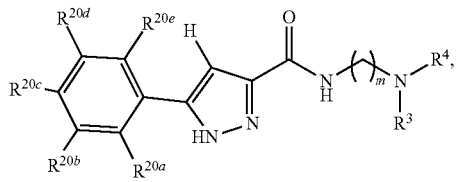

wherein each of $R^{20a}$, $R^{20b}$, $R^{20c}$, $R^{20d}$, and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino, provided that at least four of $R^{20a}$, $R^{20b}$, $R^{20c}$, $R^{20d}$, and $R^{20e}$ are hydrogen; and wherein all other variables are as defined herein; or a pharmaceutically acceptable salt thereof.

In a further aspect, the invention relates to a compound having a structure represented by a formula:

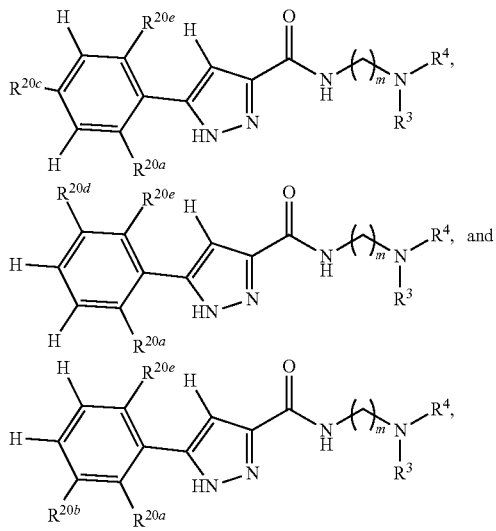

wherein each of $R^{20a}$, $R^{20b}$, $R^{20c}$, $R^{20d}$ and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

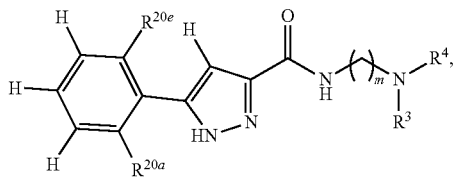

wherein each of $R^{20a}$ and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

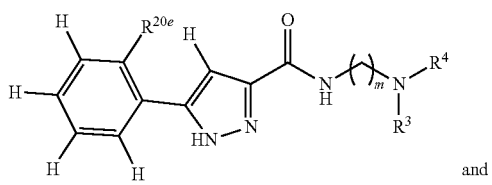

and

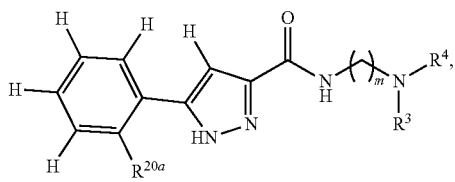

wherein each of $R^{20a}$ and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

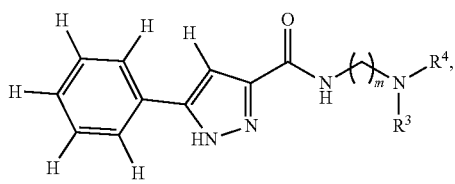

wherein all other variables are as defined herein; or a pharmaceutically acceptable salt thereof.

In a further aspect, the invention relates to a compound having a structure represented by a formula:

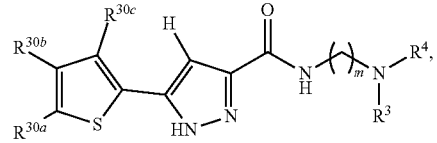

wherein each of $R^{30a}$, $R^{30b}$, and $R^{30c}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; wherein all other variables are as defined herein; or a pharmaceutically acceptable salt thereof.

In a further aspect, the invention relates to a compound having a structure represented by a formula:

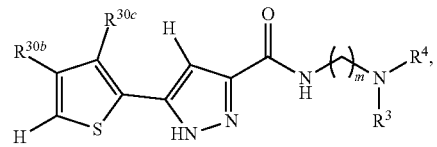

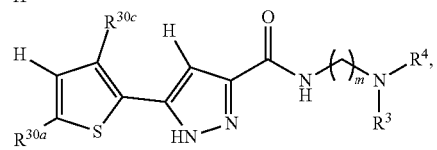

and

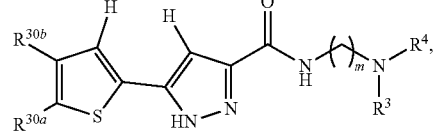

wherein each of $R^{30a}$, $R^{30b}$, and $R^{30c}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; wherein all other variables are as defined herein; or a pharmaceutically acceptable salt thereof.

In a further aspect, the invention relates to a compound having a structure represented by a formula:

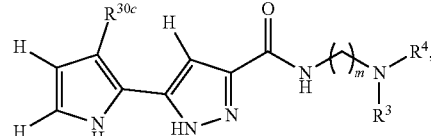

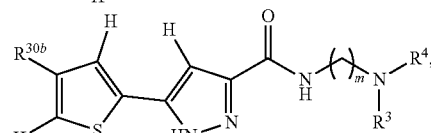

and

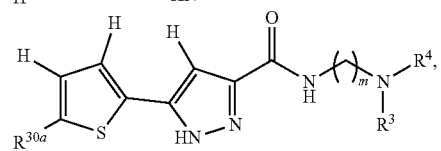

wherein each of $R^{30a}$, $R^{30b}$, and $R^{30c}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; wherein all other variables are as defined herein; or a pharmaceutically acceptable salt thereof.

In a further aspect, the invention relates to a compound having a structure represented by a formula:

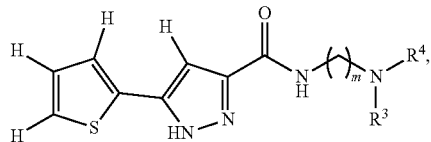

wherein all other variables are as defined herein; or a pharmaceutically acceptable salt thereof.

In a further aspect, the invention relates to a compound having a structure represented by a formula:

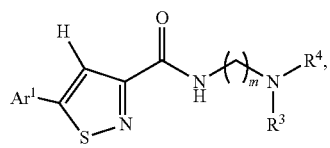

wherein all other variables are as defined herein; or a pharmaceutically acceptable salt thereof.

In a further aspect, the invention relates to a compound having a structure represented by a formula:

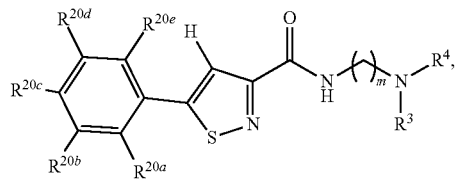

wherein each of $R^{20a}$, $R^{20b}$, $R^{20c}$, $R^{20d}$, and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino, provided that at least two of $R^{20a}$, $R^{20b}$, $R^{20c}$, $R^{20d}$, and $R^{20e}$ are hydrogen; and wherein all other variables are as defined herein; or a pharmaceutically acceptable salt thereof.

In a further aspect, the invention relates to a compound having a structure represented by a formula:

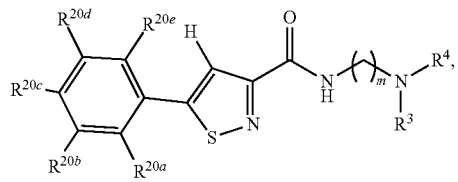

wherein each of $R^{20a}$, $R^{20b}$, $R^{20c}$, $R^{20d}$, and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino, provided that at least three of $R^{20a}$, $R^{20b}$, $R^{20c}$, $R^{20d}$, and $R^{20e}$ are hydrogen; and wherein all other variables are as defined herein; or a pharmaceutically acceptable salt thereof.

In a further aspect, the invention relates to a compound having a structure represented by a formula:

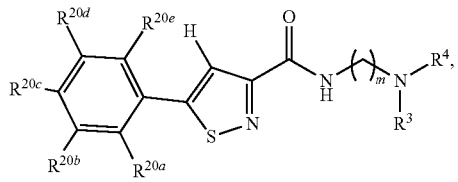

wherein each of $R^{20a}$, $R^{20b}$, $R^{20c}$, $R^{20d}$, and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino, provided that at least four of $R^{20a}$, $R^{20b}$, $R^{20c}$, $R^{20d}$, and $R^{20e}$ are hydrogen; and wherein all other variables are as defined herein; or a pharmaceutically acceptable salt thereof.

In a further aspect, the invention relates to a compound having a structure represented by a formula:

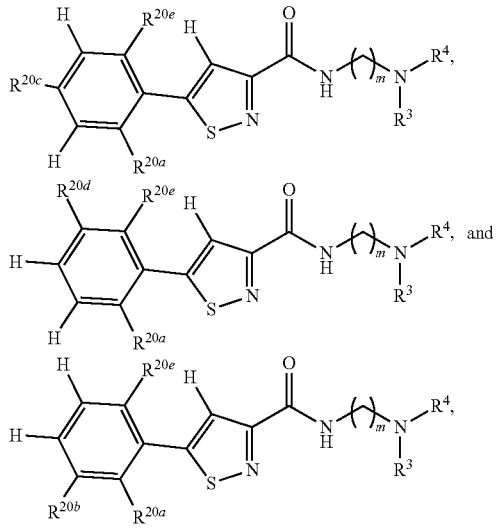

wherein each of $R^{20a}$, $R^{20b}$, $R^{20c}$, $R^{20d}$, and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

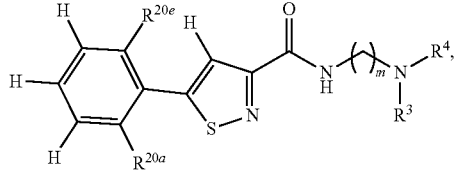

wherein each of $R^{20a}$ and $R^{20e}$ are independently selected from hydrogen, halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

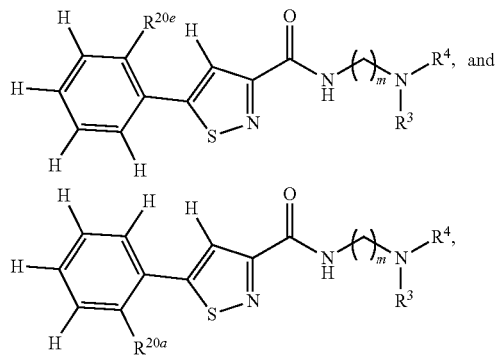

wherein each of $R^{20a}$ and $R^{20e}$ are independently selected from hydrogen, halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino; and wherein all other variables are as defined herein; or a pharmaceutically acceptable salt thereof.

In a further aspect, the invention relates to a compound having a structure represented by a formula:

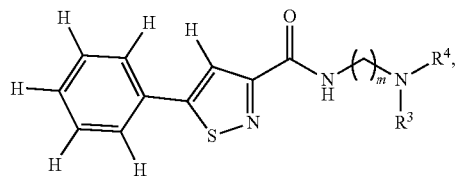

wherein all other variables are as defined herein; or a pharmaceutically acceptable salt thereof.

In a further aspect, the invention relates to a compound having a structure represented by a formula:

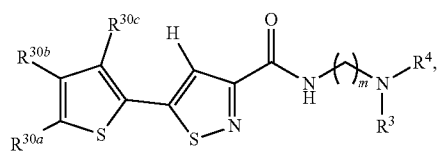

wherein each of $R^{30a}$, $R^{30b}$, and $R^{30c}$ are independently selected from hydrogen, halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino; wherein all other variables are as defined herein; or a pharmaceutically acceptable salt thereof.

In a further aspect, the invention relates to a compound having a structure represented by a formula:

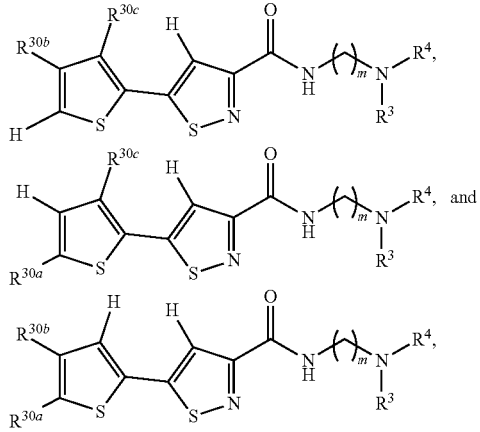

wherein each of $R^{30a}$, $R^{30b}$, and $R^{30c}$ are independently selected from hydrogen, halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino; wherein all other variables are as defined herein; or a pharmaceutically acceptable salt thereof.

In a further aspect, the invention relates to a compound having a structure represented by a formula:

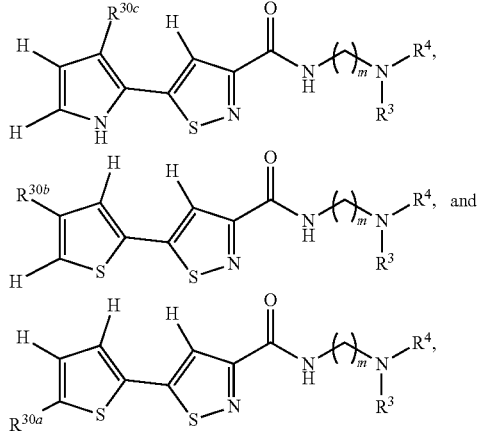

wherein each of $R^{30a}$, $R^{30b}$, and $R^{30c}$ are independently selected from hydrogen, halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino; wherein all other variables are as defined herein; or a pharmaceutically acceptable salt thereof.

In a further aspect, the invention relates to a compound having a structure represented by a formula:

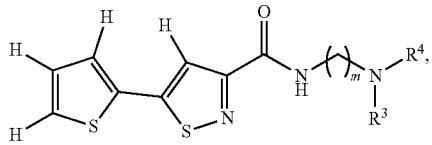

wherein all other variables are as defined herein; or a pharmaceutically acceptable salt thereof.

In one aspect, m is an integer selected from 3 and 4. In a further aspect, m is 4. In a still further aspect, m is 3.

In one aspect, m is an integer selected from 2, 3, and 4. In a further aspect, m is an integer selected from 3 and 4. In a still further aspect, m is an integer selected from 2 and 3. In yet a further aspect, m is 4. In an even further aspect, m is 3. In a still further aspect, m is 2.

In one aspect, n is an integer selected from 0 and 1. In a further aspect, n is 1. In a still further aspect, n is 0.

In one aspect, p, when present, is an integer selected from 0 and 1. In a further aspect, p, when present, is 1. In a still further aspect, p, when present, is 0.

a. Q

In one aspect, Q is selected from $NR^5$, O, and S. In a further aspect, Q is selected from $NR^5$ and O. In a still further aspect, Q is selected from O and S. In yet a further aspect, Q is $NR^5$. In an even further aspect, Q is O. In a still further aspect, Q is S.

b. $R^1$ Groups

In one aspect, $R^1$ is selected from hydrogen and C1-C4 alkyl. In a further aspect, $R^1$ is C1-C4 alkyl. In a still further aspect, $R^1$ is ethyl. In yet a further aspect, $R^1$ is methyl. In an even further aspect, $R^1$ is hydrogen.

In a further aspect, $R^1$ is selected from hydrogen, methyl, ethyl, propyl, isopropyl, tert-butyl, sec-butyl, and isobutyl. In a still further aspect, $R^1$ is selected from hydrogen, methyl, ethyl, propyl, and isopropyl. In yet a further aspect, $R^1$ is selected from hydrogen, methyl, and ethyl. In an even further aspect, $R^1$ is selected from hydrogen and ethyl. In a still further aspect, $R^1$ is selected from hydrogen and methyl.

c. $R^2$ Groups

In one aspect, $R^2$ is selected from hydrogen and C1-C4 alkyl. In a further aspect, $R^2$ is C1-C4 alkyl. In a still further aspect, $R^2$ is ethyl. In yet a further aspect, $R^2$ is methyl. In an even further aspect, $R^2$ hydrogen.

In a further aspect, $R^2$ is selected from hydrogen, methyl, ethyl, propyl, isopropyl, tert-butyl, sec-butyl, and isobutyl. In a still further aspect, $R^2$ is selected from hydrogen, methyl, ethyl, propyl, and isopropyl. In yet a further aspect, $R^2$ is selected from hydrogen, methyl, and ethyl. In an even further aspect, $R^2$ is selected from hydrogen and ethyl. In a still further aspect, $R^2$ is selected from hydrogen and methyl.

d. $R^3$ Groups

In one aspect, $R^3$ is selected from hydrogen and $(CHR^6)_p Ar^2$. In a further aspect, $R^3$ is $(CHR^6)_p Ar^2$. In a still further aspect, $R^3$ is hydrogen.

e. $R^4$ Groups

In one aspect, $R^4$ is selected from $CH_2Ar^3$ and $Ar^4$. In a further aspect, $R^4$ is $CH_2Ar^3$. In a still further aspect, $R^4$ is $Ar^4$.

f. $R^5$ Groups

In one aspect, $R^5$, when present, is selected from hydrogen and C1-C4 alkyl. In a further aspect, $R^5$, when present, is C1-C4 alkyl. In a still further aspect, $R^5$, when present, is ethyl. In yet a further aspect, $R^5$, when present, is methyl. In an even further aspect, $R^5$, when present, is hydrogen.

In a further aspect, $R^5$, when present, is selected from hydrogen, methyl, ethyl, propyl, isopropyl, tert-butyl, sec-butyl, and isobutyl. In a still further aspect, $R^5$, when present, is selected from hydrogen, methyl, ethyl, propyl, and isopropyl. In yet a further aspect, $R^5$, when present, is selected from hydrogen, methyl, and ethyl. In an even further aspect, $R^5$, when present, is selected from hydrogen and ethyl. In a still further aspect, $R^5$, when present, is selected from hydrogen and methyl.

g. $R^6$ Groups

In one aspect, $R^6$, when present, is selected from hydrogen and C1-C4 alkyl. In a further aspect, $R^6$, when present, is C1-C4 alkyl. In a still further aspect, $R^6$, when present, is ethyl. In yet a further aspect, $R^6$, when present, is methyl. In an even further aspect, $R^6$, when present, is hydrogen.

In a further aspect, p is 0 and $R^6$ is not present. In a still further aspect, p is 1 and $R^6$ is selected from hydrogen and C1-C4 alkyl. In yet a further aspect, p is 1 and $R^6$ is C1-C4 alkyl. In an even further aspect, p is 1 and $R^6$ is ethyl. In a still further aspect, p is 1 and $R^6$ is methyl. In yet a further aspect, p is 1 and $R^6$ is hydrogen.

In a further aspect, $R^6$, when present, is selected from hydrogen, methyl, ethyl, propyl, isopropyl, tert-butyl, sec-butyl, and isobutyl. In a still further aspect, $R^6$, when present, is selected from hydrogen, methyl, ethyl, propyl, and isopropyl. In yet a further aspect, $R^6$, when present, is selected from hydrogen, methyl, and ethyl. In an even further aspect, $R^6$, when present, is selected from hydrogen and ethyl. In a still further aspect, $R^6$, when present, is selected from hydrogen and methyl.

h. $R^{20A}$, $R^{20B}$, $R^{20C}$, $R^{20D}$, and $R^{20E}$ Groups

In one aspect, each of $R^{20a}$, $R^{20b}$, $R^{20c}$, $R^{20d}$, and $R^{20e}$, when present, are independently selected from hydrogen, halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino, provided that at least two of $R^{20a}$, $R^{20b}$, $R^{20c}$, $R^{20d}$, and $R^{20e}$ are hydrogen. In a further aspect, each of $R^{20a}$, $R^{20b}$, $R^{20c}$, $R^{20d}$, and $R^{20e}$, when present, are independently selected from hydrogen, —F, —Cl, —OH, —CN, —$N_3$, —$NH_2$, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$OCH_3$, —$OCH_2CH_3$, —$OCH_2F$, —$OCHF_2$, —$OCF_3$, —$NHCH_3$, and —$N(CH_3)_2$, provided that at least two of $R^{20a}$, $R^{20b}$, $R^{20c}$, $R^{20d}$, and $R^{20e}$ are hydrogen. In a still further aspect, each of $R^{20a}$, $R^{20b}$, $R^{20c}$, $R^{20d}$, and $R^{20e}$, when present, are independently selected from hydrogen, —F, —Cl, —OH, —CN, —$N_3$, —$NH_2$, methyl, —$CH_2F$, —$CH_2Cl$, —$CHF_2$, —$CF_3$, —$CHCl_2$, —$CCl_3$, —$OCH_3$, —$OCH_2F$, —$OCHF_2$, —$OCF_3$, —$NHCH_3$, and —$N(CH_3)_2$, provided that at least two of $R^{20a}$, $R^{20b}$, $R^{20c}$, $R^{20d}$ and $R^{20e}$ are hydrogen. In yet a further aspect, each of $R^{20a}$, $R^{20b}$, $R^{20c}$, $R^{20d}$ and $R^{20e}$, when present, are independently selected from hydrogen, —F, —Cl, —OH, —CN, —$N_3$, —$NH_2$, methyl, —$CF_3$, —$OCH_3$, —$OCF_3$, —$NHCH_3$, and —$N(CH_3)_2$, provided that at least two of $R^{20a}$, $R^{20b}$, $R^{20c}$, $R^{20d}$, and $R^{20e}$ are hydrogen. In an even further aspect, each of $R^{20a}$, $R^{20b}$, $R^{20c}$, $R^{20d}$, and $R^{20e}$, when present, are independently selected from hydrogen, —F, —Cl, —$N_3$, and methyl, provided that at least two of $R^{20a}$, $R^{20b}$, $R^{20c}$, $R^{20d}$, and $R^{20e}$ are hydrogen.

In a further aspect, each of $R^{20a}$, $R^{20b}$, and $R^{20c}$, when present, is hydrogen, and each of $R^{20d}$ and $R^{20e}$, when present, are independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{20a}$, $R^{20b}$, and $R^{20c}$, when present, is hydrogen, and each of $R^{20d}$ and $R^{20e}$, when present, are independently selected from —F, —Cl, —OH, —CN, —$N_3$, —$NH_2$, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$OCH_3$, —$OCH_2CH_3$, —$OCH_2F$, —$OCHF_2$, —$OCF_3$, —$NHCH_3$, and —$N(CH_3)_2$. In yet a further aspect, each of $R^{20a}$, $R^{20b}$ and $R^{20c}$, when present, is hydrogen, and each of $R^{20d}$ and $R^{20e}$, when present, are independently selected from —F, —Cl, —OH, —CN, —$N_3$, —$NH_2$, methyl, —$CH_2F$, —$CH_2Cl$, —$CHF_2$, —$CF_3$, —$CHCl_2$, —$CCl_3$, —$OCH_3$, —$OCH_2F$, —$OCHF_2$, —$OCF_3$, —$NHCH_3$, and —$N(CH_3)_2$. In an even further aspect, each of $R^{20a}$, $R^{20b}$, and $R^{20c}$, when present, is hydrogen, and each of $R^{20d}$ and $R^{20e}$, when present, are independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20a}$, $R^{20b}$, and $R^{20c}$, when present, is hydrogen, and each of $R^{20d}$ and $R^{20e}$, when present, are independently selected from —F, —Cl, —N$_3$, and methyl.

In a further aspect, each of $R^{20a}$, $R^{20b}$, and $R^{20d}$, when present, is hydrogen, and each of $R^{20c}$ and $R^{20e}$, when present, are independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{20a}$, $R^{20b}$ and $R^{20d}$, when present, is hydrogen, and each of $R^{20c}$ and $R^{20e}$, when present, are independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{20a}$, $R^{20b}$ and $R^{20d}$, when present, is hydrogen, and each of $R^{20c}$ and $R^{20e}$, when present, are independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20a}$, $R^{20b}$, and $R^{20d}$, when present, is hydrogen, and each of $R^{20c}$ and $R^{20e}$, when present, are independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20a}$, $R^{20b}$, and $R^{20d}$, when present, is hydrogen, and each of $R^{20c}$ and $R^{20e}$, when present, are independently selected from —F, —Cl, —N$_3$, and methyl.

In a further aspect, each of $R^{20a}$, $R^{20b}$, and $R^{20e}$, when present, is hydrogen, and each of $R^{20c}$ and $R^{20d}$, when present, are independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{20a}$, $R^{20b}$, and $R^{20e}$, when present, is hydrogen, and each of $R^{20c}$ and $R^{20d}$, when present, are independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{20a}$, $R^{20b}$, and $R^{20e}$, when present, is hydrogen, and each of $R^{20c}$ and $R^{20d}$, when present, are independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20a}$, $R^{20b}$ and $R^{20e}$, when present, is hydrogen, and each of $R^{20c}$ and $R^{20d}$, when present, are independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20a}$, $R^{20b}$, and $R^{20e}$, when present, is hydrogen, and each of $R^{20c}$ and $R^{20d}$, when present, are independently selected from —F, —Cl, —N$_3$, and methyl.

In a further aspect, each of $R^{20a}$, $R^{20c}$, and $R^{20d}$, when present, is hydrogen, and each of $R^{20b}$ and $R^{20e}$, when present, are independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{20a}$, $R^{20c}$, and $R^{20d}$, when present, is hydrogen, and each of $R^{20b}$ and $R^{20e}$, when present, are independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{20a}$, $R^{20c}$, and $R^{20d}$, when present, is hydrogen, and each of $R^{20b}$ and $R^{20e}$, when present, are independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20a}$, $R^{20c}$, and $R^{20d}$, when present, is hydrogen, and each of $R^{20b}$ and $R^{20e}$, when present, are independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20a}$, $R^{20c}$, and $R^{20d}$, when present, is hydrogen, and each of $R^{20b}$ and $R^{20e}$, when present, are independently selected from —F, —Cl, —N$_3$, and methyl.

In a further aspect, each of $R^{20a}$, $R^{20c}$, and $R^{20e}$, when present, is hydrogen, and each of $R^{20b}$ and $R^{20d}$, when present, are independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{20a}$, $R^{20c}$, and $R^{20e}$, when present, is hydrogen, and each of $R^{20b}$ and $R^{20d}$, when present, are independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{20a}$, $R^{20c}$, and $R^{20e}$, when present, is hydrogen, and each of $R^{20b}$ and $R^{20d}$, when present, are independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20a}$, $R^{20c}$ and $R^{20e}$, when present, is hydrogen, and each of $R^{20b}$ and $R^{20d}$, when present, are independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20a}$, $R^{20c}$, and $R^{20e}$, when present, is hydrogen, and each of $R^{20b}$ and $R^{20d}$, when present, are independently selected from —F, —Cl, —N$_3$, and methyl.

In a further aspect, each of $R^{20a}$, $R^{20d}$ and $R^{20e}$, when present, is hydrogen, and each of $R^{20b}$ and $R^{20c}$, when present, is independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{20a}$, $R^{20d}$ and $R^{20e}$, when present, is hydrogen, and each of $R^{20b}$ and $R^{20c}$, when present, is independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{20a}$, $R^{20d}$ and $R^{20e}$, when present, is hydrogen, and each of $R^{20b}$ and $R^{20c}$, when present, is independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20a}$, $R^{20d}$ and $R^{20e}$, when present, is hydrogen, and each of $R^{20b}$ and $R^{20c}$, when present, is independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20a}$, $R^{20d}$, and $R^{20e}$, when present, is hydrogen, and each of $R^{20b}$ and $R^{20c}$, when present, is independently selected from —F, —Cl, —N$_3$, and methyl.

In a further aspect, each of $R^{20b}$, $R^{20c}$, and $R^{20d}$, when present, is hydrogen, and each of $R^{20a}$ and $R^{20e}$, when present, is independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{20b}$, $R^{20c}$, and $R^{20d}$, when present, is hydrogen, and each of $R^{20a}$ and $R^{20e}$, when present, is independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{20b}$, $R^{20c}$ and $R^{20d}$, when present, is hydrogen, and each of $R^{20a}$ and $R^{20e}$, when present, is independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20b}$, $R^{20c}$, and $R^{20d}$, when present, is hydrogen, and each of $R^{20a}$ and $R^{20e}$, when present, is independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20b}$, $R^{20c}$, and $R^{20d}$, when present, is hydrogen, and each of $R^{20a}$ and $R^{20e}$, when present, is independently selected from —F, —Cl, —N$_3$, and methyl.

In a further aspect, each of $R^{20b}$, $R^{20d}$, and $R^{20e}$, when present, is hydrogen, and each of $R^{20a}$ and $R^{20c}$, when present, is independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{20b}$, $R^{20d}$, and $R^{20e}$, when present, is hydrogen, and each of $R^{20a}$ and $R^{20c}$, when present, is independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{20b}$, $R^{20d}$ and $R^{20e}$, when present, is hydrogen, and each of $R^{20a}$ and $R^{20c}$, when present, is independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20b}$, $R^{20d}$, and $R^{20e}$, when present, is hydrogen, and each of $R^{20a}$ and $R^{20c}$, when present, is independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20b}$, $R^{20d}$, and $R^{20e}$, when present, is hydrogen, and each of $R^{20a}$ and $R^{20c}$, when present, is independently selected from —F, —Cl, —N$_3$, and methyl.

In a further aspect, each of $R^{20b}$, $R^{20d}$, and $R^{20e}$, when present, is hydrogen, and each of $R^{20a}$ and $R^{20c}$, when present, is independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20b}$, $R^{20d}$, and $R^{20e}$, when present, is hydrogen, and each of $R^{20a}$ and $R^{20c}$, when present, is independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20b}$, $R^{20d}$, and $R^{20e}$, when present, is hydrogen, and each of $R^{20a}$ and $R^{20c}$, when present, is independently selected from —F, —Cl, —N$_3$, and methyl.

In a further aspect, each of $R^{20b}$, $R^{20c}$, and $R^{20e}$, when present, is hydrogen, and each of $R^{20a}$ and $R^{20d}$, when present, is independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{20b}$, $R^{20c}$, and $R^{20e}$, when present, is hydrogen, and each of $R^{20a}$ and $R^{20d}$, when present, is independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{20b}$, $R^{20c}$ and $R^{20e}$, when present, is hydrogen, and each of $R^{20a}$ and $R^{20d}$, when present, is independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20b}$, $R^{20c}$ and $R^{20e}$, when present, is hydrogen, and each of $R^{20a}$ and $R^{20d}$, when present, is independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20b}$, $R^{20c}$, and $R^{20e}$, when present, is hydrogen, and each of $R^{20a}$ and $R^{20d}$, when present, is independently selected from —F, —Cl, —N$_3$, and methyl.

In a further aspect, each of $R^{20c}$, $R^{20d}$, and $R^{20e}$, when present, is hydrogen, and each of $R^{20a}$ and $R^{20b}$, when present, is independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{20c}$, $R^{20d}$, and $R^{20e}$, when present, is hydrogen, and each of $R^{20a}$ and $R^{20b}$, when present, is independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{20c}$, $R^{20d}$, and $R^{20e}$, when present, is hydrogen, and each of $R^{20a}$ and $R^{20b}$, when present, is independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20c}$, $R^{20d}$ and $R^{20e}$, when present, is hydrogen, and each of $R^{20a}$ and $R^{20b}$, when present, is independently selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20c}$, $R^{20d}$, and $R^{20e}$, when present, is hydrogen, and each of $R^{20a}$ and $R^{20b}$, when present, is independently selected from —F, —Cl, —N$_3$, and methyl.

In a further aspect, each of $R^{20a}$, $R^{20b}$, $R^{20c}$, and $R^{20d}$, when present, is hydrogen, and $R^{20e}$, when present, is selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{20a}$, $R^{20b}$, $R^{20c}$, and $R^{20d}$, when present, is hydrogen, and $R^{20e}$, when present, is selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{20a}$, $R^{20b}$, $R^{20c}$, and $R^{20d}$, when present, is hydrogen, and $R^{20e}$, when present, is selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20a}$, $R^{20b}$, $R^{20c}$, and $R^{20d}$, when present, is hydrogen, and $R^{20e}$, when present, is selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20a}$, $R^{20b}$, $R^{20c}$, and $R^{20d}$, when present, is hydrogen, and $R^{20e}$, when present, is selected from —F, —Cl, —N$_3$, and methyl.

In a further aspect, each of $R^{20a}$, $R^{20b}$, $R^{20c}$, and $R^{20e}$, when present, is hydrogen, and $R^{20d}$, when present, is selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{20a}$, $R^{20b}$, $R^{20c}$, and $R^{20e}$, when present, is hydrogen, and $R^{20d}$, when present, is selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{20a}$, $R^{20b}$, $R^{20c}$, and $R^{20e}$, when present, is hydrogen, and $R^{20d}$, when present, is selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20a}$, $R^{20b}$, $R^{20c}$, and $R^{20e}$, when present, is hydrogen, and $R^{20d}$, when present, is selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20a}$, $R^{20b}$, $R^{20c}$, and $R^{20e}$, when present, is hydrogen, and $R^{20d}$, when present, is selected from —F, —Cl, —N$_3$, and methyl.

In a further aspect, each of $R^{20a}$, $R^{20b}$, $R^{20d}$ and $R^{20e}$, when present, is hydrogen, and $R^{20c}$, when present, is selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{20a}$, $R^{20b}$, $R^{20d}$ and $R^{20e}$, when present, is hydrogen, and $R^{20c}$, when present, is selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{20a}$, $R^{20b}$, $R^{20d}$ and $R^{20e}$, when present, is hydrogen, and $R^{20c}$, when present, is selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20a}$, $R^{20b}$, $R^{20d}$ and $R^{20e}$, when present, is hydrogen, and $R^{20c}$, when present, is selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20a}$, $R^{20b}$, $R^{20d}$, and $R^{20e}$, when present, is hydrogen, and $R^{20c}$, when present, is selected from —F, —Cl, —N$_3$, and methyl.

In a further aspect, each of $R^{20a}$, $R^{20c}$, $R^{20d}$, and $R^{20e}$, when present, is hydrogen, and $R^{20b}$, when present, is selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{20a}$, $R^{20c}$, $R^{20d}$, and $R^{20e}$, when present, is hydrogen, and $R^{20b}$, when present, is selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{20a}$, $R^{20c}$, $R^{20d}$, and $R^{20e}$, when present, is hydrogen, and $R^{20b}$, when present, is selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20a}$, $R^{20c}$, $R^{20d}$, and $R^{20e}$, when present, is hydrogen, and $R^{20b}$, when present, is selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20a}$, $R^{20c}$, $R^{20d}$, and $R^{20e}$, when present, is hydrogen, and $R^{20b}$, when present, is selected from —F, —Cl, —N$_3$, and methyl.

In a further aspect, each of $R^{20b}$, $R^{20c}$, $R^{20d}$, and $R^{20e}$, when present, is hydrogen, and $R^{20a}$, when present, is selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{20b}$, $R^{20c}$, $R^{20d}$, and $R^{20e}$, when present, is hydrogen, and $R^{20a}$, when present, is selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{20b}$, $R^{20c}$, $R^{20d}$, and $R^{20e}$, when present, is hydrogen, and $R^{20a}$, when present, is selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{20b}$, $R^{20c}$, $R^{20d}$, and $R^{20e}$, when present, is hydrogen, and $R^{20a}$, when present, is selected from —F, —Cl, —OH, —CN, —N$_3$, —NH$_2$, methyl, —CF$_3$, —OCH$_3$, —OCF$_3$, —NHCH$_3$, and —N(CH$_3$)$_2$. In a still further aspect, each of $R^{20b}$, $R^{20c}$, $R^{20d}$, and $R^{20e}$, when present, is hydrogen, and $R^{20a}$, when present, is selected from —F, —Cl, —N$_3$, and methyl.

In a further aspect, each of $R^{20a}$, $R^{20b}$, $R^{20c}$, $R^{20d}$, and $R^{20e}$, when present, is hydrogen.

i. $R^{30A}$, $R^{30B}$, and $R^{30C}$ Groups

In one aspect, each of $R^{30a}$, $R^{30b}$, and $R^{30c}$, when present, are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a further aspect, each of $R^{30a}$, $R^{30b}$, and $R^{30c}$, when present, are independently selected from hydrogen, —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In a still further aspect, each of $R^{30a}$, $R^{30b}$, and $R^{30c}$, when present, are independently selected from hydrogen, —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In yet a further aspect, each of $R^{30a}$, $R^{30b}$, and $R^{30c}$, when present, are independently selected from hydrogen, —F, —Cl, —OH, —CN, —N$_3$, —NH$_2$, methyl, —CF$_3$, —OCH$_3$, —OCF$_3$, —NHCH$_3$, and —N(CH$_3$)$_2$. In an even further aspect, each of $R^{30a}$, $R^{30b}$, and $R^{30c}$, when present, are independently selected from hydrogen, —F, —Cl, —N$_3$, and methyl.

In a further aspect, $R^{30a}$, when present, is hydrogen and each of $R^{30b}$ and $R^{30c}$, when present, is independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, $R^{30a}$, when present, is hydrogen and each of $R^{30b}$ and $R^{30c}$, when present, is independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, $R^{30a}$, when present, is hydrogen and each of $R^{30b}$ and $R^{30c}$, when present, is independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, $R^{30a}$, when present, is hydrogen and each of $R^{30b}$ and $R^{30c}$, when present, is independently selected from —F, —Cl, —N$_3$, and methyl.

In a further aspect, $R^{30b}$, when present, is hydrogen and each of $R^{30a}$ and $R^{30c}$, when present, is independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, $R^{30b}$, when present, is hydrogen and each of $R^{30a}$ and $R^{30c}$, when present, is independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, $R^{30b}$, when present, is hydrogen and each of $R^{30a}$ and $R^{30c}$, when present, is independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, $R^{30b}$, when present, is hydrogen and each of $R^{30a}$ and $R^{30c}$, when present, is independently selected from —F, —Cl, —N$_3$, and methyl.

In a further aspect, $R^{30c}$, when present, is hydrogen and each of $R^{30a}$ and $R^{30b}$, when present, is independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, $R^{30c}$, when present, is hydrogen and each of $R^{30a}$ and $R^{30b}$, when present, is independently selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, $R^{30c}$, when present, is hydrogen and each of $R^{30a}$ and $R^{30b}$, when present, is independently selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, $R^{30c}$, when present, is hydrogen and each of $R^{30a}$ and $R^{30b}$, when present, is independently selected from —F, —Cl, —N$_3$, and methyl.

In a further aspect, each of $R^{30a}$ and $R^{30b}$, when present, are hydrogen and $R^{30c}$, when present, is selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{30a}$ and $R^{30b}$, when present, are hydrogen and $R^{30c}$, when present, is selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{30a}$ and $R^{30b}$, when present, are hydrogen and $R^{30c}$, when present, is selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{30a}$ and $R^{30b}$, when present, are hydrogen and $R^{30c}$, when present, is selected from —F, —Cl, —N$_3$, and methyl.

In a further aspect, each of $R^{30a}$ and $R^{30c}$, when present, are hydrogen and $R^{30b}$, when present, is selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{30a}$ and $R^{30c}$, when present, are hydrogen and $R^{30b}$, when present, is selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{30a}$ and $R^{30c}$, when present, are hydrogen and $R^{30b}$, when present, is selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{30a}$ and $R^{30c}$, when present, are hydrogen and $R^{30b}$, when present, is selected from —F, —Cl, —N$_3$, and methyl.

In a further aspect, each of $R^{30b}$ and $R^{30c}$, when present, are hydrogen and $R^{30a}$, when present, is selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, each of $R^{30b}$ and $R^{30c}$, when present, are hydrogen and $R^{30a}$, when present, is selected from —F, —Cl, —OH, —CN, —N$_3$, —NH$_2$, methyl, ethyl, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —OCH$_3$, —OCH$_2$CH$_3$, —OCH$_2$F, —OCHF$_2$, —OCF$_3$, —NHCH$_3$, and —N(CH$_3$)$_2$. In yet a further aspect, each of $R^{30b}$ and $R^{30c}$, when present, are hydrogen and $R^{30a}$, when present, is selected from —F, —Cl, —OH, —CN, —N$_3$, —NH$_2$, methyl, —CH$_2$F, —CH$_2$Cl, —CHF$_2$, —CF$_3$, —CHCl$_2$, —CCl$_3$, —OCH$_3$, —OCH$_2$F, —OCHF$_2$, —OCF$_3$, —NHCH$_3$, and —N(CH$_3$)$_2$. In an even further aspect, each of $R^{30b}$ and $R^{30c}$, when present, are hydrogen and $R^{30a}$, when present, is selected —F, —Cl, —N$_3$, and methyl.

In a further aspect, each of $R^{30a}$, $R^{30b}$, and $R^{30c}$, when present, is hydrogen.

j. AR$^1$ Groups

In one aspect, Ar$^1$ is selected from aryl and heteroaryl, and Ar$^1$ is substituted with 0, 1, 2, or 3 groups independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a further aspect, $Ar^1$ is selected from aryl and heteroaryl, and $Ar^1$ is substituted with 0, 1, 2, or 3 groups independently selected from halogen, —OH, —CN, —$N_3$, —$NH_2$, C1-C2 alkyl, C1-C2 alkoxy, C1-C2 monohaloalkyl, C1-C2 polyhaloalkyl, C1-C2 alkylamino, and C1-C2 dialkylamino. In a still further aspect, $Ar^1$ is selected from aryl and heteroaryl, and $Ar^1$ is unsubstituted.

In a further aspect, $Ar^1$ is selected from aryl and heteroaryl, and $Ar^1$ is substituted with 0, 1, 2, or 3 groups independently selected from —F, —Cl, hydroxyl, cyano, —$N_3$, —$NH_2$, methyl, ethyl, propyl, isopropyl, tert-butyl, sec-butyl, isobutyl, tert-butyl, —$OCH_3$, —$OCH_2CH_3$, —$O(CH_2)_2CH_3$, —$OCH(CH_3)_2$, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$N(CH_3)CH(CH_3)_2$, and —$N(CH_2CH_3)_2$.

In a further aspect, $Ar^1$ is aryl, and substituted with 0, 1, 2, or 3 groups independently selected from —F, —Cl, hydroxyl, cyano, —$N_3$, —$NH_2$, methyl, ethyl, propyl, isopropyl, tert-butyl, sec-butyl, isobutyl, tert-butyl, —$OCH_3$, —$OCH_2CH_3$, —$O(CH_2)_2CH_3$, —$OCH(CH_3)_2$, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$N(CH_3)CH(CH_3)_2$, and —$N(CH_2CH_3)_2$.

In a further aspect, $Ar^1$ is heteroaryl, and substituted with 0, 1, 2, or 3 groups independently selected from —F, —Cl, hydroxyl, cyano, —$N_3$, —$NH_2$, methyl, ethyl, propyl, isopropyl, tert-butyl, sec-butyl, isobutyl, tert-butyl, —$OCH_3$, —$OCH_2CH_3$, —$O(CH_2)_2CH_3$, —$OCH(CH_3)_2$, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$N(CH_3)CH(CH_3)_2$, and —$N(CH_2CH_3)_2$.

In a further aspect, $Ar^1$ is phenyl, and substituted with 0, 1, 2, or 3 groups independently selected from —F, —Cl, hydroxyl, cyano, —$N_3$, —$NH_2$, methyl, ethyl, propyl, isopropyl, tert-butyl, sec-butyl, isobutyl, tert-butyl, —$OCH_3$, —$OCH_2CH_3$, —$O(CH_2)_2CH_3$, —$OCH(CH_3)_2$, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$N(CH_3)CH(CH_3)_2$, and —$N(CH_2CH_3)_2$.

In a further aspect, $Ar^1$ is thiophenyl, and substituted with 0, 1, 2, or 3 groups independently selected from —F, —Cl, hydroxyl, cyano, —$N_3$, —$NH_2$, methyl, ethyl, propyl, isopropyl, tert-butyl, sec-butyl, isobutyl, tert-butyl, —$OCH_3$, —$OCH_2CH_3$, —$O(CH_2)_2CH_3$, —$OCH(CH_3)_2$, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$N(CH_3)CH(CH_3)_2$, and —$N(CH_2CH_3)_2$.

In a further aspect, $Ar^1$ is selected from aryl and heteroaryl, and $Ar^1$ is substituted with 0, 1, 2, or 3 groups independently selected from —F, —Cl, hydroxyl, cyano, —$N_3$, —$NH_2$, methyl, ethyl, propyl, isopropyl, —$OCH_3$, —$OCH_2CH_3$, —$OCH(CH_3)_2$, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NHCH_3$, —$NHCH_2CH_3$, —$N(CH_3)_2$, —$N(CH_3)CH_2CH_3$, and —$N(CH_3)CH(CH_3)_2$. In a still further aspect, $Ar^1$ is selected from aryl and heteroaryl, and $Ar^1$ is substituted with 0, 1, 2, or 3 groups independently selected from —F, —Cl, —$N_3$, hydroxyl, —$NH_2$, methyl, ethyl, —$OCH_3$, —$OCH_2CH_3$, —$CH_2F$, —$CH_2Cl$, —$CHF_2$, —$CF_3$, —$CH_2Cl$, —$CHCl_2$, —$CCl_3$, —$NHCH_3$, and —$N(CH_3)_2$. In yet a further aspect, $Ar^1$ is selected from aryl and heteroaryl, and $Ar^1$ is substituted with 0, 1, 2, or 3 groups independently selected from —F, —Cl, —$N_3$, methyl, —$OCH_3$, —$CF_3$, —$CCl_3$, —$NHCH_3$, and —$N(CH_3)_2$.

In a further aspect, $Ar^1$ is aryl, and substituted with 0, 1, 2, or 3 groups independently selected from —F, —Cl, hydroxyl, cyano, —$N_3$, —$NH_2$, methyl, ethyl, propyl, isopropyl, —$OCH_3$, —$OCH_2CH_3$, —$OCH(CH_3)_2$, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NHCH_3$, —$NHCH_2CH_3$, —$N(CH_3)_2$, —$N(CH_3)CH_2CH_3$, and —$N(CH_3)CH(CH_3)_2$. In a still further aspect, $Ar^1$ is aryl, and substituted with 0, 1, 2, or 3 groups independently selected from —F, —Cl, —$N_3$, hydroxyl, —$NH_2$, methyl, ethyl, —$OCH_3$, —$OCH_2CH_3$, —$CH_2F$, —$CH_2Cl$, —$CHF_2$, —$CF_3$, —$CH_2Cl$, —$CHCl_2$, —$CCl_3$, —$NHCH_3$, and —$N(CH_3)_2$. In yet a further aspect, $Ar^1$ is aryl, and substituted with 0, 1, 2, or 3 groups independently selected from —F, —Cl, —$N_3$, methyl, —$OCH_3$, —$CF_3$, —$CCl_3$, —$NHCH_3$, and —$N(CH_3)_2$.

In a further aspect, $Ar^1$ is heteroaryl, and substituted with 0, 1, 2, or 3 groups independently selected from —F, —Cl, hydroxyl, cyano, —$N_3$, —$NH_2$, methyl, ethyl, propyl, isopropyl, —$OCH_3$, —$OCH_2CH_3$, —$OCH(CH_3)_2$, —$CH_2F$, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^1$ is heteroaryl, and substituted with 0, 1, 2, or 3 groups independently selected from —F, —Cl, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^1$ is heteroaryl, and substituted with 0, 1, 2, or 3 groups independently selected from —F, —Cl, —N$_3$, methyl, —OCH$_3$, —CF$_3$, —CCl$_3$, —NHCH$_3$, and —N(CH$_3$)$_2$.

In a further aspect, Ar$^1$ is phenyl, and substituted with 0, 1, 2, or 3 groups independently selected from —F, —Cl, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^1$ is phenyl, and substituted with 0, 1, 2, or 3 groups independently selected from —F, —Cl, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^1$ is phenyl, and substituted with 0, 1, 2, or 3 groups independently selected from —F, —Cl, —N$_3$, methyl, —OCH$_3$, —CF$_3$, —CCl$_3$, —NHCH$_3$, and —N(CH$_3$)$_2$.

In a further aspect, Ar$^1$ is thiophenyl, and substituted with 0, 1, 2, or 3 groups independently selected from —F, —Cl, hydroxyl, cyano, —N$_3$, —NH$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^1$ is thiophenyl, and substituted with 0, 1, 2, or 3 groups independently selected from —F, —Cl, —N$_3$, hydroxyl, —NH$_2$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^1$ is thiophenyl, and substituted with 0, 1, 2, or 3 groups independently selected from —F, —Cl, —N$_3$, methyl, —OCH$_3$, —CF$_3$, —NHCH$_3$, and —N(CH$_3$)$_2$.

In a further aspect, Ar$^1$ is selected from aryl and heteroaryl, and Ar$^1$ is substituted with 0, 1, or 2 groups independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^1$ is selected from aryl and heteroaryl, and Ar$^1$ is substituted with 0 or 1 substituent selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In yet a further aspect, Ar$^1$ is selected from aryl and heteroaryl, and Ar$^1$ is monosubstituted with a substituent selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino.

In a further aspect, Ar$^1$ is selected from aryl and heteroaryl, and Ar$^1$ is substituted with 0, 1, or 2 groups independently selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino. In a still further aspect, Ar$^1$ is selected from aryl and heteroaryl, and Ar$^1$ is substituted with 0 or 1 substituent selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^1$ is selected from aryl and heteroaryl, and Ar$^1$ is monosubstituted with a substituent selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino.

In a further aspect, Ar$^1$ is aryl and substituted with 0, 1, 2, or 3 groups independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^1$ is aryl and substituted with 0, 1, 2, or 3 groups independently selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^1$ is unsubstituted aryl.

In a further aspect, Ar$^1$ is heteroaryl and substituted with 0, 1, 2, or 3 groups independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^1$ is heteroaryl and substituted with 0, 1, 2, or 3 groups independently selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^1$ is unsubstituted heteroaryl.

In a further aspect, Ar$^1$ is phenyl and substituted with 0, 1, 2, or 3 groups independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^1$ is phenyl and substituted with 0, 1, 2, or 3 groups independently selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^1$ is unsubstituted phenyl.

In a further aspect, Ar$^1$ is thiophenyl and substituted with 0, 1, 2, or 3 groups independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^1$ is thiophenyl and substituted with 0, 1, 2, or 3 groups independently selected from halogen, —OH, —CN, —N$_3$, —NH$_2$, C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^1$ is unsubstituted thiophenyl.

k. AR$^2$ Groups

In one aspect, wherein Ar$^2$, when present, is selected from aryl and heteroaryl, and Ar$^2$ is substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a further aspect, Ar$^2$, when present, is selected from aryl and heteroaryl, and Ar$^2$ is substituted with 0, 1, 2, or 3 groups independently selected from halogen, —OH, —CN, —N$_3$, —NH$_2$, —C(O) (C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In a still further aspect, Ar$^2$, when present, is selected from aryl and heteroaryl, and Ar$^2$ is unsubstituted.

In a further aspect, Ar$^2$, when present, is selected from aryl and heteroaryl, and Ar$^2$ is substituted with 0, 1, 2, or 3 groups independently selected from —F, —Cl, —Br, —I, hydroxyl, cyano, —N$_3$, —NH$_2$, —C(O)CH$_3$, —C(O)CH$_2$CH$_3$, —C(O)(CH$_2$)$_2$CH$_3$, —C(O)CH(CH$_3$)$_2$, —C(O)(CH$_2$)$_3$CH$_3$, —C(O)CH(CH$_2$CH$_3$)CH$_3$, —C(O)CH$_2$CH(CH$_3$)$_2$, —C(O)C(CH$_3$)$_3$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Ar$^2$, when present, is aryl and substituted with 0, 1, 2, or 3 groups independently selected from —F, —Cl, —Br, —I, hydroxyl, cyano, —N$_3$, —NH$_2$, —C(O)CH$_3$, —C(O)CH$_2$CH$_3$, —C(O)(CH$_2$)$_2$CH$_3$, —C(O)CH(CH$_3$)$_2$, —C(O)(CH$_2$)$_3$CH$_3$, —C(O)CH(CH$_2$CH$_3$)CH$_3$, —C(O)CH$_2$CH(CH$_3$)$_2$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Ar$^2$, when present, is heteroaryl and substituted with 0, 1, 2, or 3 groups independently selected from —F, —Cl, —Br, —I, hydroxyl, cyano, —N$_3$, —NH$_2$, —C(O)CH$_3$, —C(O)CH$_2$CH$_3$, —C(O)(CH$_2$)$_2$CH$_3$, —C(O)CH(CH$_3$)$_2$, —C(O)(CH$_2$)$_3$CH$_3$, —C(O)CH(CH$_2$CH$_3$)CH$_3$, —C(O)CH$_2$CH(CH$_3$)$_2$, methyl, ethyl, propyl, isopropyl, ten-butyl, sec-butyl, isobutyl, ten-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Ar$^2$, when present, is selected from phenyl, pyridinyl, oxazolyl, and isoxazolyl, and Ar$^2$ is substituted with 0, 1, 2, or 3 groups independently selected from —F, —Cl, —Br, —I, hydroxyl, cyano, —N$_3$, —NH$_2$, —C(O)CH$_3$, —C(O)CH$_2$CH$_3$, —C(O)(CH$_2$)$_2$CH$_3$, —C(O)CH(CH$_3$)$_2$, —C(O)(CH$_2$)$_3$CH$_3$, —C(O)CH(CH$_2$CH$_3$)CH$_3$, —C(O)CH$_2$CH(CH$_3$)$_2$, methyl, ethyl, propyl, isopropyl, ten-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Ar$^2$, when present, is selected from aryl and heteroaryl, and Ar$^2$ is substituted with 0, 1, 2, or 3 groups independently selected from —F, —Cl, —Br, —I, hydroxyl, cyano, —N$_3$, —NH$_2$, —C(O)CH$_3$, —C(O)CH$_2$CH$_3$, —C(O)(CH$_2$)$_2$CH$_3$, —C(O)CH(CH$_3$)$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^2$, when present, is selected from aryl and heteroaryl, and Ar$^2$ is substituted with 0, 1, 2, or 3 groups independently selected from —F, —Cl, —Br, —I, —N$_3$, hydroxyl, —NH$_2$, —C(O)CH$_3$, —C(O)CH$_2$CH$_3$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^2$, when present, is selected from aryl and heteroaryl, and Ar$^2$ is substituted with 0, 1, 2, or 3 groups independently selected from —F, —Cl, —Br, —I, —N$_3$, hydroxyl, —C(O)CH$_3$, methyl, —OCH$_3$, —CF$_3$, —CCl$_3$, —NHCH$_3$, and —N(CH$_3$)$_2$.

In a further aspect, Ar$^2$, when present, is aryl and substituted with 0, 1, 2, or 3 groups independently selected from —F, —Cl, —Br, —I, hydroxyl, cyano, —N$_3$, —NH$_2$, —C(O)CH$_3$, —C(O)CH$_2$CH$_3$, —C(O)(CH$_2$)$_2$CH$_3$, —C(O)CH(CH$_3$)$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^2$, when present, is aryl and substituted with 0, 1, 2, or 3 groups independently selected from —F, —Cl, —Br, —I, —N$_3$, hydroxyl, —NH$_2$, —C(O)CH$_3$, —C(O)CH$_2$CH$_3$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^2$, when present, is aryl and substituted with 0, 1, 2, or 3 groups independently selected from —F, —Cl, —Br, —I, —N$_3$, hydroxyl, —C(O)CH$_3$, methyl, —OCH$_3$, —CF$_3$, —CCl$_3$, —NHCH$_3$, and —N(CH$_3$)$_2$.

In a further aspect, Ar$^2$, when present, is heteroaryl and substituted with 0, 1, 2, or 3 groups independently selected from —F, —Cl, —Br, —I, hydroxyl, cyano, —N$_3$, —NH$_2$, —C(O)CH$_3$, —C(O)CH$_2$CH$_3$, —C(O)(CH$_2$)$_2$CH$_3$, —C(O)CH(CH$_3$)$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^2$, when present, is heteroaryl and substituted with 0, 1, 2, or 3 groups independently selected from —F, —Cl, —Br, —I, —N$_3$, hydroxyl, —NH$_2$, —C(O)CH$_3$, —C(O)CH$_2$CH$_3$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^2$, when present, is heteroaryl and substituted with 0, 1, 2, or 3 groups independently selected from —F, —Cl, —N$_3$, hydroxyl, —C(O)CH$_3$, methyl, —OCH$_3$, —CF$_3$, —CCl$_3$, —NHCH$_3$, and —N(CH$_3$)$_2$.

In a further aspect, Ar$^2$, when present, is selected from phenyl, pyridinyl, oxazolyl, and isoxazolyl, and Ar$^2$ is substituted with 0, 1, 2, or 3 groups independently selected from —F, —Cl, —Br, —I, hydroxyl, cyano, —N$_3$, —NH$_2$, —C(O)CH$_3$, —C(O)CH$_2$CH$_3$, —C(O)(CH$_2$)$_2$CH$_3$, —C(O)CH(CH$_3$)$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^2$, when present, is selected from phenyl, pyridinyl, oxazolyl, and isoxazolyl, and Ar$^2$ is substituted with 0, 1, 2, or 3 groups independently selected from —F, —Cl, —Br, —I, —N$_3$, hydroxyl, —NH$_2$, —C(O)CH$_3$, —C(O)CH$_2$CH$_3$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^2$, when present, is selected from phenyl, pyridinyl, oxazolyl, and isoxazolyl, and Ar$^2$ is substituted with 0, 1, 2, or 3 groups independently selected from —F, —Cl, —Br, —I, —N$_3$, hydroxyl, —C(O)CH$_3$, methyl, —OCH$_3$, —CF$_3$, —CCl$_3$, —NHCH$_3$, and —N(CH$_3$)$_2$.

In a further aspect, Ar$^2$, when present, is selected from aryl and heteroaryl, and Ar$^2$ is substituted with 0, 1, or 2 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^2$, when present, is selected from aryl and heteroaryl, and Ar$^2$ is substituted with 0 or 1 substituent selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In yet a further aspect, Ar$^2$, when present, is selected from aryl and heteroaryl, and Ar$^2$ is monosubstituted with a substituent selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino.

In a further aspect, Ar$^2$, when present, is selected from aryl and heteroaryl, and Ar$^2$ is substituted with 0, 1, or 2 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In a still further aspect, Ar$^2$, when present, is selected from aryl and heteroaryl, and Ar$^2$ is substituted with 0 or 1 substituent selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^2$, when present, is selected from aryl and heteroaryl, and Ar$^2$ is monosubstituted with a substituent selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino.

In a further aspect, Ar$^2$, when present, is aryl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^2$, when present, is aryl and substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^2$, when present, is unsubstituted aryl.

In a further aspect, Ar$^2$, when present, is heteroaryl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^2$, when present, is heteroaryl and substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^2$, when present, is unsubstituted heteroaryl.

In a further aspect, Ar$^2$, when present, is selected from phenyl, pyridinyl, oxazolyl, and isoxazolyl, and Ar$^2$ is substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^2$, when present, is selected from phenyl, pyridinyl, oxazolyl, and isoxazolyl, and Ar$^2$ is substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^2$, when present, is selected from phenyl, pyridinyl, oxazolyl, and isoxazolyl, and Ar$^2$ is unsubstituted.

In a further aspect, Ar$^2$, when present, is phenyl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^2$, when present, is phenyl and substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^2$, when present, is unsubstituted phenyl.

In a further aspect, Ar$^2$, when present, is pyridinyl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^2$, when present, is pyridinyl and substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^2$, when present, is unsubstituted pyridinyl.

In a further aspect, Ar$^2$, when present, is oxazolyl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^2$, when present, is oxazolyl and substituted with 0, 1, 2, or 3 groups independently selected from halogen, —OH, —CN, —N₃, —NH₂, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar², when present, is unsubstituted oxazolyl.

In a further aspect, Ar², when present, is isoxazolyl and substituted with 0, 1, 2, or 3 groups independently selected from halogen, —OH, —CN, —N₃, —NH₂, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar², when present, is isoxazolyl and substituted with 0, 1, 2, or 3 groups independently selected from halogen, —OH, —CN, —N₃, —NH₂, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar², when present, is unsubstituted isoxazolyl.

1. AR³ Groups

In one aspect, Ar³, when present, is selected from aryl and heteroaryl, and Ar³ is substituted with 0, 1, 2, or 3 groups independently selected from halogen, —OH, —CN, —N₃, —NH₂, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino, provided that when R² is hydrogen then Ar³, when present, cannot be a structure selected from:

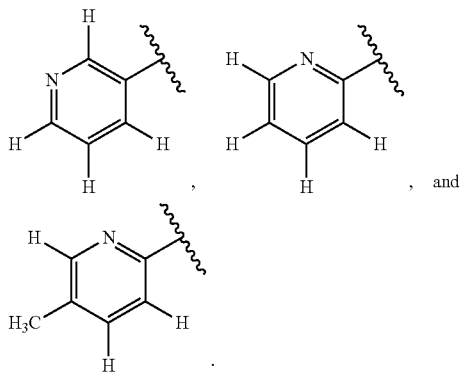

In a further aspect, Ar³, when present, is selected from aryl and heteroaryl, and Ar³ is substituted with 0, 1, 2, or 3 groups independently selected from halogen, —OH, —CN, —N₃, —NH₂, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In a still further aspect, Ar³, when present, is selected from aryl and heteroaryl, and Ar³ is unsubstituted.

In one aspect, Ar³, when present, is selected from aryl and heteroaryl, and Ar³ is substituted with 0, 1, 2, or 3 groups independently selected from halogen, —OH, —CN, —N₃, —NH₂, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a further aspect, Ar³, when present, is selected from aryl and heteroaryl, and Ar³ is substituted with 0, 1, 2, or 3 groups independently selected from halogen, —OH, —CN, —N₃, —NH₂, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In a still further aspect, Ar³, when present, is selected from aryl and heteroaryl and Ar³ is unsubstituted.

In a further aspect, R² is hydrogen and Ar³, when present, is not pyridinyl. In a further aspect, the pyridinyl is substituted. In a still further aspect, the pyridinyl is unsubstituted.

In a further aspect, Ar³, when present, is selected from aryl and heteroaryl, and Ar³ is substituted with 0, 1, 2, or 3 groups independently selected from —F, —Cl, —Br, —I, hydroxyl, cyano, —N₃, —NH₂, —C(O)CH₃, —OC(O) CH₂CH₃, —C(O)(CH₂)₂CH₃, —C(O)CH(CH₃)₂, —C(O) (CH₂)₃CH₃, —C(O)CH(CH₂CH₃)CH₃, —C(O)CH₂CH (CH₃)₂, —C(O)C(CH₃)₃, methyl, ethyl, propyl, isopropyl, tert-butyl, sec-butyl, isobutyl, tert-butyl, —OCH₃, —OCH₂CH₃, —O(CH₂)₂CH₃, —OCH(CH₃)₂, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂ CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂ CCl₃, —(CH₂)₂CHBr₂, —(CH₂)₂CBr₃, —(CH₂)₂CHI₂, —(CH₂)₂CI₃, —NHCH₃, —NHCH₂CH₃, —NH(CH₂)₂ CH₃, —NHCH(CH₃)₂, —NH(CH₂)₃CH₃, —NH(CH₂)₄C H₃, —N(CH₃)₂, —N(CH₃)CH₂CH₃, —N(CH₃)(CH₂)₂ CH₃, —N(CH₃)CH(CH₃)₂, and —N(CH₂CH₃)₂.

In a further aspect, Ar³, when present, is aryl and substituted with 0, 1, 2, or 3 groups independently selected from —F, —Cl, —Br, —I, hydroxyl, cyano, —N₃, —NH₂, —C(O)CH₃, —C(O)CH₂CH₃, —C(O)(CH₂)₂CH₃, —C(O) CH(CH₃)₂, —C(O)(CH₂)₃CH₃, —C(O)CH(CH₂CH₃)CH₃, —C(O)CH₂CH(CH₃)₂, —C(O)C(CH₃)₃, methyl, ethyl, propyl, isopropyl, tert-butyl, sec-butyl, isobutyl, tert-butyl, —OCH₃, —OCH₂CH₃, —O(CH₂)₂CH₃, —OCH(CH₃)₂, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂ CHI₂, —(CH₂)₂CI₃, —NHCH₃, —NHCH₂CH₃, —NH (CH₂)₂CH₃, —NHCH(CH₃)₂, —NH(CH₂)₃CH₃, —NH (CH₂)₄CH₃, —N(CH₃)₂, —N(CH₃)CH₂CH₃, —N(CH₃) (CH₂)₂CH₃, —N(CH₃)CH(CH₃)₂, and —N(CH₂CH₃)₂.

In a further aspect, Ar³, when present, is heteroaryl and substituted with 0, 1, 2, or 3 groups independently selected from —F, —Cl, —Br, —I, hydroxyl, cyano, —N₃, —NH₂, —C(O)CH₃, —C(O)CH₂CH₃, —C(O)(CH₂)₂CH₃, —C(O) CH(CH₃)₂, —C(O)(CH₂)₃CH₃, —C(O)CH(CH₂CH₃)CH₃, —C(O)CH₂CH(CH₃)₂, —C(O)C(CH₃)₃, methyl, ethyl, propyl, isopropyl, tert-butyl, sec-butyl, isobutyl, tert-butyl, —OCH₃, —OCH₂CH₃, —O(CH₂)₂CH₃, —OCH(CH₃)₂, —CH₂F, —CH₂Cl, —CH₂Br, —CH₂I, —CH₂CH₂F, —CH₂CH₂Cl, —CH₂CH₂Br, —CH₂CH₂I, —(CH₂)₂CH₂F, —(CH₂)₂CH₂Cl, —(CH₂)₂CH₂Br, —(CH₂)₂CH₂I, —CHF₂, —CF₃, —CHCl₂, —CCl₃, —CHBr₂, —CBr₃, —CHI₂, —CI₃, —CH₂CHF₂, —CH₂CF₃, —CH₂CHCl₂, —CH₂CCl₃, —CH₂CHBr₂, —CH₂CBr₃, —CH₂CHI₂, —CH₂CI₃, —(CH₂)₂CHF₂, —(CH₂)₂CF₃, —(CH₂)₂CHCl₂, —(CH₂)₂CCl₃, —(CH₂)₂CHBr₂, —(CH₂)₂CBr₃, —(CH₂)₂ CHI₂, —(CH₂)₂CI₃, —NHCH₃, —NHCH₂CH₃, —NH (CH₂)₂CH₃, —NHCH(CH₃)₂, —NH(CH₂)₃CH₃, —NH (CH₂)₄CH₃, —N(CH₃)₂, —N(CH₃)CH₂CH₃, —N(CH₃) (CH₂)₂CH₃, —N(CH₃)CH(CH₃)₂, and —N(CH₂CH₃)₂.

In a further aspect, Ar³, when present, is selected from phenyl, oxazolyl, isoxazolyl, pyrimidinyl, indolyl, and 1H-pyrrolo[2,3-b]pyridinyl, and Ar³ is substituted with 0, 1, 2, or 3 groups independently selected from —F, —Cl, —Br, —I, hydroxyl, cyano, —N₃, —NH₂, —C(O)CH₃, —C(O) CH₂CH₃, —C(O)(CH₂)₂CH₃, —C(O)CH(CH₃)₂, —C(O)

$(CH_2)_3CH_3$, —$C(O)CH(CH_2CH_3)CH_3$, —$C(O)CH_2CH(CH_3)_2$, —$C(O)C(CH_3)_3$, methyl, ethyl, propyl, isopropyl, tert-butyl, sec-butyl, isobutyl, tert-butyl, —$OCH_3$, —$OCH_2CH_3$, —$O(CH_2)_2CH_3$, —$OCH(CH_3)_2$, —$CH_2F$, —$CH_2Cl$, —$CH_2Br$, —$CH_2I$, —$CH_2CH_2F$, —$CH_2CH_2Cl$, —$CH_2CH_2Br$, —$CH_2CH_2I$, —$(CH_2)_2CH_2F$, —$(CH_2)_2CH_2Cl$, —$(CH_2)_2CH_2Br$, —$(CH_2)_2CH_2I$, —$CHF_2$, —$CF_3$, —$CHCl_2$, —$CCl_3$, —$CHBr_2$, —$CBr_3$, —$CHI_2$, —$CI_3$, —$CH_2CHF_2$, —$CH_2CF_3$, —$CH_2CHCl_2$, —$CH_2CCl_3$, —$CH_2CHBr_2$, —$CH_2CBr_3$, —$CH_2CHI_2$, —$CH_2CI_3$, —$(CH_2)_2CHF_2$, —$(CH_2)_2CF_3$, —$(CH_2)_2CHCl_2$, —$(CH_2)_2CCl_3$, —$(CH_2)_2CHBr_2$, —$(CH_2)_2CBr_3$, —$(CH_2)_2CHI_2$, —$(CH_2)_2CI_3$, —$NHCH_3$, —$NHCH_2CH_3$, —$NH(CH_2)_2CH_3$, —$NHCH(CH_3)_2$, —$NH(CH_2)_3CH_3$, —$NH(CH_2)_4CH_3$, —$N(CH_3)_2$, —$N(CH_3)CH_2CH_3$, —$N(CH_3)(CH_2)_2CH_3$, —$N(CH_3)CH(CH_3)_2$, and —$N(CH_2CH_3)_2$.

In a further aspect, $Ar^3$, when present, is selected from aryl and heteroaryl, and $Ar^3$ is substituted with 0, 1, 2, or 3 groups independently selected from —F, —Cl, —Br, —I, hydroxyl, cyano, —$N_3$, —$NH_2$, —$C(O)CH_3$, —$C(O)CH_2CH_3$, —$C(O)(CH_2)_2CH_3$, —$C(O)CH(CH_3)_2$, methyl, ethyl, propyl, isopropyl, —$OCH_3$, —$OCH_2CH_3$, —$OCH(CH_3)_2$, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NHCH_3$, —$NHCH_2CH_3$, —$N(CH_3)_2$, —$N(CH_3)CH_2CH_3$, and —$N(CH_3)CH(CH_3)_2$. In a still further aspect, $Ar^3$, when present, is selected from aryl and heteroaryl, and $Ar^3$ is substituted with 0, 1, 2, or 3 groups independently selected from —F, —Cl, —Br, —I, —$N_3$, hydroxyl, —$NH_2$, —$C(O)CH_3$, —$C(O)CH_2CH_3$, methyl, ethyl, —$OCH_3$, —$OCH_2CH_3$, —$CH_2F$, —$CH_2Cl$, —$CHF_2$, —$CF_3$, —$CH_2Cl$, —$CHCl_2$, —$CCl_3$, —$NHCH_3$, and —$N(CH_3)_2$. In yet a further aspect, $Ar^3$, when present, is selected from aryl and heteroaryl, and $Ar^3$ is substituted with 0, 1, 2, or 3 groups independently selected from —F, —Cl, —Br, —I, —$N_3$, hydroxyl, —$C(O)CH_3$, methyl, —$OCH_3$, —$CF_3$, —$CCl_3$, —$NHCH_3$, and —$N(CH_3)_2$.

In a further aspect, $Ar^3$, when present, is aryl and substituted with 0, 1, 2, or 3 groups independently selected from —F, —Cl, —Br, —I, hydroxyl, cyano, —$N_3$, —$NH_2$, —$C(O)CH_3$, —$C(O)CH_2CH_3$, —$C(O)(CH_2)_2CH_3$, —$C(O)CH(CH_3)_2$, methyl, ethyl, propyl, isopropyl, —$OCH_3$, —$OCH_2CH_3$, —$OCH(CH_3)_2$, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NHCH_3$, —$NHCH_2CH_3$, —$N(CH_3)_2$, —$N(CH_3)CH_2CH_3$, and —$N(CH_3)CH(CH_3)_2$. In a still further aspect, $Ar^3$, when present, is aryl and substituted with 0, 1, 2, or 3 groups independently selected from —F, —Cl, —Br, —I, —$N_3$, hydroxyl, —$NH_2$, —$C(O)CH_3$, —$C(O)CH_2CH_3$, methyl, ethyl, —$OCH_3$, —$OCH_2CH_3$, —$CH_2F$, —$CH_2Cl$, —$CHF_2$, —$CF_3$, —$CH_2Cl$, —$CHCl_2$, —$CCl_3$, —$NHCH_3$, and —$N(CH_3)_2$. In yet a further aspect, $Ar^3$, when present, is aryl and substituted with 0, 1, 2, or 3 groups independently selected from —F, —Cl, —Br, —I, —$N_3$, hydroxyl, —$C(O)CH_3$, methyl, —$OCH_3$, —$CF_3$, —$CCl_3$, —$NHCH_3$, and —$N(CH_3)_2$.

In a further aspect, $Ar^3$, when present, is heteroaryl and substituted with 0, 1, 2, or 3 groups independently selected from —F, —Cl, —Br, —I, hydroxyl, cyano, —$N_3$, —$NH_2$, —$C(O)CH_3$, —$C(O)CH_2CH_3$, —$C(O)(CH_2)_2CH_3$, —$C(O)CH(CH_3)_2$, methyl, ethyl, propyl, isopropyl, —$OCH_3$, —$OCH_2CH_3$, —$OCH(CH_3)_2$, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NHCH_3$, —$NHCH_2CH_3$, —$N(CH_3)_2$, —$N(CH_3)CH_2CH_3$, and —$N(CH_3)CH(CH_3)_2$. In a still further aspect, $Ar^3$, when present, is heteroaryl and substituted with 0, 1, 2, or 3 groups independently selected from —F, —Cl, —Br, —I, —$N_3$, hydroxyl, —$NH_2$, —$C(O)CH_3$, —$C(O)CH_2CH_3$, methyl, ethyl, —$OCH_3$, —$OCH_2CH_3$, —$CH_2F$, —$CH_2Cl$, —$CHF_2$, —$CF_3$, —$CH_2Cl$, —$CHCl_2$, —$CCl_3$, —$NHCH_3$, and —$N(CH_3)_2$. In yet a further aspect, $Ar^3$, when present, is heteroaryl and substituted with 0, 1, 2, or 3 groups independently selected from —F, —Cl, —Br, —I, —$N_3$, —$C(O)CH_3$, methyl, hydroxyl, —$OCH_3$, —$CF_3$, —$CCl_3$, —$NHCH_3$, and —$N(CH_3)_2$.

In a further aspect, $Ar^3$, when present, is selected from phenyl, oxazolyl, isoxazolyl, pyrimidinyl, indolyl, and 1H-pyrrolo[2,3-b]pyridinyl, and $Ar^3$ is substituted with 0, 1, 2, or 3 groups independently selected from —F, —Cl, —Br, —I, hydroxyl, cyano, —$N_3$, —$NH_2$, —$C(O)CH_3$, —$C(O)CH_2CH_3$, —$C(O)(CH_2)_2CH_3$, —$C(O)CH(CH_3)_2$, methyl, ethyl, propyl, isopropyl, —$OCH_3$, —$OCH_2CH_3$, —$OCH(CH_3)_2$, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NHCH_3$, —$NHCH_2CH_3$, —$N(CH_3)_2$, —$N(CH_3)CH_2CH_3$, and —$N(CH_3)CH(CH_3)_2$. In a still further aspect, $Ar^3$, when present, is selected from phenyl, oxazolyl, isoxazolyl, pyrimidinyl, indolyl, and 1H-pyrrolo[2,3-b]pyridinyl, and $Ar^3$ is substituted with 0, 1, 2, or 3 groups independently selected from —F, —Cl, —Br, —I, —$N_3$, hydroxyl, —$NH_2$, —$C(O)CH_3$, —$C(O)CH_2CH_3$, methyl, ethyl, —$OCH_3$, —$OCH_2CH_3$, —$CH_2F$, —$CH_2Cl$, —$CHF_2$, —$CF_3$, —$CH_2Cl$, —$CHCl_2$, —$CCl_3$, —$NHCH_3$, and —$N(CH_3)_2$. In yet a further aspect, $Ar^3$, when present, is selected from phenyl, oxazolyl, isoxazolyl, pyrimidinyl, indolyl, and 1H-pyrrolo[2,3-b]pyridinyl, and $Ar^3$ is substituted with 0, 1, 2, or 3 groups independently selected from —F, —Cl, —Br, —I, —$N_3$, hydroxyl, —$C(O)CH_3$, methyl, —$OCH_3$, —$CF_3$, —$CCl_3$, —$NHCH_3$, and —$N(CH_3)_2$.

In a further aspect, $Ar^3$, when present, is selected from aryl and heteroaryl, and $Ar^3$ is substituted with 0, 1, or 2 groups independently selected from halogen, —OH, —CN, —$N_3$, —$NH_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, $Ar^3$, when present, is selected from aryl and heteroaryl, and $Ar^3$ is substituted with 0 or 1 substituent selected from halogen, —OH, —CN, —$N_3$, —$NH_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In yet a further aspect, $Ar^3$, when present, is selected from aryl and heteroaryl, and $Ar^3$ is monosubstituted with a substituent selected from halogen, —OH, —CN, —$N_3$, —$NH_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino.

In a further aspect, $Ar^3$, when present, is selected from aryl and heteroaryl, and $Ar^3$ is substituted with 0, 1, or 2 groups independently selected from halogen, —OH, —CN, —$N_3$, —$NH_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In a still further aspect, $Ar^3$, when present, is selected from aryl and heteroaryl, and $Ar^3$ is substituted with 0 or 1 substituent selected from halogen, —OH, —CN, —$N_3$, —$NH_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, $Ar^3$, when present, is selected from aryl and heteroaryl, and $Ar^3$ is monosubstituted with a substituent selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino.

In a further aspect, Ar$^3$, when present, is aryl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^3$, when present, is aryl and substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^3$, when present, is unsubstituted aryl.

In a further aspect, Ar$^3$, when present, is heteroaryl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^3$, when present, is heteroaryl and substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^3$, when present, is unsubstituted heteroaryl.

In a further aspect, Ar$^3$, when present, is selected from phenyl, oxazolyl, isoxazolyl, pyrimidinyl, indolyl, and 1H-pyrrolo[2,3-b]pyridinyl, and Ar$^3$ is substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^3$, when present, is selected from phenyl, oxazolyl, isoxazolyl, pyrimidinyl, indolyl, and 1H-pyrrolo[2,3-b]pyridinyl, and Ar$^3$ is substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^3$, when present, is selected from phenyl, oxazolyl, isoxazolyl, pyrimidinyl, indolyl, and 1H-pyrrolo[2,3-b]pyridinyl, and Ar$^3$ is unsubstituted.

In a further aspect, Ar$^3$, when present, is phenyl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^3$, when present, is phenyl and substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^3$, when present, is unsubstituted phenyl.

In a further aspect, Ar$^3$, when present, is oxazolyl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^3$, when present, is oxazolyl and substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^3$, when present, is unsubstituted oxazolyl.

In a further aspect, Ar$^3$, when present, is isoxazolyl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^3$, when present, is isoxazolyl and substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^3$, when present, is unsubstituted isoxazolyl.

In a further aspect, Ar$^3$, when present, is pyrimidinyl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^3$, when present, is pyrimidinyl and substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^3$, when present, is unsubstituted pyrimidinyl.

In a further aspect, Ar$^3$, when present, is indolyl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^3$, when present, is indolyl and substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^3$, when present, is unsubstituted indolyl.

In a further aspect, Ar$^3$, when present, is 1H-pyrrolo[2,3-b]pyridinyl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^3$, when present, is 1H-pyrrolo[2,3-b]pyridinyl and substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^3$, when present, is unsubstituted 1H-pyrrolo[2,3-b]pyridinyl.

m. AR$^4$ Groups

In one aspect, Ar$^4$, when present, is selected from aryl and heteroaryl, and Ar$^4$ is substituted with 0, 1, 2, or 3 groups independently selected from halogen, —OH, —CN, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino, provided that when R$^2$ is hydrogen then Ar$^4$, when present, cannot be a structure selected from:

-continued

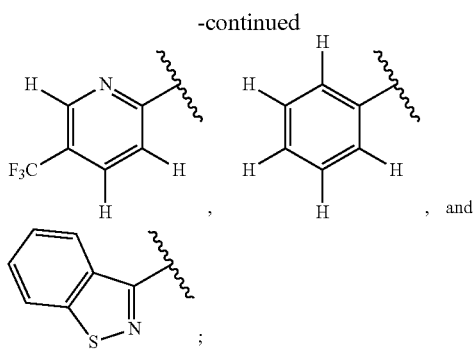

and In a further aspect, Ar⁴, when present, is selected from aryl and heteroaryl, and Ar⁴ is substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In a still further aspect, Ar⁴, when present, is selected from aryl and heteroaryl, and Ar⁴ is unsubstituted.

In one aspect, Ar⁴, when present, is selected from aryl and heteroaryl, and Ar⁴ is substituted with 0, 1, 2, or 3 groups independently selected from halogen, —OH, —CN, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a further aspect, Ar⁴, when present, is selected from aryl and heteroaryl, and Ar⁴ is substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In a still further aspect, Ar⁴, when present, is selected from aryl and heteroaryl, and Ar⁴ is unsubstituted.

In a further aspect, R² is hydrogen and Ar⁴, when present, is not pyridinyl. In a further aspect, the pyridinyl is substituted. In a still further aspect, the pyridinyl is unsubstituted.

In a further aspect, R² is hydrogen and Ar⁴, when present, is not phenyl. In a further aspect, the phenyl is substituted. In a still further aspect, the phenyl is unsubstituted.

In a further aspect, R² is hydrogen and Ar⁴, when present, is not benzo[d]isothiazole. In a further aspect, the benzo[d]isothiazole is substituted. In a still further aspect, the benzo[d]isothiazole is unsubstituted.

In a further aspect, Ar⁴, when present, is selected from aryl and heteroaryl, and Ar⁴ is substituted with 0, 1, 2, or 3 groups independently selected from —F, —Cl, —Br, —I, hydroxyl, cyano, —N$_3$, —NH$_2$, —C(O)CH$_3$, —C(O)CH$_2$CH$_3$, —C(O)(CH$_2$)$_2$CH$_3$, —C(O)CH(CH$_3$)$_2$, —C(O)(CH$_2$)$_3$CH$_3$, —C(O)CH(CH$_2$CH$_3$)CH$_3$, —C(O)CH$_2$CH(CH$_3$)$_2$, —C(O)C(CH$_3$)$_3$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Ar⁴, when present, is aryl and substituted with 0, 1, 2, or 3 groups independently selected from —F, —Cl, —Br, —I, hydroxyl, cyano, —N$_3$, —NH$_2$, —C(O)CH$_3$, —C(O)CH$_2$CH$_3$, —C(O)(CH$_2$)$_2$CH$_3$, —C(O)CH(CH$_3$)$_2$, —C(O)(CH$_2$)$_3$CH$_3$, —C(O)CH(CH$_2$CH$_3$)CH$_3$, —C(O)CH$_2$CH(CH$_3$)$_2$, —C(O)C(CH$_3$)$_3$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Ar⁴, when present, is heteroaryl and substituted with 0, 1, 2, or 3 groups independently selected from —F, —Cl, —Br, —I, hydroxyl, cyano, —N$_3$, —NH$_2$, —C(O)CH$_3$, —C(O)CH$_2$CH$_3$, —C(O)(CH$_2$)$_2$CH$_3$, —C(O)CH(CH$_3$)$_2$, —C(O)(CH$_2$)$_3$CH$_3$, —C(O)CH(CH$_2$CH$_3$)CH$_3$, —C(O)CH$_2$CH(CH$_3$)$_2$, —C(O)C(CH$_3$)$_3$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Ar⁴, when present, is selected from phenyl, oxazolyl, isoxazolyl, pyrimidinyl, indolyl, and 1H-pyrrolo[2,3-b]pyridinyl, and Ar⁴ is substituted with 0, 1, 2, or 3 groups independently selected from —F, —Cl, —Br, —I, hydroxyl, cyano, —N$_3$, —NH$_2$, —C(O)CH$_3$, —C(O)CH$_2$CH$_3$, —C(O)(CH$_2$)$_2$CH$_3$, —C(O)CH(CH$_3$)$_2$, —C(O)(CH$_2$)$_3$CH$_3$, —C(O)CH(CH$_2$CH$_3$)CH$_3$, —C(O)CH$_2$CH(CH$_3$)$_2$, —C(O)C(CH$_3$)$_3$, methyl, ethyl, propyl, isopropyl, tert-butyl, sec-butyl, isobutyl, tert-butyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$Br, —CH$_2$I, —CH$_2$CH$_2$F, —CH$_2$CH$_2$Cl, —CH$_2$CH$_2$Br, —CH$_2$CH$_2$I, —(CH$_2$)$_2$CH$_2$F, —(CH$_2$)$_2$CH$_2$Cl, —(CH$_2$)$_2$CH$_2$Br, —(CH$_2$)$_2$CH$_2$I, —CHF$_2$, —CF$_3$, —CHCl$_2$, —CCl$_3$, —CHBr$_2$, —CBr$_3$, —CHI$_2$, —CI$_3$, —CH$_2$CHF$_2$, —CH$_2$CF$_3$, —CH$_2$CHCl$_2$, —CH$_2$CCl$_3$, —CH$_2$CHBr$_2$, —CH$_2$CBr$_3$, —CH$_2$CHI$_2$, —CH$_2$CI$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —(CH$_2$)$_2$CHBr$_2$, —(CH$_2$)$_2$CBr$_3$, —(CH$_2$)$_2$CHI$_2$, —(CH$_2$)$_2$CI$_3$, —NHCH$_3$, —NHCH$_2$CH$_3$, —NH(CH$_2$)$_2$CH$_3$, —NHCH(CH$_3$)$_2$, —NH(CH$_2$)$_3$CH$_3$, —NH(CH$_2$)$_4$CH$_3$, —N(CH$_3$)$_2$, —N(CH$_3$)CH$_2$CH$_3$, —N(CH$_3$)(CH$_2$)$_2$CH$_3$, —N(CH$_3$)CH(CH$_3$)$_2$, and —N(CH$_2$CH$_3$)$_2$.

In a further aspect, Ar⁴, when present, is selected from aryl and heteroaryl, and Ar⁴ is substituted with 0, 1, 2, or 3 groups independently selected from —F, —Cl, —Br, —I, hydroxyl, cyano, —N$_3$, —NH$_2$, —C(O)CH$_3$, —C(O)CH$_2$CH$_3$, —C(O)(CH$_2$)$_2$CH$_3$, —C(O)CH(CH$_3$)$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^4$, when present, is selected from aryl and heteroaryl, and Ar$^4$ is substituted with 0, 1, 2, or 3 groups independently selected from —F, —Cl, —Br, —I, —N$_3$, hydroxyl, —NH$_2$, —C(O)CH$_3$, —C(O)CH$_2$CH$_3$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^4$, when present, is selected from aryl and heteroaryl, and Ar$^4$ is substituted with 0, 1, 2, or 3 groups independently selected from —F, —Cl, —Br, —I, —N$_3$, hydroxyl, —C(O)CH$_3$, methyl, —OCH$_3$, —CF$_3$, —CCl$_3$, —NHCH$_3$, and —N(CH$_3$)$_2$.

In a further aspect, Ar$^4$, when present, is aryl and substituted with 0, 1, 2, or 3 groups independently selected from —F, —Cl, —Br, —I, hydroxyl, cyano, —N$_3$, —NH$_2$, —C(O)CH$_3$, —C(O)CH$_2$CH$_3$, —C(O)(CH$_2$)$_2$CH$_3$, —C(O)CH(CH$_3$)$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^4$, when present, is aryl and substituted with 0, 1, 2, or 3 groups independently selected from —F, —Cl, —Br, —I, —N$_3$, hydroxyl, —NH$_2$, —C(O)CH$_3$, —C(O)CH$_2$CH$_3$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^4$, when present, is aryl and substituted with 0, 1, 2, or 3 groups independently selected from —F, —Cl, —Br, —I, —N$_3$, hydroxyl, —C(O)CH$_3$, methyl, —OCH$_3$, —CF$_3$, —CCl$_3$, —NHCH$_3$, and —N(CH$_3$)$_2$.

In a further aspect, Ar$^4$, when present, is heteroaryl and substituted with 0, 1, 2, or 3 groups independently selected from —F, —Cl, —Br, —I, hydroxyl, cyano, —N$_3$, —NH$_2$, —C(O)CH$_3$, —C(O)CH$_2$CH$_3$, —C(O)(CH$_2$)$_2$CH$_3$, —C(O)CH(CH$_3$)$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^4$, when present, is heteroaryl and substituted with 0, 1, 2, or 3 groups independently selected from —F, —Cl, —Br, —I, —N$_3$, hydroxyl, —NH$_2$, —C(O)CH$_3$, —C(O)CH$_2$CH$_3$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^4$, when present, is heteroaryl and substituted with 0, 1, 2, or 3 groups independently selected from —F, —Cl, —Br, —I, —N$_3$, hydroxyl, —C(O)CH$_3$, methyl, —OCH$_3$, —CF$_3$, —CCl$_3$, —NHCH$_3$, and —N(CH$_3$)$_2$.

In a further aspect, Ar$^4$, when present, is selected from phenyl, oxazolyl, isoxazolyl, pyrimidinyl, indolyl, and 1H-pyrrolo[2,3-b]pyridinyl, and Ar$^4$ is substituted with 0, 1, 2, or 3 groups independently selected from —F, —Cl, —Br, —I, hydroxyl, cyano, —N$_3$, —NH$_2$, —C(O)CH$_3$, —C(O)CH$_2$CH$_3$, —C(O)(CH$_2$)$_2$CH$_3$, —C(O)CH(CH$_3$)$_2$, methyl, ethyl, propyl, isopropyl, —OCH$_3$, —OCH$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_3$)CH(CH$_3$)$_2$. In a still further aspect, Ar$^4$, when present, is selected from phenyl, oxazolyl, isoxazolyl, pyrimidinyl, indolyl, and 1H-pyrrolo[2,3-b]pyridinyl, and Ar$^4$ is substituted with 0, 1, 2, or 3 groups independently selected from —F, —Cl, —Br, —I, —N$_3$, hydroxyl, —NH$_2$, —C(O)CH$_3$, —C(O)CH$_2$CH$_3$, methyl, ethyl, —OCH$_3$, —OCH$_2$CH$_3$, —CH$_2$F, —CH$_2$Cl, —CHF$_2$, —CF$_3$, —CH$_2$Cl, —CHCl$_2$, —CCl$_3$, —NHCH$_3$, and —N(CH$_3$)$_2$. In yet a further aspect, Ar$^4$, when present, is selected from phenyl, oxazolyl, isoxazolyl, pyrimidinyl, indolyl, and 1H-pyrrolo[2,3-b]pyridinyl, and Ar$^4$ is substituted with 0, 1, 2, or 3 groups independently selected from —F, —Cl, —Br, —I, —N$_3$, hydroxyl, —C(O)CH$_3$, methyl, —OCH$_3$, —CF$_3$, —CCl$_3$, —NHCH$_3$, and —N(CH$_3$)$_2$.

In a further aspect, Ar$^4$, when present, is selected from aryl and heteroaryl, and Ar$^4$ is substituted with 0, 1, or 2 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^4$, when present, is selected from aryl and heteroaryl, and Ar$^4$ is substituted with 0 or 1 substituent selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In yet a further aspect, Ar$^4$, when present, is selected from aryl and heteroaryl, and Ar$^4$ is monosubstituted with a substituent selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino.

In a further aspect, Ar$^4$, when present, is selected from aryl and heteroaryl, and Ar$^4$ is substituted with 0, 1, or 2 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In a still further aspect, Ar$^4$, when present, is selected from aryl and heteroaryl, and Ar$^4$ is substituted with 0 or 1 substituent selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^4$, when present, is selected from aryl and heteroaryl, and Ar$^4$ is monosubstituted with a substituent selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino.

In a further aspect, Ar$^4$, when present, is aryl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^4$, when present, is aryl and substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^4$, when present, is unsubstituted aryl.

In a further aspect, Ar$^4$, when present, is heteroaryl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^4$, when present, is heteroaryl and substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^4$, when present, is unsubstituted heteroaryl.

In a further aspect, Ar$^4$, when present, is selected from phenyl, oxazolyl, isoxazolyl, pyrimidinyl, indolyl, and 1H-pyrrolo[2,3-b]pyridinyl, and Ar$^4$ is substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^4$, when present, is selected from phenyl, oxazolyl, isoxazolyl, pyrimidinyl, indolyl, and 1H-pyrrolo[2,3-b]pyridinyl, and Ar$^4$ is substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^4$, when present, is selected from phenyl, oxazolyl, isoxazolyl, pyrimidinyl, indolyl, and 1H-pyrrolo[2,3-b]pyridinyl, and Ar$^4$ is unsubstituted.

In a further aspect, Ar$^4$, when present, is phenyl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^4$, when present, is phenyl and substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^4$, when present, is unsubstituted phenyl.

In a further aspect, Ar$^4$, when present, is oxazolyl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^4$, when present, is oxazolyl and substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^4$, when present, is unsubstituted oxazolyl.

In a further aspect, Ar$^4$, when present, is isoxazolyl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^4$, when present, is isoxazolyl and substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^4$, when present, is unsubstituted isoxazolyl.

In a further aspect, Ar$^4$, when present, is pyrimidinyl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^4$, when present, is pyrimidinyl and substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^4$, when present, is unsubstituted pyrimidinyl.

In a further aspect, Ar$^4$, when present, is indolyl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^4$, when present, is indolyl and substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^4$, when present, is unsubstituted indolyl.

In a further aspect, Ar$^4$, when present, is 1H-pyrrolo[2,3-b]pyridinyl and substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino. In a still further aspect, Ar$^4$, when present, is 1H-pyrrolo[2,3-b]pyridinyl and substituted with 0, 1, 2, or 3 groups independently selected from halogen, —OH, —CN, —N$_3$, —NH$_2$, —C(O)(C1-C2 alkyl), C1-C2 alkyl, C1-C2 alkoxy, C1-C2 monohaloalkyl, C1-C2 polyhaloalkyl, C1-C2 alkylamino, and C1-C2 dialkylamino. In yet a further aspect, Ar$^4$, when present, is unsubstituted 1H-pyrrolo[2,3-b]pyridinyl.

2. Compound Examples

In one aspect, a compound is selected from:

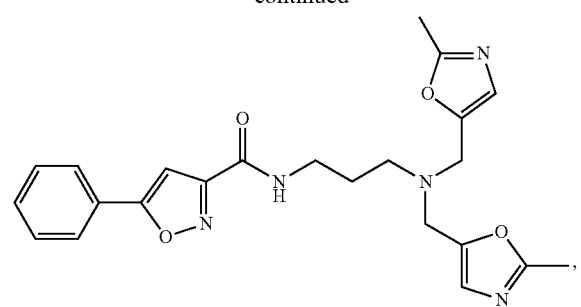
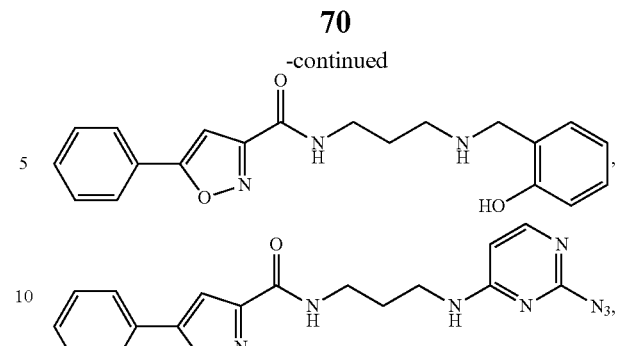

-continued
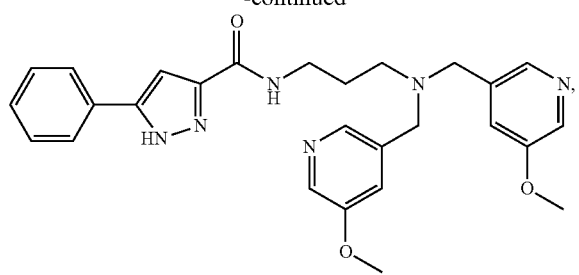
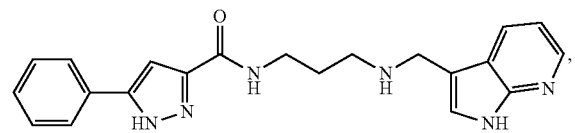
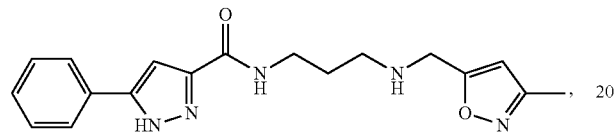
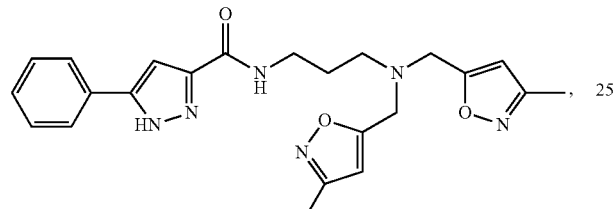
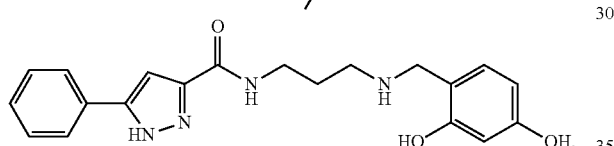
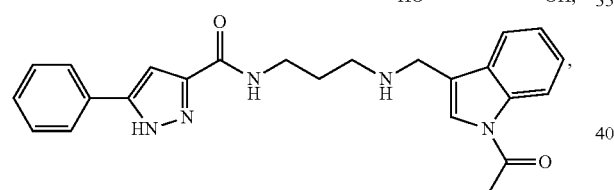
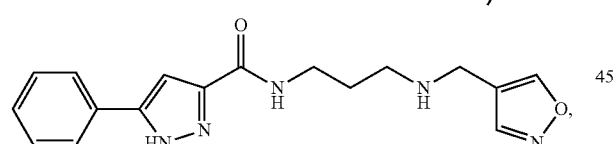
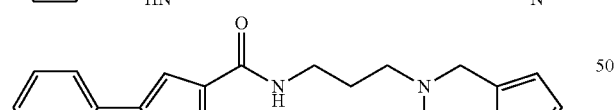
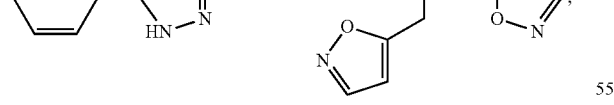
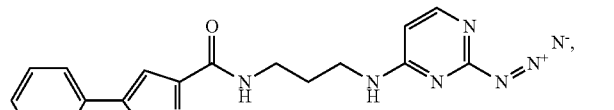
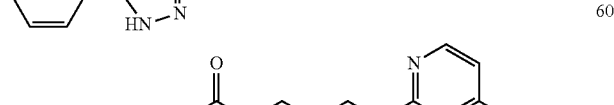
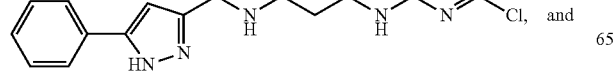
-continued
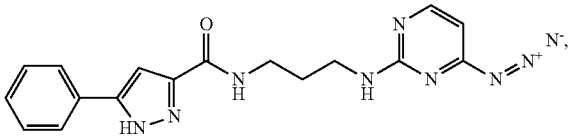
or a pharmaceutically acceptable salt thereof.
In a further aspect, a compound is selected from:
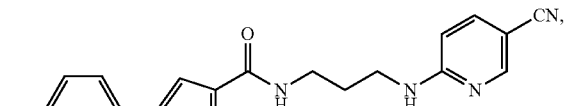
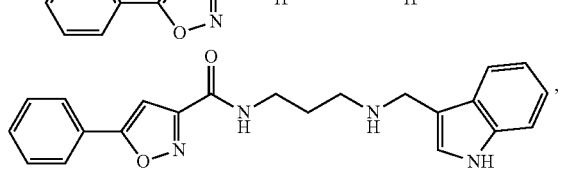
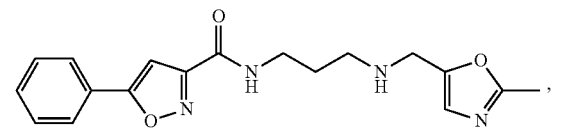
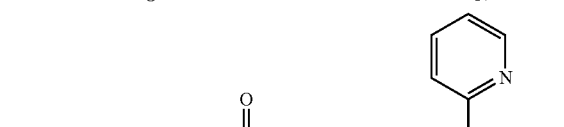
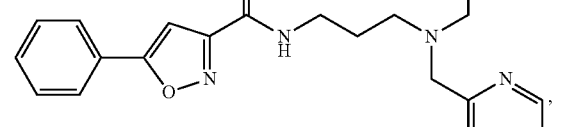
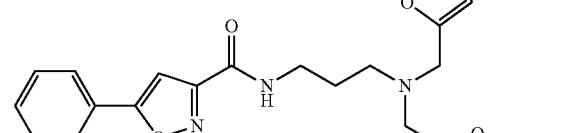
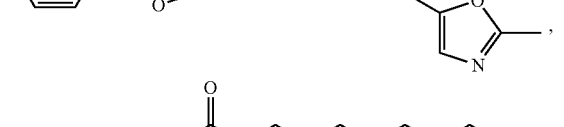
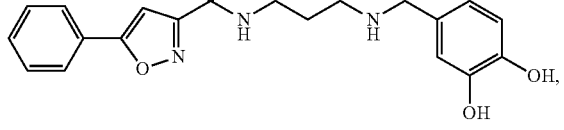
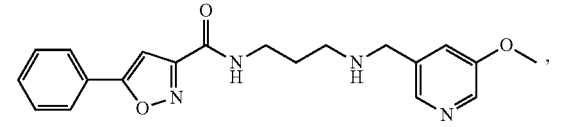
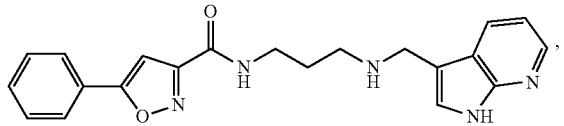

-continued
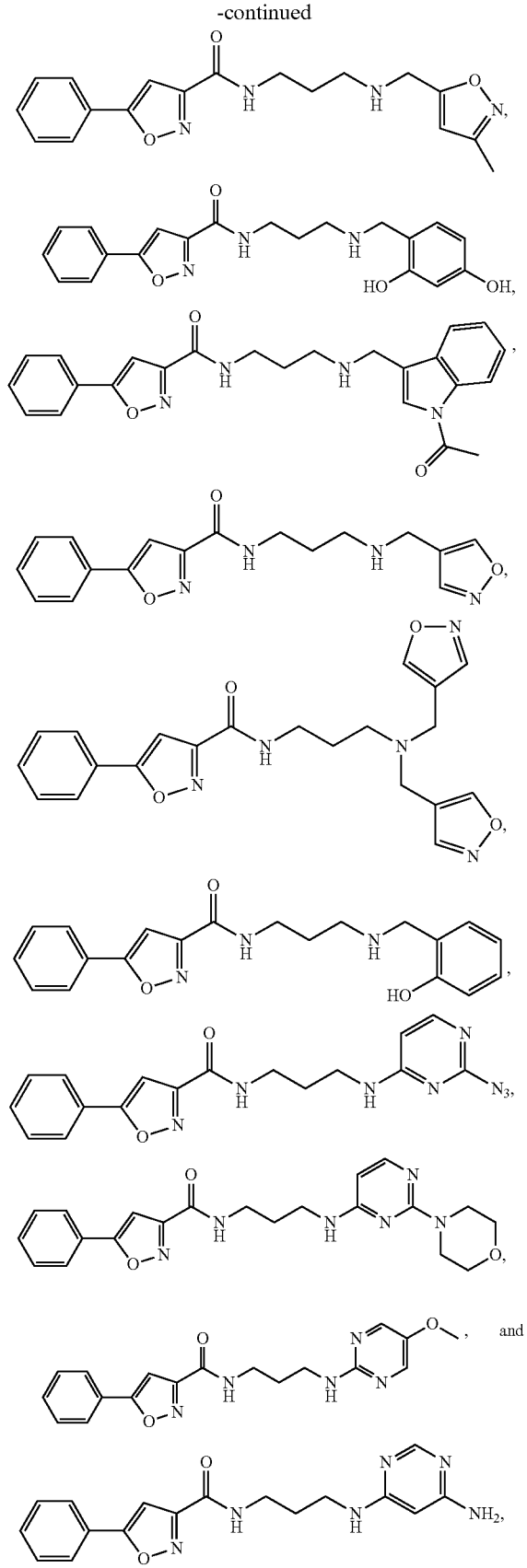
or a pharmaceutically acceptable salt thereof.
In a still further aspect, a compound is selected from:
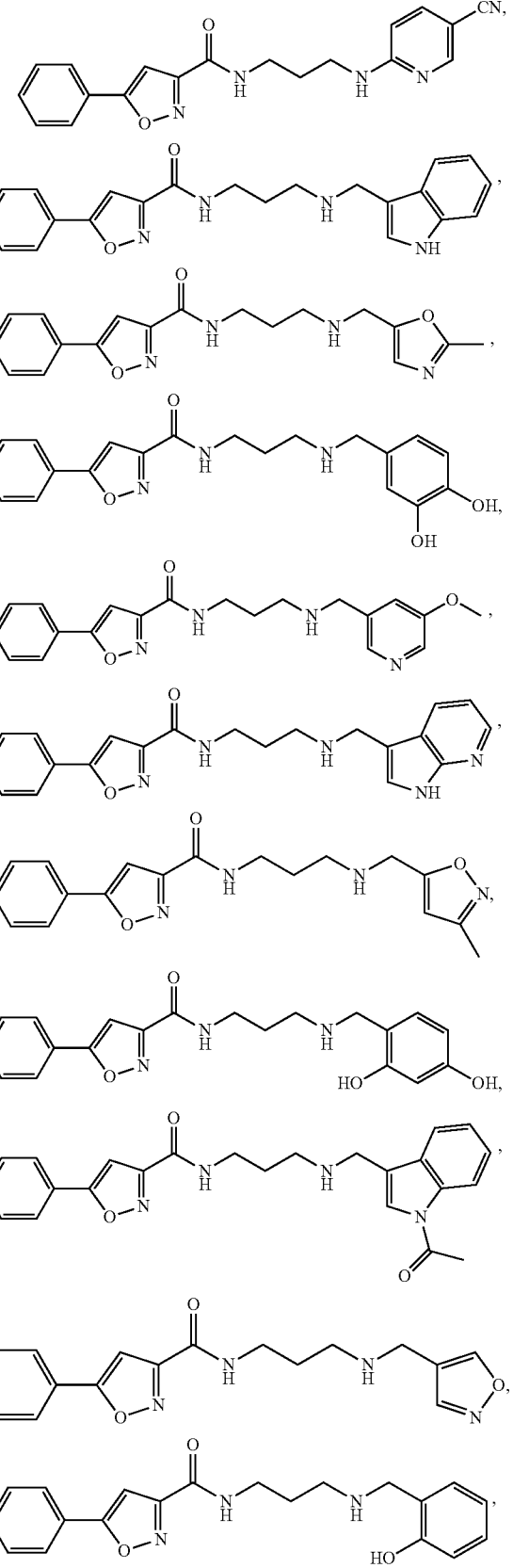

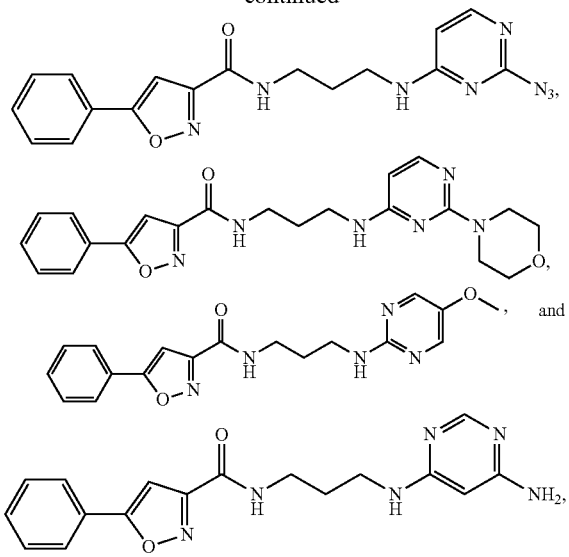
or a pharmaceutically acceptable salt thereof.
In yet a further aspect, a compound is selected from:
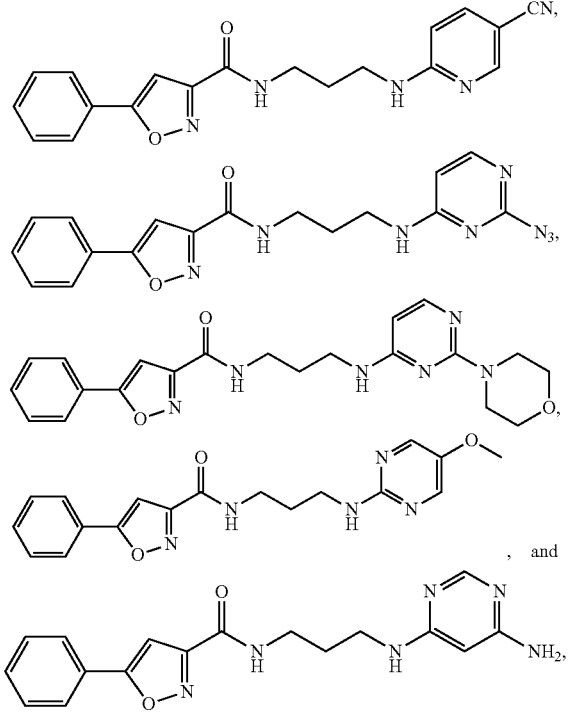
or a pharmaceutically acceptable salt thereof.
In an even further aspect, a compound is selected from:
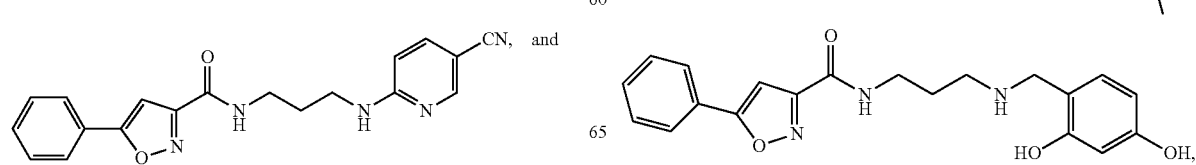
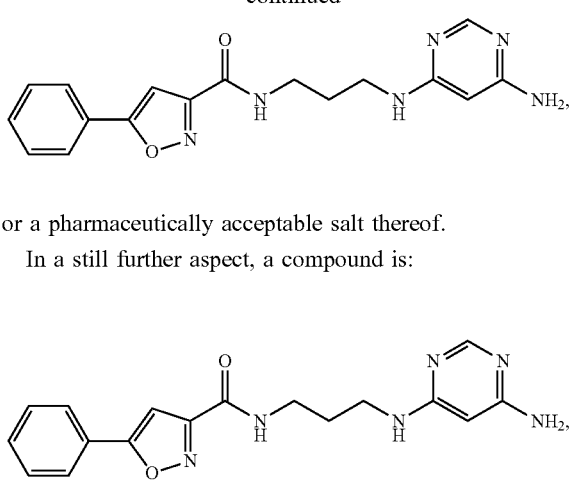
or a pharmaceutically acceptable salt thereof.
In a still further aspect, a compound is:
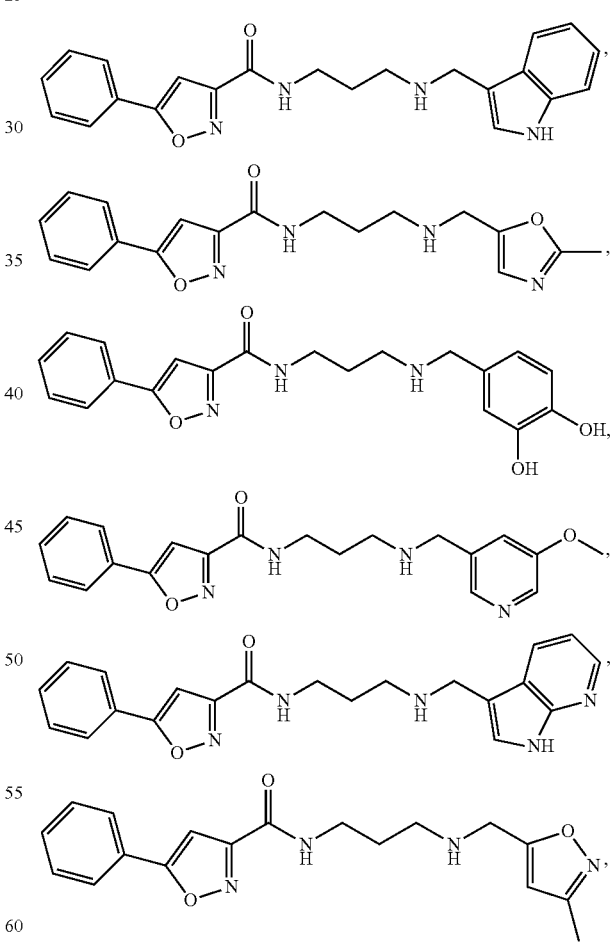

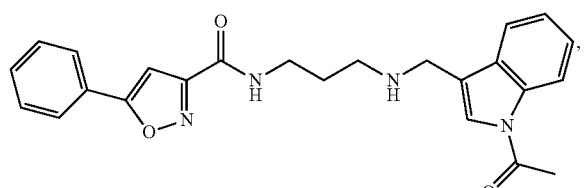

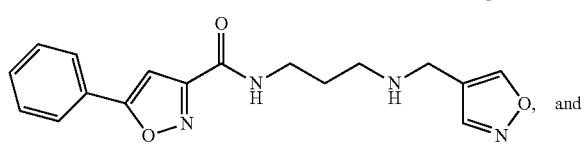, and

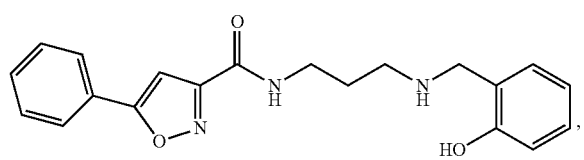

or a pharmaceutically acceptable salt thereof.

In a still further aspect, a compound is:

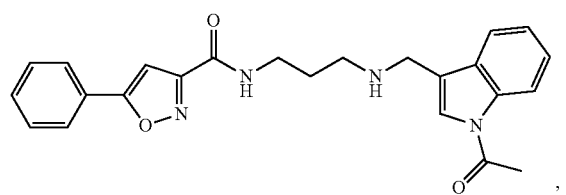 [SMILES: CC(=O)n1cc(CNCCCNC(=O)c2cc(-c3ccccc3)on2)c2ccccc21]

or a pharmaceutically acceptable salt thereof.

In a further aspect, a compound is selected from:

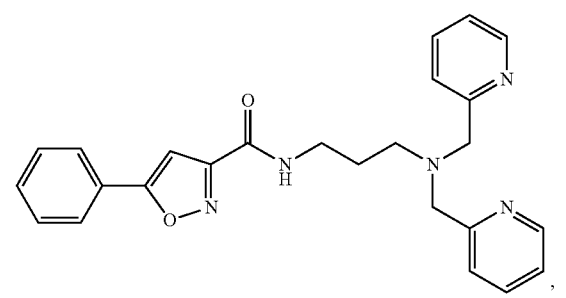 [SMILES: O=C(NCCCN(Cc1ccccn1)Cc1ccccn1)c1cc(-c2ccccc2)on1]

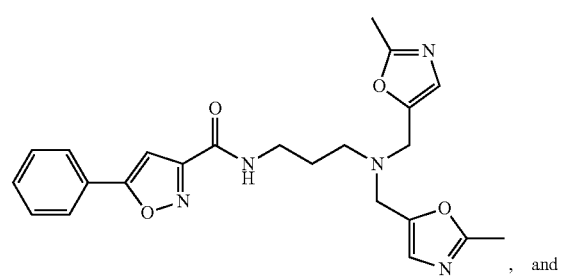, and

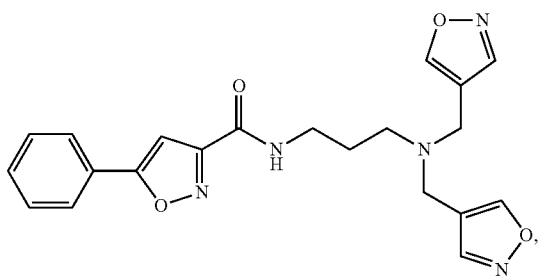

or a pharmaceutically acceptable salt thereof.

In a still further aspect, a compound is:

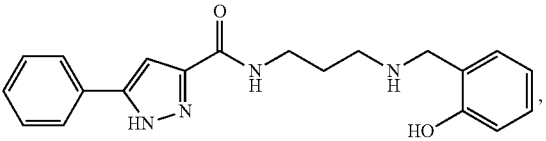

or a pharmaceutically acceptable salt thereof.

In a further aspect, a compound is selected from:

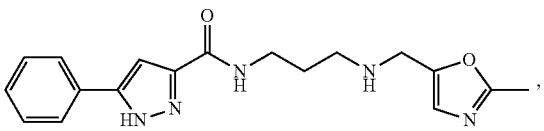

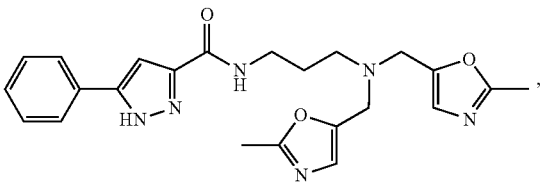

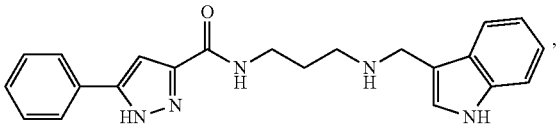

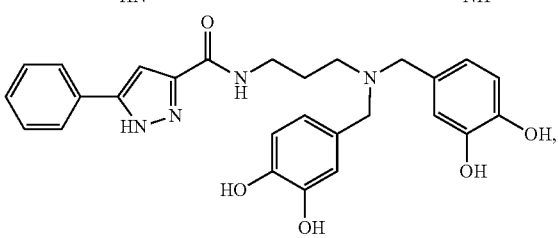

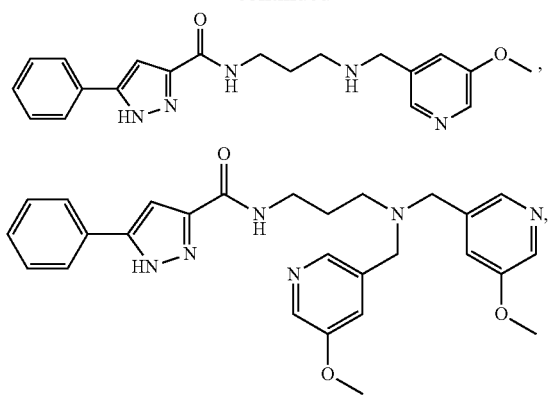
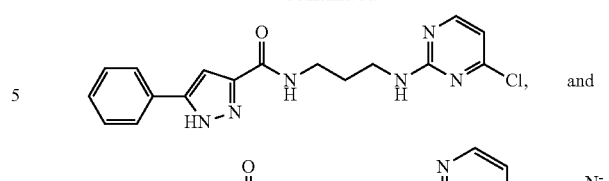
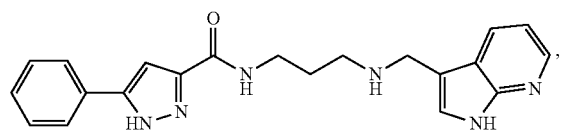
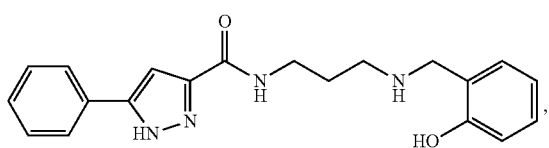
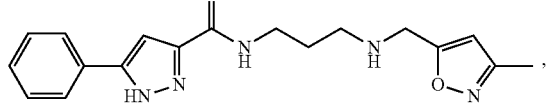
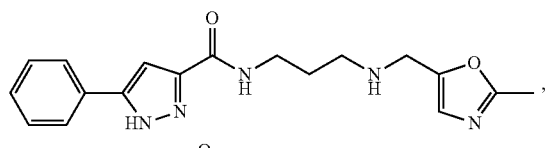
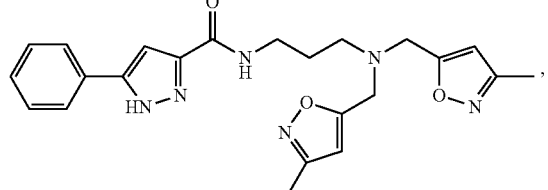
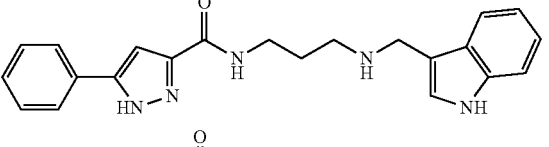
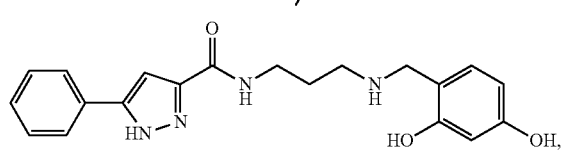
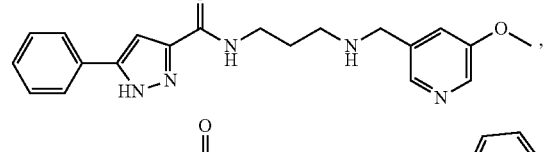
or a pharmaceutically acceptable salt thereof.
In a still further aspect, a compound is selected from:
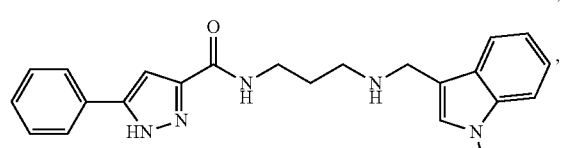
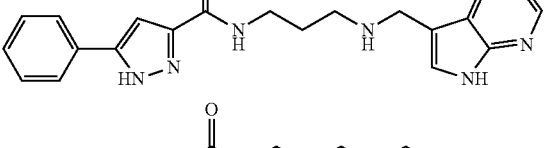
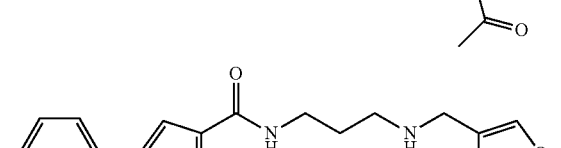
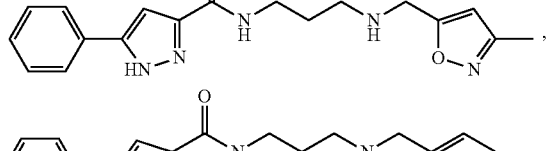
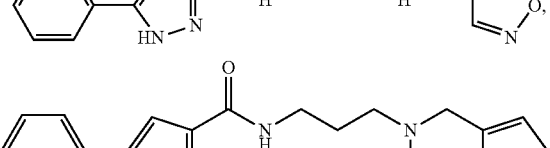
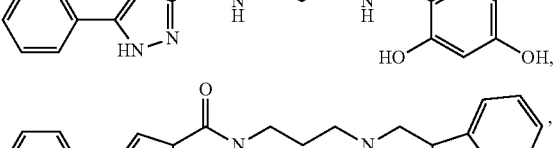
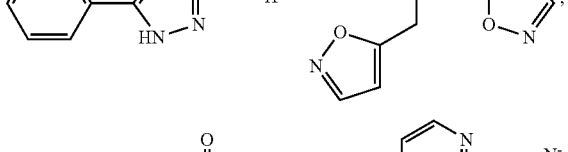
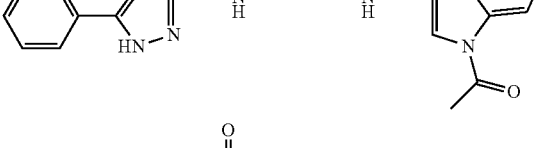
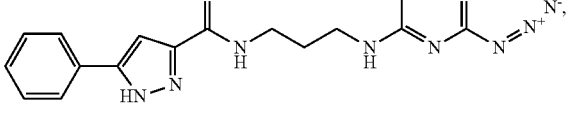
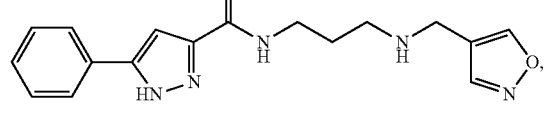

-continued
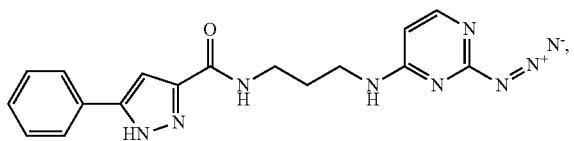
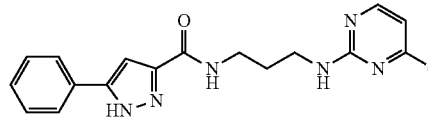
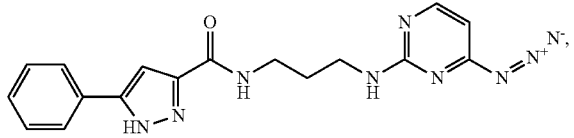
or a pharmaceutically acceptable salt thereof.
In yet a further aspect, a compound is selected from:
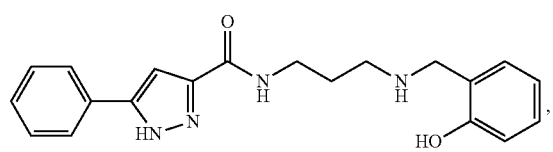
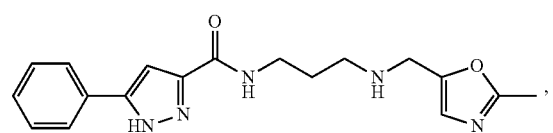
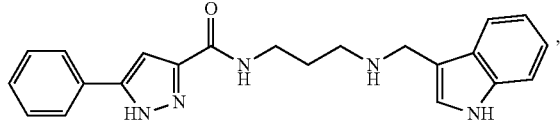
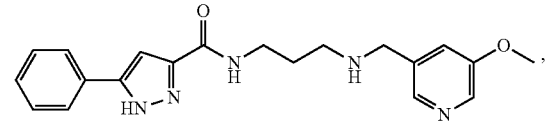
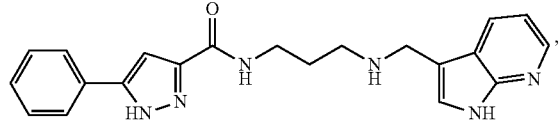
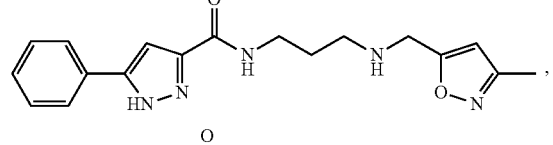
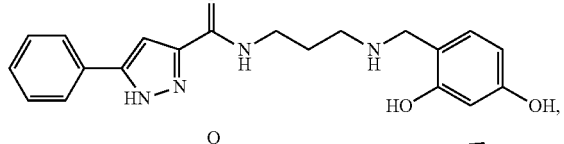
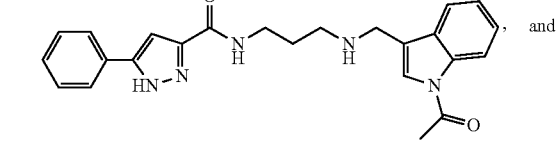
-continued
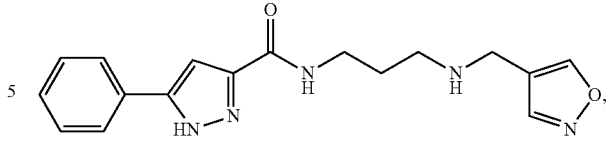
or a pharmaceutically acceptable salt thereof.
In an even further aspect, a compound is selected from:
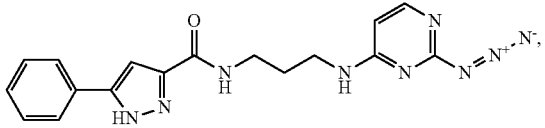
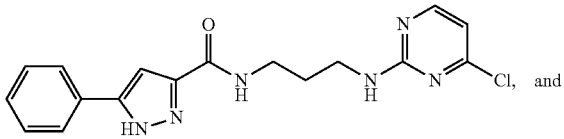
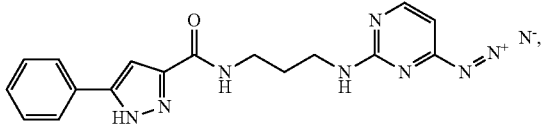
or a pharmaceutically acceptable salt thereof.
In a further aspect, a compound is selected from:
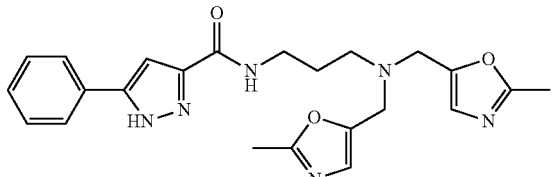
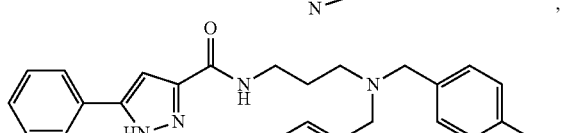
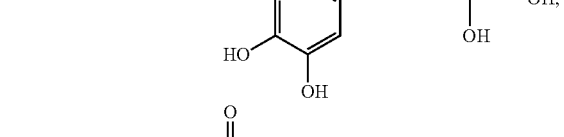
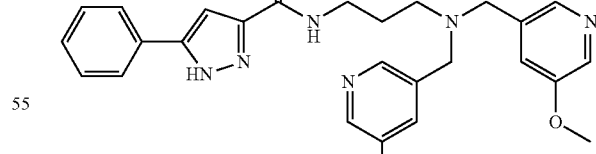
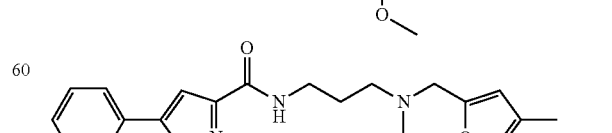
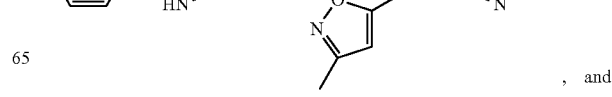
, and -continued

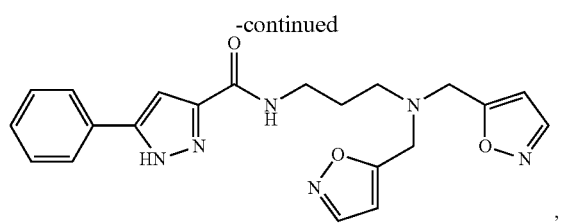

or a pharmaceutically acceptable salt thereof.

In one aspect, a compound is selected from:

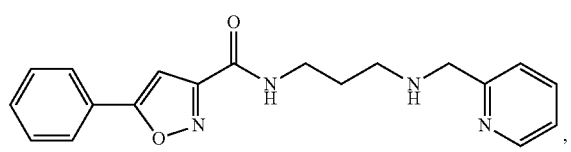 [SMILES: O=C(NCCCNCc1ccccn1)c1cc(-c2ccccc2)on1]

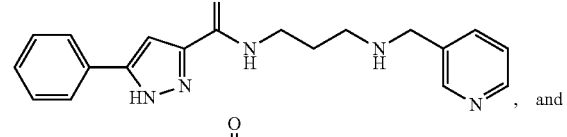

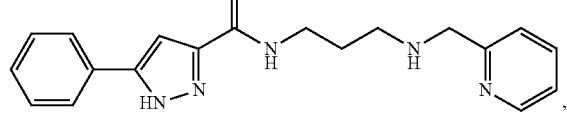

or a pharmaceutically acceptable salt thereof.

In a further aspect, a compound is:

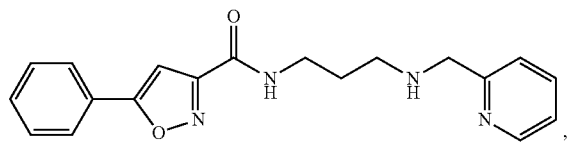

or a pharmaceutically acceptable salt thereof.

In a further aspect, a compound is selected from:

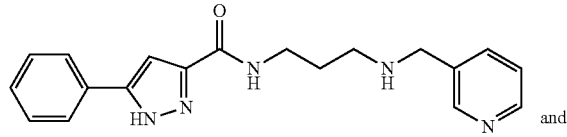

and

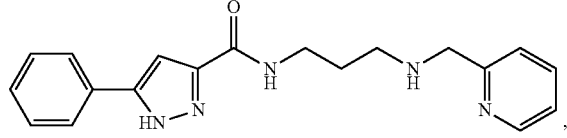

or a pharmaceutically acceptable salt thereof.

3. Prophetic Compound Examples

The following compound examples are prophetic, and can be prepared using the synthesis methods described herein above and other general methods as needed as would be known to one skilled in the art. It is anticipated that the prophetic compounds would be active as mediators of transcriptional induction of E-cadherin, and such activity can be determined using the assay methods described herein above.

In one aspect, a compound can be selected from:

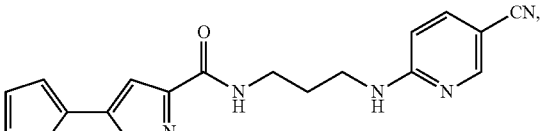

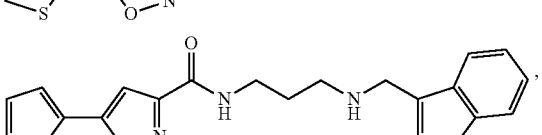

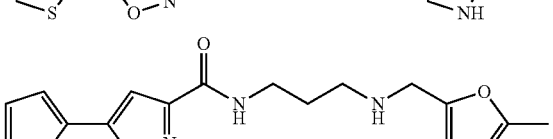

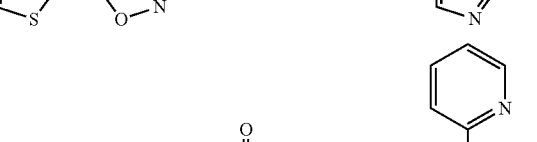

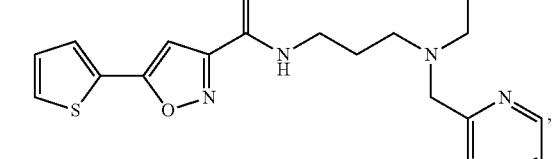

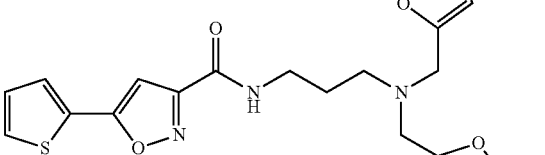

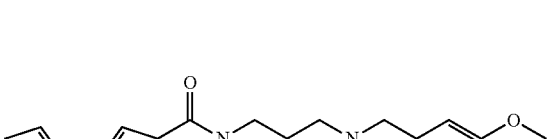

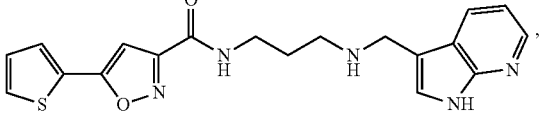

85
-continued
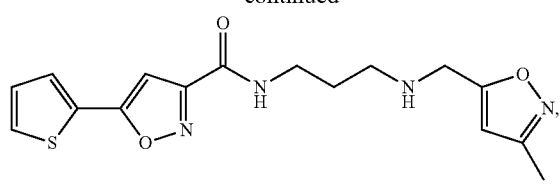
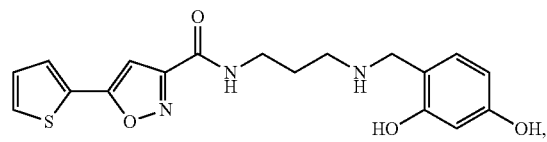
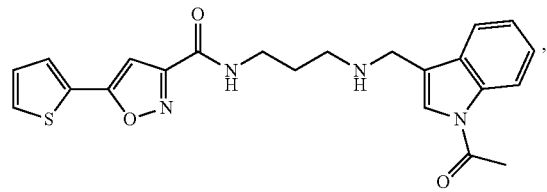
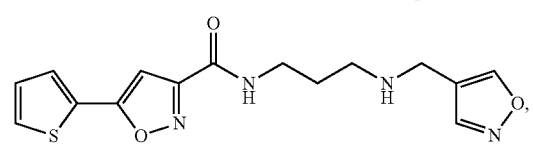
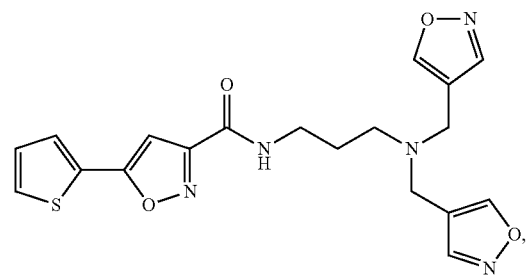
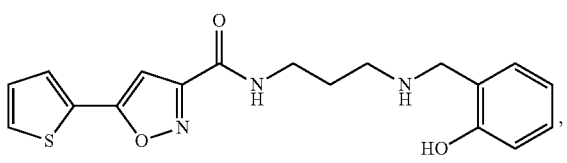
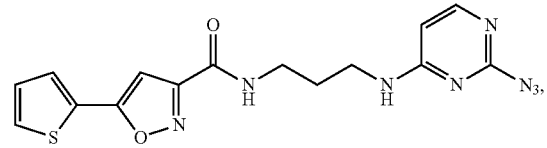
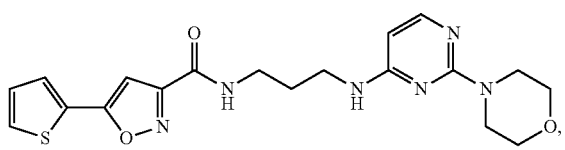
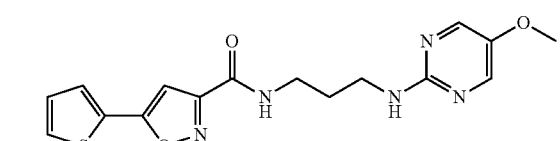
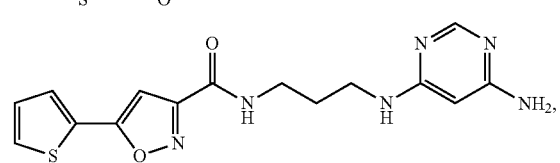
86
-continued
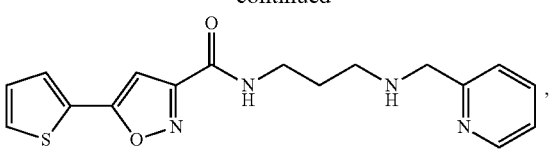
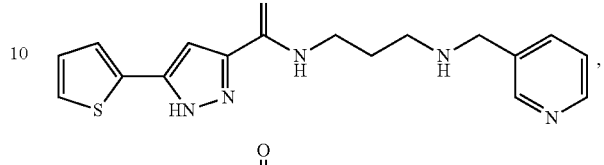
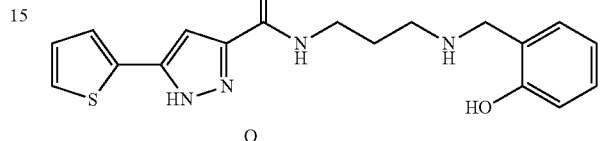
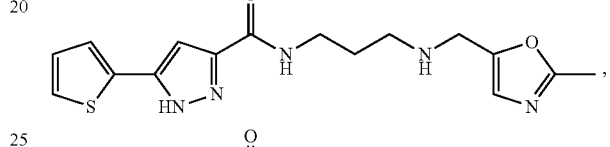
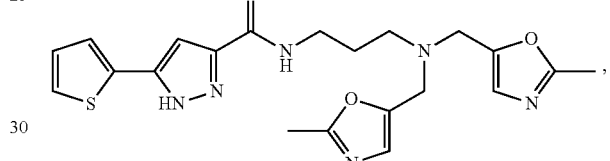
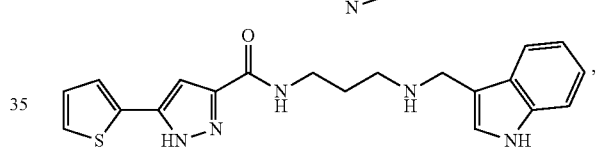
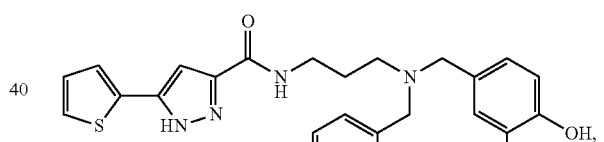
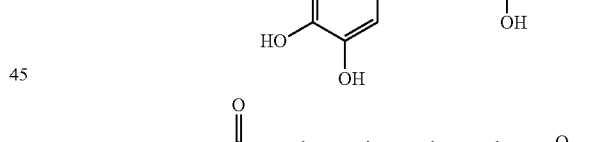
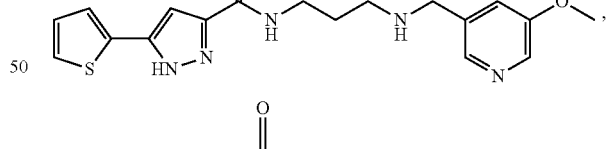
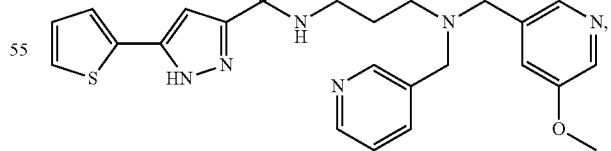
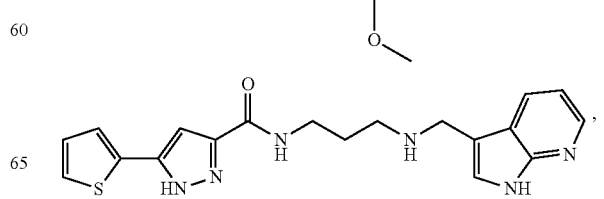

In a further aspect, a compound can be selected from:
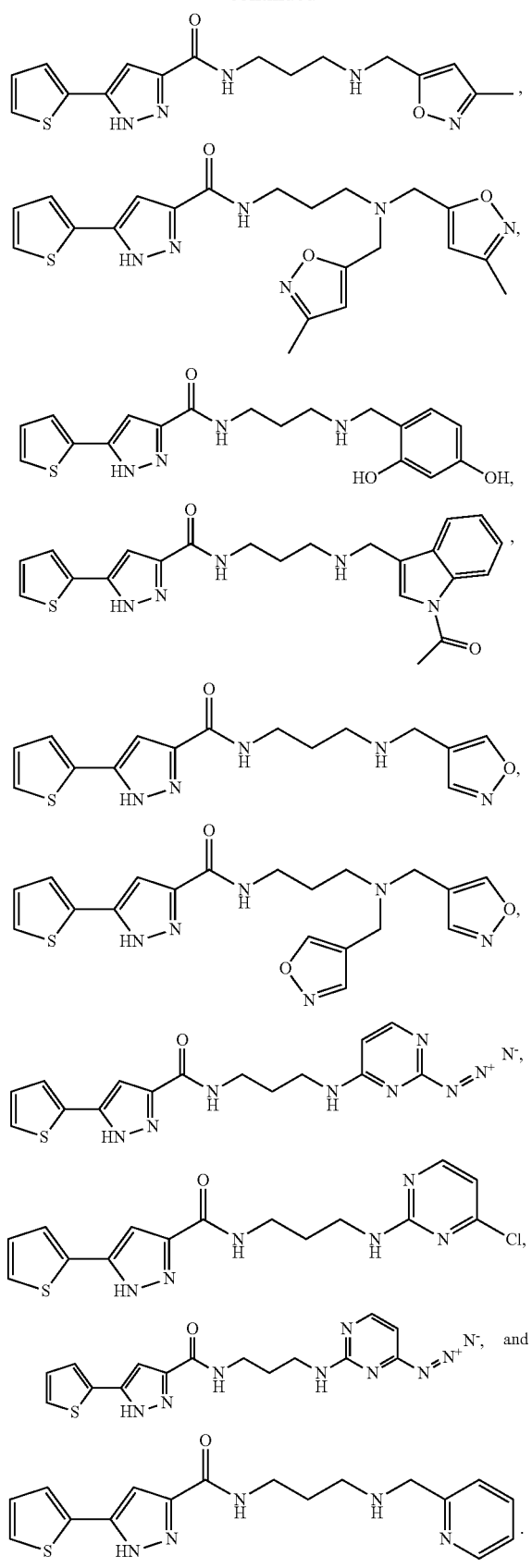

-continued
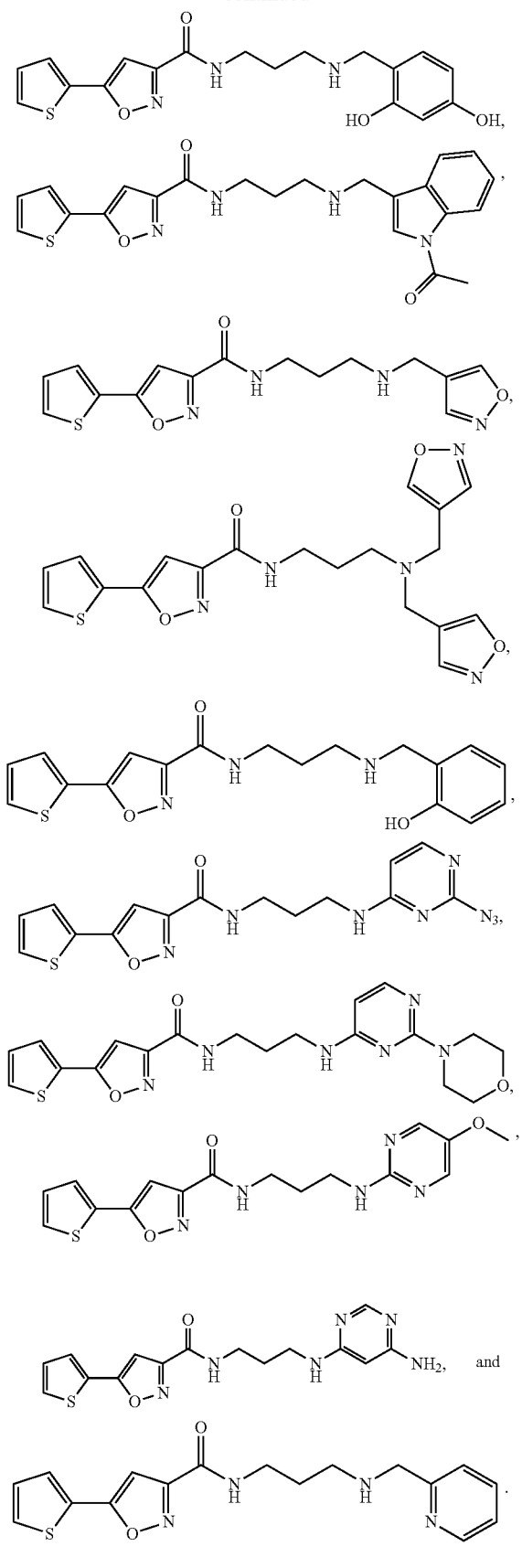
In a still further aspect, a compound can be selected from:
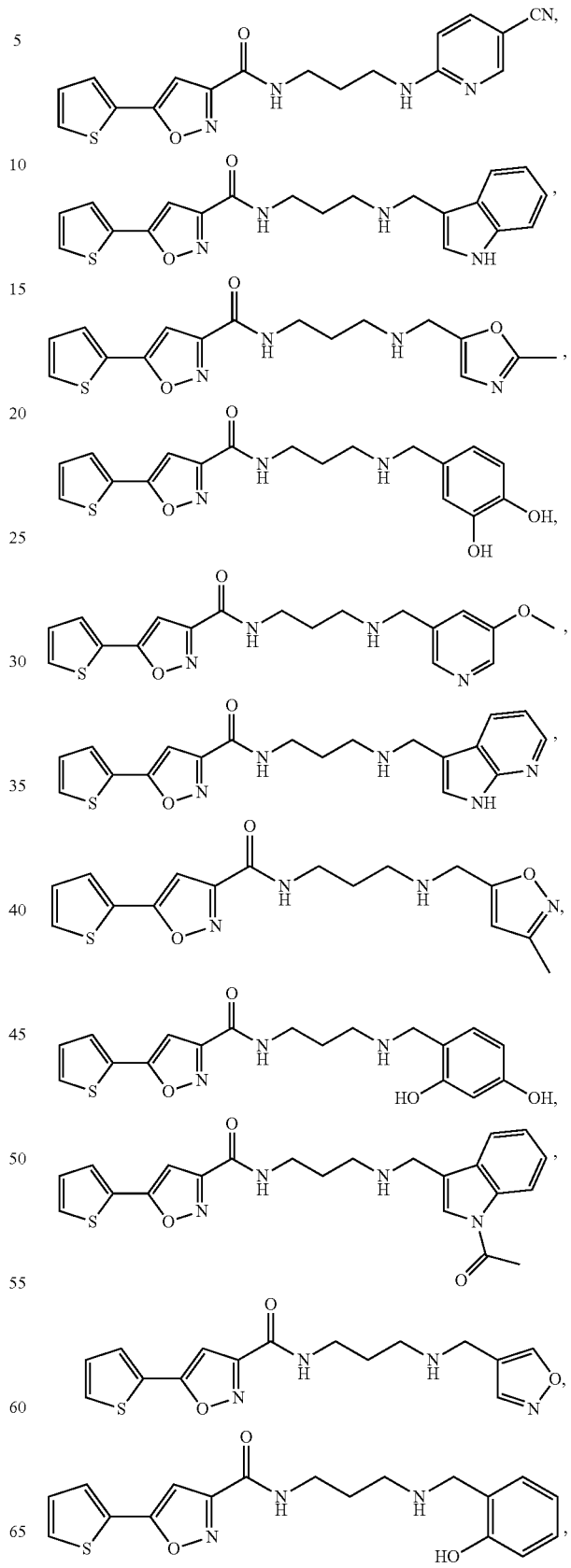

-continued
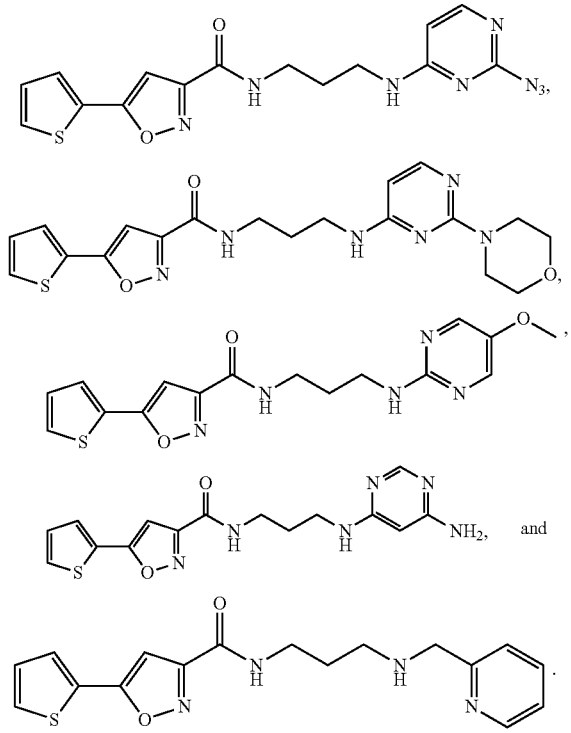
In yet a further aspect, a compound can be selected from:
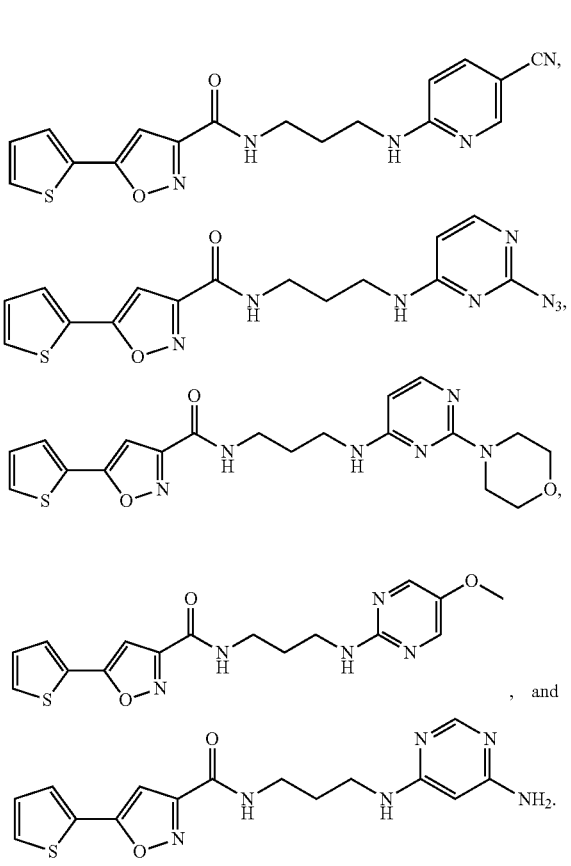
In an even further aspect, a compound can be selected from:
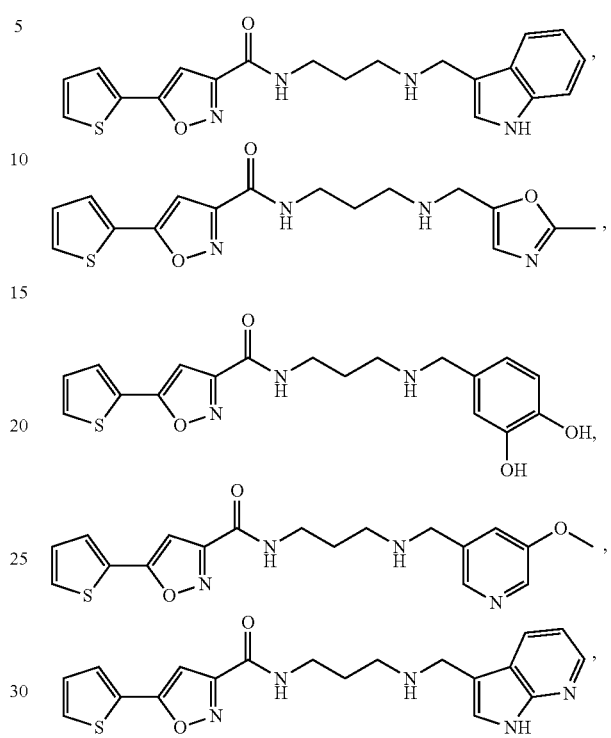

In a further aspect, a compound can be selected from:
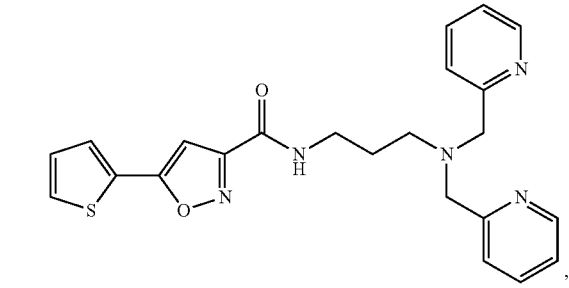
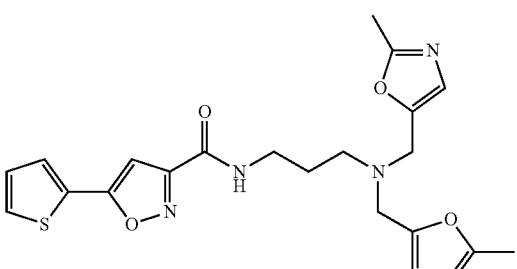
, and
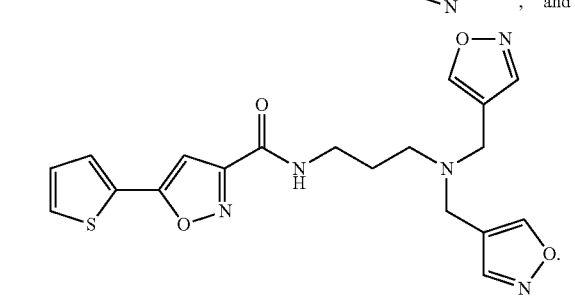
In a further aspect, a compound can be selected from:
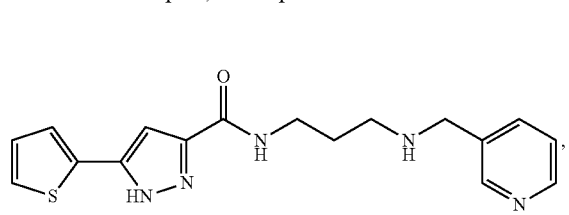
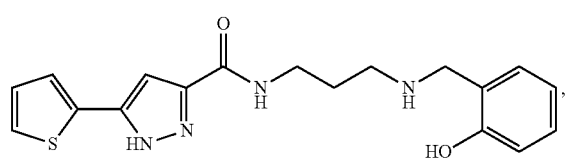
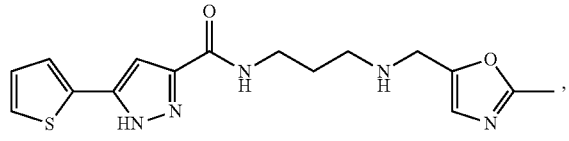
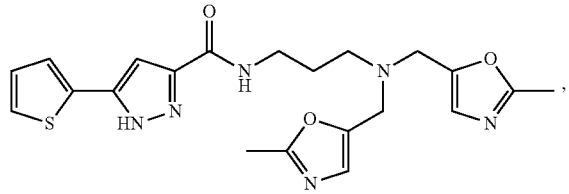
-continued
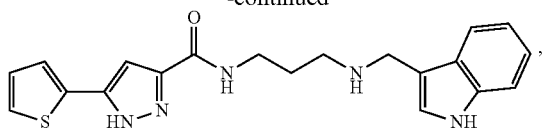
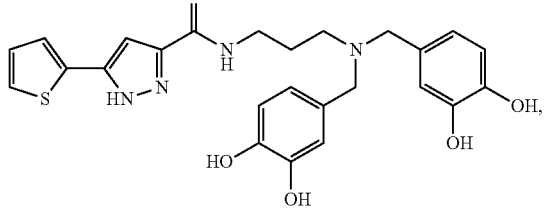
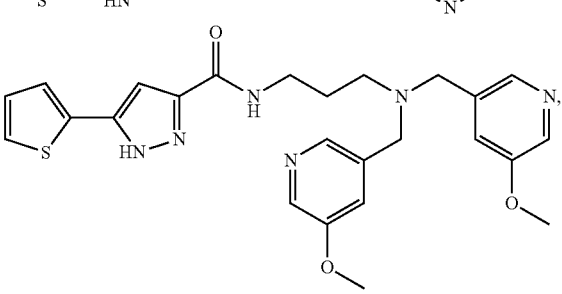
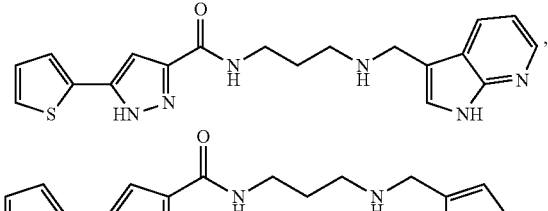
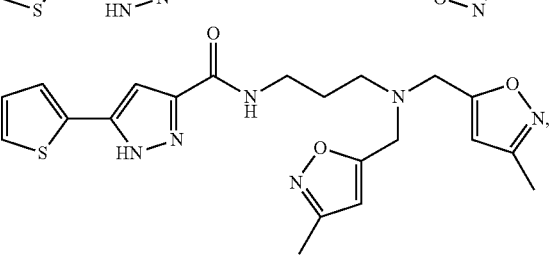
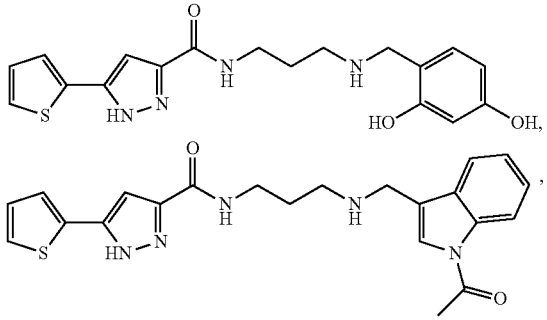
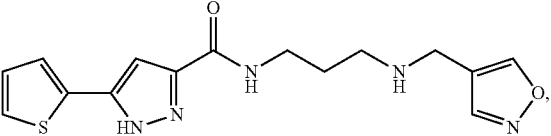

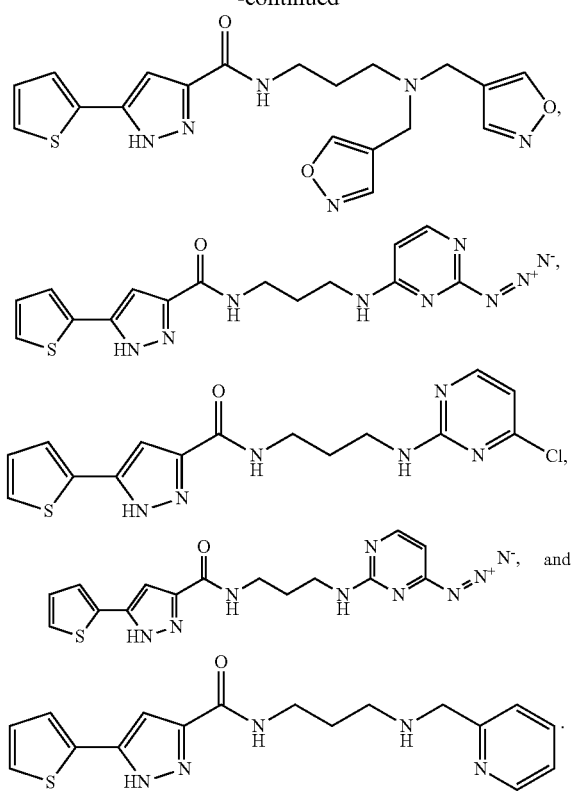
In a still further aspect, a compound can be selected from:
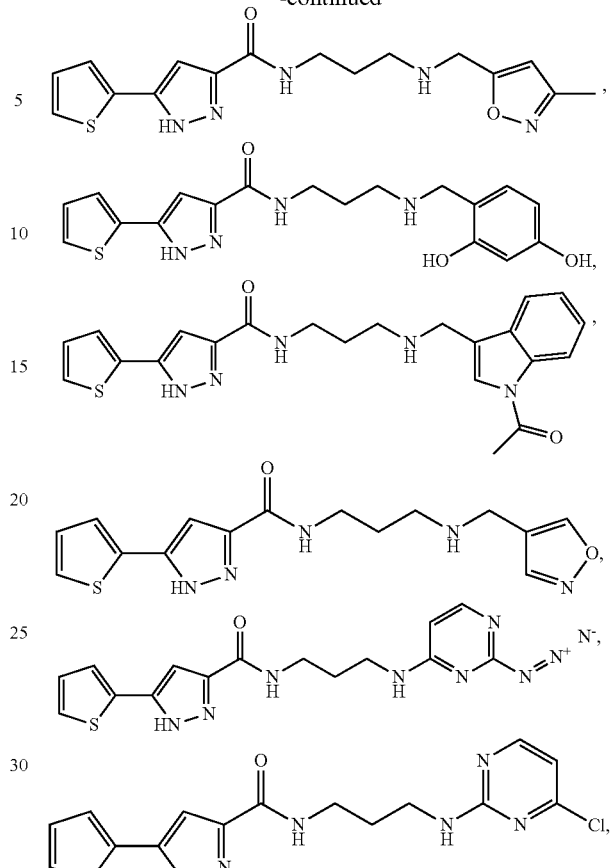
In yet a further aspect, a compound can be selected from:

In an even further aspect, a compound can be selected from:

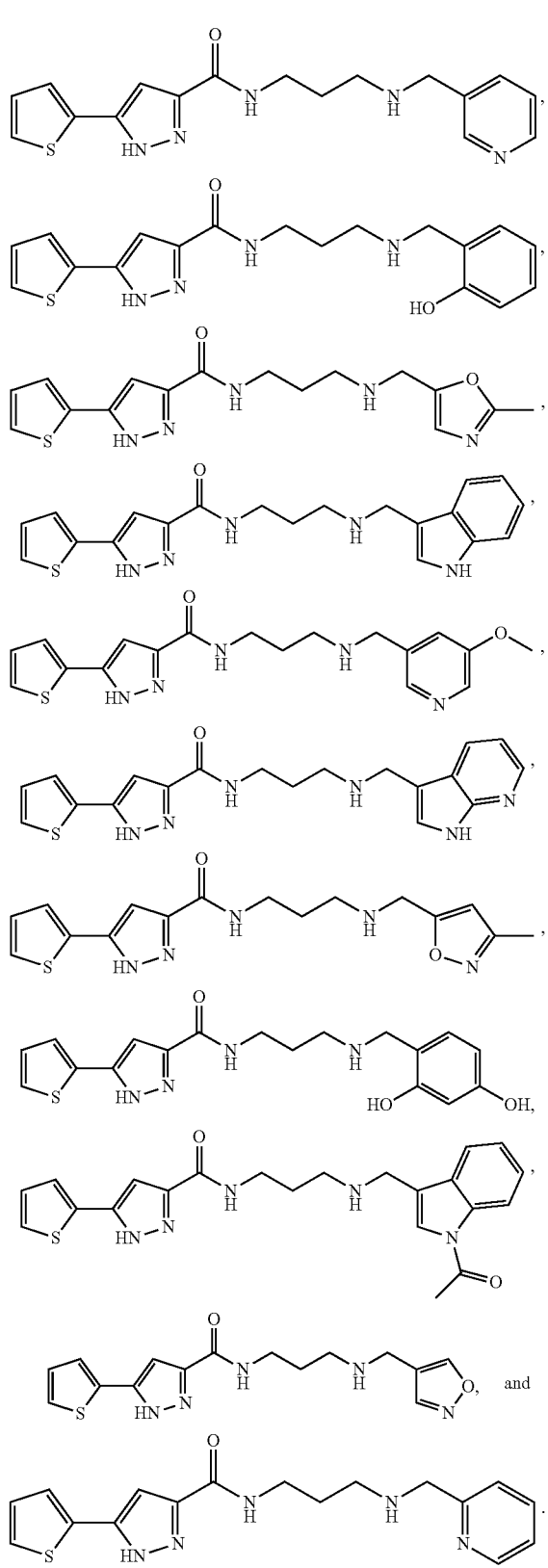

In a further aspect, a compound can be selected from:

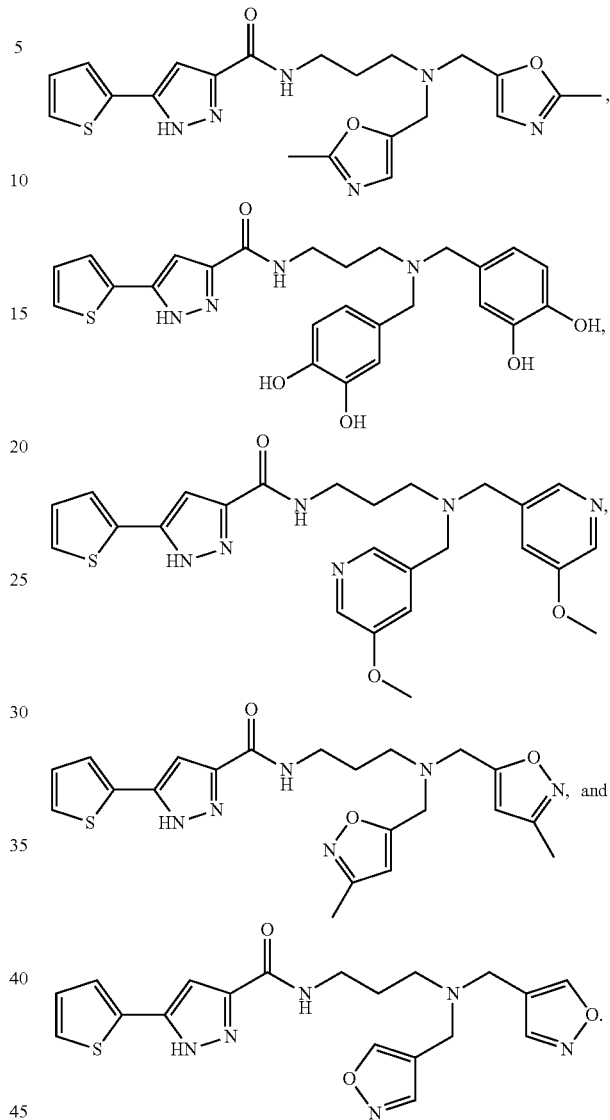

It is contemplated that one or more compounds can optionally be omitted from the disclosed invention.

It is understood that the disclosed compounds can be used in connection with the disclosed methods, compositions, kits, and uses.

It is understood that pharmaceutical acceptable derivatives of the disclosed compounds can be used also in connection with the disclosed methods, compositions, kits, and uses. The pharmaceutical acceptable derivatives of the compounds can include any suitable derivative, such as pharmaceutically acceptable salts as discussed below, isomers, radiolabeled analogs, tautomers, and the like.

C. Methods of Making the Compounds

In one aspect, the invention relates to methods of making compounds useful as mediators of transcriptional induction of E-cadherin, which can be useful in the treatment of disorders of uncontrolled cellular proliferation and other diseases in which E-cadherin is involved. In one aspect, the invention relates to the disclosed synthetic manipulations. In a further aspect, the disclosed compounds comprise the products of the synthetic methods described herein.

In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one product of the disclosed methods with a pharmaceutically acceptable carrier or diluent.

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed compositions, kits, and uses.

1. Route I

In one aspect, N-(aminoalkyl)-5-arylisoxazole-3-carboxamide analogs of the present invention can be prepared generically by the synthesis scheme as shown below. All positions are defined herein.

SCHEME 1A

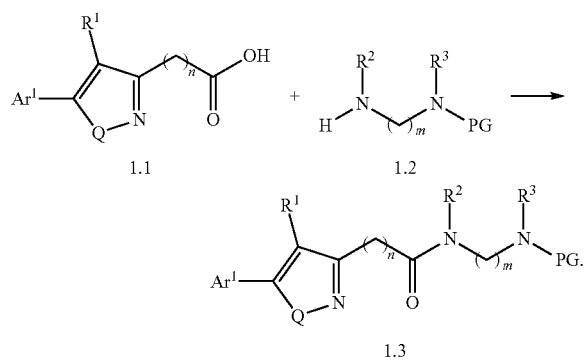

Compounds are represented in generic form, with groups as noted in compound descriptions elsewhere herein. A more specific example is set forth below.

SCHEME 1B

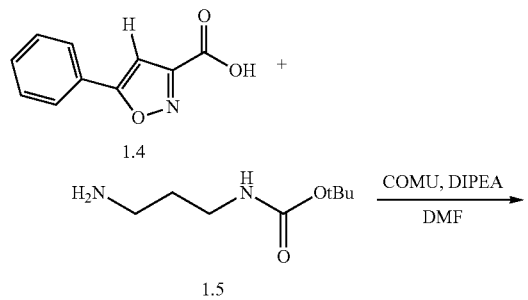

-continued

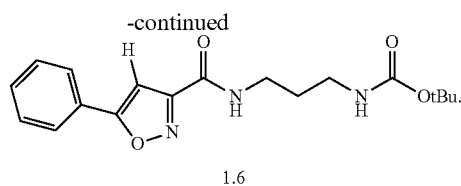

1.6

In one aspect, compounds of type 1.3, and similar compounds, can be prepared according to reaction Scheme 1B above. Thus, compounds of type 1.6 can be prepared by a coupling reaction of an appropriate carboxylic acid, e.g., 1.4 as shown above. Appropriate carboxylic acids are commercially available or prepared by methods known to one skilled in the art. The coupling reaction is carried out in the presence of a suitable base, e.g., N,N-diisopropylethyl amine (DIPEA) as shown above, and a suitable coupling agent, e.g., (1-cyano-2-ethoxy-2-oxoethylidenaminooxy)dimethylamino-morpholino-carbenium hexafluorophosphate (COMU), in a suitable solvent, e.g., dimethylformamide (DMF), and a suitable amine, e.g., tert-butyl(3-aminopropyl) carbamate (1.5) as shown above, which is commercially available or prepared by methods known to one skilled in the art. As can be appreciated by one skilled in the art, the above reaction provides an example of a generalized approach wherein compounds similar in structure to the specific reactants above (compounds similar to compounds of type 1.1 and 1.2), can be substituted in the reaction to provide N-(aminoalkyl)-5-arylisoxazole-3-carboxamide analogs similar to Formula 1.3.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

2. Route II

In one aspect, N-(aminoalkyl)-5-phenylisoxazole-3-carboxamide analogs of the present invention can be prepared generically by the synthesis scheme as shown below. All positions are defined herein.

SCHEME 2A

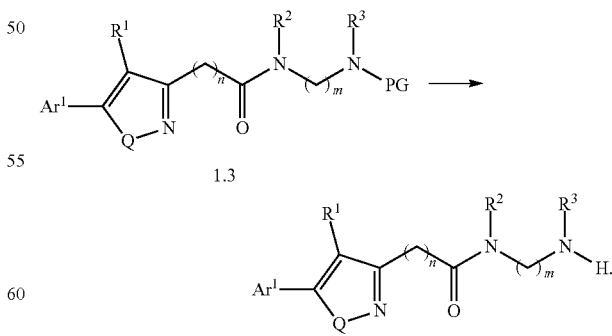

Compounds are represented in generic form, with groups as noted in compound descriptions elsewhere herein. A more specific example is set forth below.

SCHEME 2B

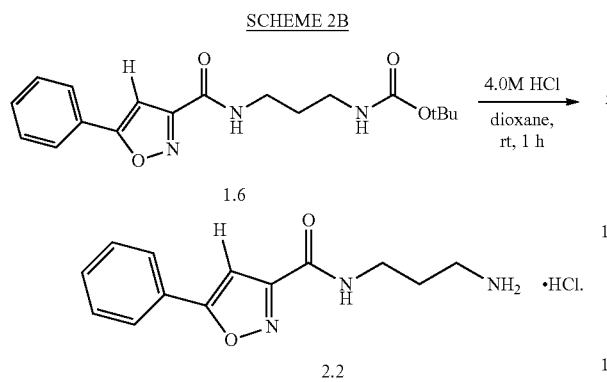

In one aspect, compounds of type 2.1, and similar compounds, can be prepared according to reaction Scheme 2B above. Thus, compounds of type 2.2 can be prepared by deprotection of an appropriate amide, e.g., 1.6 as shown above. The deprotection is carried out in the presence of a suitable acid, e.g., hydrochloric acid (HCl) as shown above, in a suitable solvent, e.g., dioxane, for a suitable period of time, e.g., 1 h. As can be appreciated by one skilled in the art, the above reaction provides an example of a generalized approach wherein compounds similar in structure to the specific reactants above (compounds similar to compounds of type 1.3), can be substituted in the reaction to provide N-(aminoalkyl)-5-phenylisoxazole-3-carboxamide analogs similar to Formula 2.1.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

3. Route III

In one aspect, N-(3-(((aryl)methyl)amino)alkyl)-5-arylisoxazole-3-carboxamide analogs of the present invention can be prepared generically by the synthesis scheme as shown below. All positions are defined herein.

SCHEME 3A

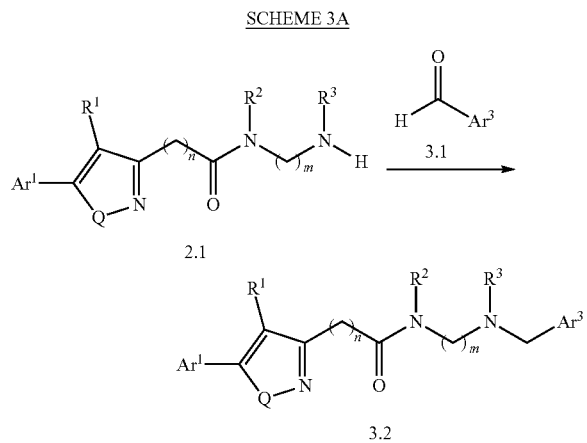

Compounds are represented in generic form, with groups as noted in compound descriptions elsewhere herein. A more specific example is set forth below.

SCHEME 3B

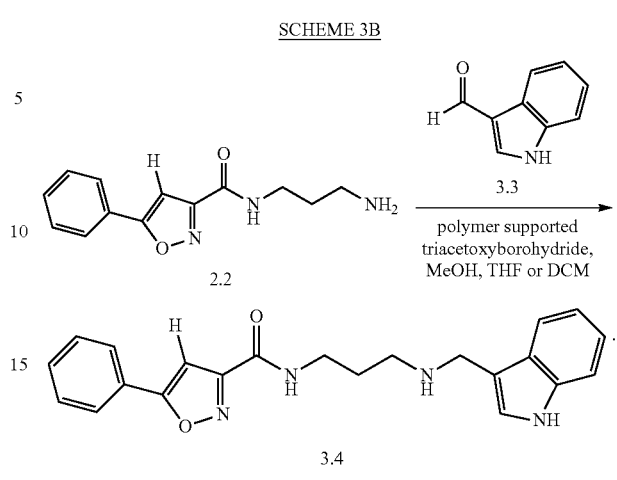

In one aspect, compounds of type 3.2, and similar compounds, can be prepared according to reaction Scheme 3B above. Thus, compounds of type 3.4 can be prepared by reductive amination using an appropriate amine, e.g., 2.2 as shown above. The reductive amination is carried out in the presence of a suitable aldehyde, e.g., 1H-indole-3-carbaldehyde (3.3), which is commercially available or prepared by methods known to one skilled in the art, and a suitable reducing agent, e.g., polymer supported triacetoxyborohydride, in the presence of a suitable solvent, e.g., methanol (MeOH), tetrahydrofuran (THF), or dichloromethane (DCM). As can be appreciated by one skilled in the art, the above reaction provides an example of a generalized approach wherein compounds similar in structure to the specific reactants above (compounds similar to compounds of type 2.1 and 3.1), can be substituted in the reaction to provide N-((arylmethylamino)alkyl)-5-arylisoxazole-3-carboxamide analogs similar to Formula 3.2.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

4. Route IV

In one aspect, N-(3-(arylamino)alkyl)-5-arylisoxazole-3-carboxamide analogs of the present invention can be prepared generically by the synthesis scheme as shown below. All positions are defined herein.

SCHEME 4A

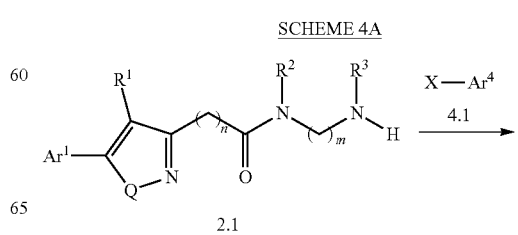

103

-continued

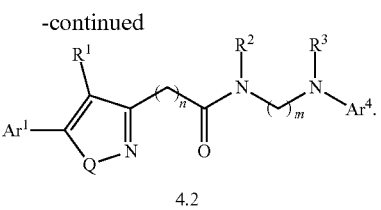

4.2

Compounds are represented in generic form, with groups as noted in compound descriptions elsewhere herein. A more specific example is set forth below.

SCHEME 4B

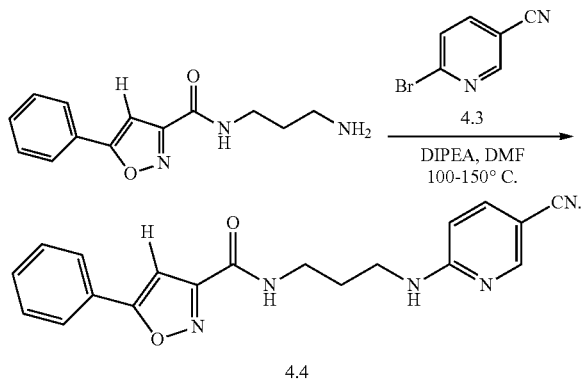

In one aspect, compounds of type 4.2, and similar compounds, can be prepared according to reaction Scheme 4B above. Thus, compounds of type 4.4 can be prepared by a coupling reaction of an appropriate amine, e.g., 2.2 as shown above. The coupling reaction is carried out in the presence of a suitable base, e.g., DIPEA as shown above, and a suitable aryl (or heteroaryl) halide, e.g., 6-bromonicotinonitrile (4.3), which is commercially available or prepared by methods known to one skilled in the art, in a suitable solvent, e.g., dimethylformamide (DMF), at a suitable temperature, e.g., 100-150° C. As can be appreciated by one skilled in the art, the above reaction provides an example of a generalized approach wherein compounds similar in structure to the specific reactants above (compounds similar to compounds of type 2.1 and 4.1), can be substituted in the reaction to provide N-(3-((5-aryl)amino)alkyl)-5-arylisoxazole-3-carboxamide analogs similar to Formula 4.2.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

D. Pharmaceutical Compositions

In one aspect, the invention relates to pharmaceutical compositions comprising the disclosed compounds. That is, a pharmaceutical composition can be provided comprising an effective amount of at least one disclosed compound, at least one product of a disclosed method of making, or a pharmaceutically acceptable salt, solvate, hydrate, or polymorph thereof, and a pharmaceutically acceptable carrier. In one aspect, the invention relates to pharmaceutical compositions comprising an effective amount of at least one

104 disclosed compound, or a pharmaceutically acceptable salt thereof, and a pharmaceutically acceptable carrier.

In one aspect, the invention relates to pharmaceutical compositions comprising an effective amount of a disclosed compound, a product of a disclosed method of making, or a pharmaceutically acceptable salt thereof, and a pharmaceutically acceptable carrier.

In a further aspect, the effective amount is a therapeutically effective amount. In a still further aspect, the effective amount is a prophylactically effective amount. In a still further aspect, the pharmaceutical composition comprises a compound that is a product of a disclosed method of making.

In a further aspect, the pharmaceutical composition exhibits potentiation of E-cadherin expression with an $EC_{50}$ of less than about $30 \times 10^{-6}$ M. In a still further aspect, the pharmaceutical composition exhibits potentiation of E-cadherin expression with an $EC_{50}$ of less than about $20 \times 10^{-6}$ M. In an even further aspect the pharmaceutical composition exhibits potentiation of E-cadherin expression with an $EC_{50}$ of less than about $10 \times 10^{-6}$ M. In yet a further aspect, the pharmaceutical composition exhibits potentiation of E-cadherin expression with an $EC_{50}$ of less than about $5 \times 10^{-6}$ M. In an even further aspect, the pharmaceutical composition exhibits potentiation of E-cadherin expression with an $EC_{50}$ of less than about $1 \times 10^{-6}$ M. In a still further aspect, the pharmaceutical composition exhibits potentiation of E-cadherin expression with an $EC_{50}$ of between from about $30 \times 10^{-6}$ M to about $1 \times 10^{-6}$ M. In a yet further aspect, the pharmaceutical composition exhibits potentiation of E-cadherin expression with an $EC_{50}$ of between from about $20 \times 10^{-6}$ M to about $1 \times 10^{-6}$ M. In an even further aspect, the pharmaceutical composition exhibits potentiation of E-cadherin expression with an $EC_{50}$ of between from about $10 \times 10^{-6}$ M to about $1 \times 10^{-6}$ M. In a still further aspect, the pharmaceutical composition exhibits potentiation of E-cadherin expression with an $EC_{50}$ of between from about $5 \times 10^{-6}$ M to about $1 \times 10^{-6}$ M. In a still further aspect, potentiation of the expression of E-cadherin is restoration of E-cadherin expression.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

The present invention is further directed to a method for the manufacture of a medicament for modulating the expression of E-cadherin (e.g., treatment of one or more disorders of cellular proliferation associated with E-cadherin activity) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

E. Methods for Modulating the Expression of E-Cadherin in Cells

In one aspect, the invention relates to a method for modulating the expression of E-cadherin in at least one cell, the method comprising the step of contacting the at least one cell with at least one compound having a structure represented by a formula:

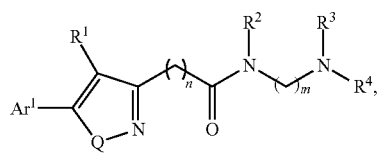

wherein m is an integer selected from 2, 3, and 4; wherein n is an integer selected from 0 and 1; wherein Q is selected from $NR^5$, O, and S; wherein $R^5$, when present, is selected from hydrogen and C1-C4 alkyl; wherein each of $R^1$ and $R^2$ is independently selected from hydrogen and C1-C4 alkyl; wherein $R^3$ is selected from hydrogen and $(CHR^6)_pAr^2$; wherein p, when present, is an integer selected from 0 and 1; wherein $R^6$, when present, is selected from hydrogen and C1-C4 alkyl; wherein $Ar^2$, when present, is selected from aryl and heteroaryl, and $Ar^2$ is substituted with 0, 1, 2, or 3 groups independently selected from halogen, —OH, —CN, —$N_3$, —$NH_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino; wherein $R^4$ is selected from $CH_2Ar^3$ and $Ar^4$; wherein $Ar^3$, when present, is selected from aryl and heteroaryl, and $Ar^3$ is substituted with 0, 1, 2, or 3 groups independently selected from halogen, —OH, —CN, —$N_3$, —$NH_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino; wherein $Ar^4$, when present, is selected from aryl and heteroaryl, and $Ar^4$ is substituted with 0, 1, 2, or 3 groups independently selected from halogen, —OH, —CN, —$N_3$, —$NH_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino; and wherein $Ar^1$, when present, is selected from aryl and heteroaryl, and wherein $Ar^1$, when present, is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino, or a pharmaceutically acceptable salt thereof.

In a further aspect, modulating is increasing. In a still further aspect, modulating is restoring.

In a further aspect, the cell is mammalian. In a still further aspect, the cell is human. In yet a further aspect, the cell has been isolated from a mammal prior to the contacting step.

In a further aspect, contacting is via administration to a mammal.

F. Methods for Treating a Disorder Associated with E-Cadherin Activity

In one aspect, the invention relates to a method for treating a disorder associated with E-cadherin activity in a subject, the method comprising administering to the subject an effective amount of at least one compound having a structure represented by a formula:

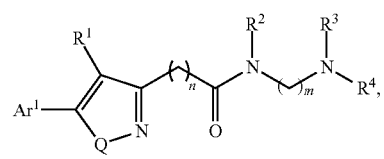

wherein m is an integer selected from 2, 3, and 4; wherein n is an integer selected from 0 and 1; wherein Q is selected from $NR^5$, O, and S; wherein $R^5$, when present, is selected from hydrogen and C1-C4 alkyl; wherein each of $R^1$ and $R^2$ is independently selected from hydrogen and C1-C4 alkyl; wherein $R^3$ is selected from hydrogen and $(CHR^6)_pAr^2$; wherein p, when present, is an integer selected from 0 and 1; wherein $R^6$, when present, is selected from hydrogen and C1-C4 alkyl; wherein $Ar^2$, when present, is selected from aryl and heteroaryl, and $Ar^2$ is substituted with 0, 1, 2, or 3 groups independently selected from halogen, —OH, —CN, —$N_3$, —$NH_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino; wherein $R^4$ is selected from $CH_2Ar^3$ and $Ar^4$; wherein $Ar^3$, when present, is selected from aryl and heteroaryl, and $Ar^3$ is substituted with 0, 1, 2, or 3 groups independently selected from halogen, —OH, —CN, —$N_3$, —$NH_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino; wherein $Ar^4$, when present, is selected from aryl and heteroaryl, and $Ar^4$ is substituted with 0, 1, 2, or 3 groups independently selected from halogen, —OH, —CN, —N$_3$, —NH$_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino; and wherein Ar$^1$, when present, is selected from aryl and heteroaryl, and wherein Ar$^1$, when present, is substituted with 0, 1, 2, or 3 groups independently selected from halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino, or a pharmaceutically acceptable salt thereof, thereby treating the disorder in the subject.

In a further aspect, the compound exhibits restoration of E-cadherin expression. In a still further aspect, the compound exhibits an increase in E-cadherin expression.

In a further aspect, the compound exhibits potentiation of E-cadherin expression with an EC$_{50}$ of less than about 30×10$^{-6}$ M. In a still further aspect, the compound exhibits potentiation of E-cadherin expression with an EC$_{50}$ of less than about 20×10$^{-6}$ M. In yet a further aspect, the compound exhibits potentiation of E-cadherin expression with an EC$_{50}$ of less than about 10×10$^{-6}$ M. In an even further aspect, the compound exhibits potentiation of E-cadherin expression with an EC$_{50}$ of less than about 1×10$^{-6}$ M. In a still further aspect, the compound exhibits potentiation of E-cadherin expression with an EC$_{50}$ of less than about 5×10$^{-6}$ M. In yet a further aspect, the compound exhibits potentiation of E-cadherin expression with an EC$_{50}$ of less than about 1×10$^{-6}$ M. In an even further aspect, the compound exhibits potentiation of E-cadherin expression with an EC$_{50}$ of between about 30×10$^{-6}$ M and about 1×10$^{-6}$ M. In a still further aspect, the compound exhibits potentiation of E-cadherin expression with an EC$_{50}$ of between about 20×10$^{-6}$ M and about 1×10$^{-6}$ M. In yet a further aspect, the compound exhibits potentiation of E-cadherin expression with an EC$_{50}$ of between about 10×10$^{-6}$ M and about 1×10$^{-6}$ M. In an even further aspect, the compound exhibits potentiation of E-cadherin expression with an EC$_{50}$ of between about 5×10$^{-6}$ M and about 1×10$^{-6}$ M.

In a further aspect, the subject is a mammal. In a still further aspect, the subject is a human.

In a further aspect, the subject has been diagnosed with a need for treatment of the disorder prior to the administering step. In a still further aspect, the method further comprises the step of identifying a subject in need of treatment of the disorder.

In a further aspect, the disorder associated with E-cadherin activity is a disorder of uncontrolled cellular proliferation. In a still further aspect, the disorder of uncontrolled cellular proliferation is cancer. In yet a further aspect, the disorder of uncontrolled cellular proliferation is selected from breast cancer, renal cancer, gastric cancer, and colorectal cancer. In an even further aspect, the disorder of uncontrolled cellular proliferation is selected from lymphoma, cancers of the brain, genitourinary tract cancer, lymphatic system cancer, stomach cancer, larynx cancer, lung, pancreatic cancer, breast cancer, and malignant melanoma.

G. Use of Compounds

Also provided are uses of the disclosed compounds and products. In one aspect, the invention relates to the use of at least one disclosed compound; or a pharmaceutically acceptable salt thereof. In a further aspect, the compound used is a product of a disclosed method of making.

In one aspect, the invention relates to use of a disclosed compound or a product of a disclosed method of making, or a pharmaceutically acceptable salt, solvate, or polymorph thereof.

In a further aspect, the compound exhibits potentiation of E-cadherin expression with an EC$_{50}$ of less than about 30×10$^{-6}$ M. In a still further aspect, the compound exhibits potentiation of E-cadherin expression with an EC$_{50}$ of less than about 20×10$^{-6}$ M. In yet a further aspect, the compound exhibits potentiation of E-cadherin expression with an EC$_{50}$ of less than about 10×10$^{-6}$ M. In an even further aspect, the compound exhibits potentiation of E-cadherin expression with an EC$_{50}$ of less than about 1×10$^{-6}$ M. In a still further aspect, the compound exhibits potentiation of E-cadherin expression with an EC$_{50}$ of less than about 5×10$^{-6}$ M. In yet a further aspect, the compound exhibits potentiation of E-cadherin expression with an EC$_{50}$ of less than about 1×10$^{-6}$ M.

In a further aspect, the compound exhibits potentiation of E-cadherin expression with an EC$_{50}$ of between about 30×10$^{-6}$ M and about 1×10$^{-6}$ M. In a still further aspect, the compound exhibits potentiation of E-cadherin expression with an EC$_{50}$ of between about 20×10$^{-6}$ M and about 1×10$^{-6}$ M. In yet a further aspect, the compound exhibits potentiation of E-cadherin expression with an EC$_{50}$ of between about 10×10$^{-6}$ M and about 1×10$^{-6}$ M. In an even further aspect, the compound exhibits potentiation of E-cadherin expression with an EC$_{50}$ of between about 5×10$^{-6}$ M and about 1×10$^{-6}$ M.

In a further aspect, the use relates to a process for preparing a pharmaceutical composition comprising a therapeutically effective amount of a disclosed compound or a product of a disclosed method of making, or a pharmaceutically acceptable salt thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt thereof, wherein a pharmaceutically acceptable carrier is intimately mixed with a therapeutically effective amount of the compound or the product of a disclosed method of making.

In various aspects, the use relates to a treatment of a disorder in a mammal. Also disclosed is the use of a compound for restoring E-cadherin expression. In one aspect, the use is characterized in that the mammal is a human. In one aspect, the use is characterized in that the disorder is a disorder of uncontrolled cellular proliferation associated with E-cadherin activity. In one aspect, the disorder of uncontrolled cellular proliferation associated with E-cadherin activity is treated by restoration of E-cadherin expression in a mammal.

In a further aspect, the use relates to the manufacture of a medicament for the treatment of a disorder associated with E-cadherin activity in a mammal. In a further aspect, the medicament is used in the treatment of a disorder of uncontrolled cellular proliferation associated with E-cadherin activity in a mammal.

In a further aspect, the use relates to modulation of E-cadherin expression in a mammal. In a still further aspect, the use relates to restoration of E-cadherin expression in a mammal. In yet a further aspect, the use relates to an increase in E-cadherin expression in a mammal. In an even further aspect, the use relates to modulating E-cadherin expression in a mammal. In a still further aspect, the use relates to modulating E-cadherin expression in a cell. In a yet further aspect, the mammal is a human.

In a further aspect, the use is treatment of a disorder of uncontrolled cellular proliferation. In a still further aspect, the disorder is a disorder of uncontrolled cellular proliferation associated with E-cadherin expression. In a yet further aspect, disorder of uncontrolled cellular proliferation is cancer. In an even further aspect, the disorder of uncontrolled cellular proliferation is selected from breast cancer, renal cancer, gastric cancer, and colorectal cancer. In a still further aspect, the disorder of uncontrolled cellular proliferation is selected from lymphoma, cancers of the brain, genitourinary tract cancer, lymphatic system cancer, stomach cancer, larynx cancer, lung, pancreatic cancer, breast cancer, and malignant melanoma.

It is understood that the disclosed uses can be employed in connection with the disclosed compounds, methods, compositions, and kits. In a further aspect, the invention relates to the use of a disclosed compound or a disclosed product in the manufacture of a medicament for the treatment of a disorder associated with E-cadherin expression in a mammal. In a further aspect, the disorder is a disorder of uncontrolled cellular proliferation.

H. Kits

In one aspect, the invention relates to a kit comprising at least one disclosed compound or at least one disclosed product and one or more of at least one agent known to increase E-cadherin expression; at least one agent known to decrease E-cadherin expression; at least one agent known to treat a disorder of uncontrolled cellular proliferation; or instructions for treating a disorder of uncontrolled cellular proliferation. In a further aspect, the at least one compound or the at least one product and the at least one agent are co-formulated. In a further aspect, the at least one compound or the at least one product and the at least one agent are co-packaged.

In one aspect, the invention relates to kit comprising at least one compound having a structure represented by a formula:

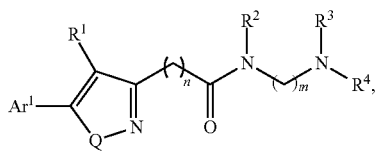

wherein m is an integer selected from 2, 3, and 4; wherein n is an integer selected from 0 and 1; wherein Q is selected from $NR^5$, O, and S; wherein $R^5$, when present, is selected from hydrogen and C1-C4 alkyl; wherein each of $R^1$ and $R^2$ is independently selected from hydrogen and C1-C4 alkyl; wherein $R^3$ is selected from hydrogen and $(CHR^6)_p Ar^2$; wherein p, when present, is an integer selected from 0 and 1; wherein each occurrence of $R^6$, when present, is independently selected from hydrogen and C1-C4 alkyl; wherein $Ar^2$, when present, is selected from aryl and heteroaryl, and $Ar^2$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino; wherein $R^4$ is selected from $CH_2Ar^3$ and $Ar^4$; wherein $Ar^3$, when present, is selected from aryl and heteroaryl, and $Ar^3$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino; wherein $Ar^4$, when present, is selected from aryl and heteroaryl, and $Ar^3$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino; and wherein $Ar^1$, when present, is selected from aryl and heteroaryl, and wherein $Ar^1$, when present, is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino, or a pharmaceutically acceptable salt thereof, and one or more of:
(a) at least one agent known to increase E-cadherin expression;
(b) at least one agent known to decrease E-cadherin expression;
(c) at least one agent known to treat a disorder of uncontrolled cellular proliferation; or
(d) instructions for treating a disorder of uncontrolled cellular proliferation.

In a further aspect, the at least one compound and the at least one agent are co-formulated. In a still further aspect, the at least one compound and the at least one agent are co-packaged.

In a further aspect, the at least one agent known to increase E-cadherin expression is a histone deacetylase (HDAC) inhibitor. In a still further aspect, the HDAC inhibitor is selected from trichostatin A, vorinostat, romidepsin, and belinostat.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

I. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein. The Examples are provided herein to illustrate the invention, and should not be construed as limiting the invention in any way. The Examples are typically depicted in free base form, according to the IUPAC naming convention. Examples are provided herein to illustrate the invention, and should not be construed as limiting the invention in any way.

1. Chemistry Experimental Methods

All non-aqueous reactions were performed in flame-dried or oven dried round-bottomed flasks under an atmosphere of argon. Stainless steel syringes or cannulae were used to transfer air- and moisture-sensitive liquids. Reaction temperatures were controlled using a thermocouple thermometer and analog hotplate stirrer. Reactions were conducted at room temperature (r.t., approximately 23° C.) unless otherwise noted. Analytical thin-layer chromatography (TLC) was performed on E. Merck silica gel 60 F254 plates and visualized using UV, ceric ammonium molybdate, potassium permanganate, and anisaldehyde stains. Yields were reported as isolated, spectroscopically pure compounds.

HPLC was conducted on a Gilson HPLC system using a Gemini-NX 5u C18 column. $^1$H NMR spectra were recorded on Bruker 400 MHz spectrometers and are reported relative to deuterated solvent signals. Data for $^1$H NMR spectra are reported as follows: chemical shift (δ ppm), multiplicity (s=singlet, d=doublet, t=triplet, dd=double of doublets, dt=doublet of triplets, q=quartet, m=multiplet, br=broad, app=apparent), coupling constants (Hz), and integration. LC/MS was conducted and recorded on an Agilent Technologies 6140 Quadrupole instrument. Microwave reactions were conducted on a Biotage Initiator 2.0 microwave reactor.

a. General Procedure for Arylation (General Procedure A)

A solution containing 1 equivalent of the required amine, 1 equivalent of the desired aryl halide or heteroaryl halide, 2.5 equivalents of DIPEA, and DMF (1-3 mL) was heated in a microwave reactor at 100° C. to 150° C. for a suitable period of time until the reaction was complete (generally 15 min to 1.5 h). The solvents were removed under reduced pressure and the residues were subjected to preparative HPLC purification to give the final product.

(1) Synthesis of N-(3-((5-cyanopyridin-2-yl)amino)propyl)-5-phenylisoxazole-3-carboxamide (Compound 1)

i) Preparation of tert-butyl (3-(5-phenylisoxazole-3-carboxamido)propyl)carbamate

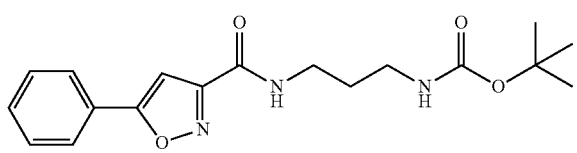 [SMILES: CC(C)(C)OC(=O)NCCCNC(=O)c1cc(-c2ccccc2)on1]

To a solution containing 1.0 g (5.29 mmol) of 3-phenylisoxazole-3-carboxylic acid and 0.89 g (5.56 mmol) of tert-butyl(3-aminopropyl)carbamate in 10 mL of DMF was added 2.5 g (5.82 mmol) of COMU, followed by 2.0 mL (11.1 mmol) of DIPEA. The reaction mixture was allowed to stir at rt overnight. The solvents were removed under reduced pressure and the residue was subjected to silica gel chromatography to give 1.55 g (85%) of tert-butyl (3-(5-phenylisoxazole-3-carboxamido)propyl)carbamate as a yellow solid: LC/MS: 1.22 min, m/z=368.2 [M+K]$^+$.

ii) Preparation of N-(3-aminopropyl)-5-phenylisoxazole-3-carboxamide hydrochloride

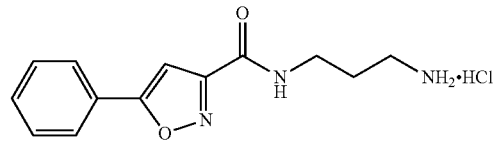

A mixture containing 1.5 g (4.35 mmol) of tert-butyl (3-(5-phenylisoxazole-3-carboxamido)propyl)carbamate, 50 mL of DCM, and 10 mL of a 4.0M solution of HCl in dioxane was allowed to stir at rt for 1 h. The solvents were removed under reduced pressure to give 1.22 g (100%) of N-(3-aminopropyl)-5-phenylisoxazole-3-carboxamide as its hydrochloride salt, which was used with no further purification. $^1$H NMR (400 MHz, CD$_3$OD): δ 7.89-7.87 (m, 2H), 7.54-7.51 (m, 3H), 7.10 (s, 1H), 3.51 (t, 2H, J=6.8 Hz), 3.02 (t, 2H, J=7.2 Hz), 2.01-1.94 (m, 2H); LC/MS: 0.79 min, m/z=246.3 [M+H]$^+$.

iii) Preparation of N-(3-((5-cyanopyridin-2-yl)amino)propyl)-5-phenylisoxazole-3-carboxamide (Compound 1)

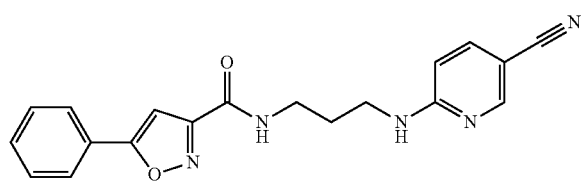 [SMILES: N#Cc1ccc(NCCCNC(=O)c2cc(-c3ccccc3)on2)nc1]

According to General Procedure A, N-(3-(5-cyanopyridin-2-yl)amino)propyl)-5-phenylisoxazole-3-carboxamide was synthesized from N-(3-aminopropyl)-5-phenylisoxazole-3-carboxamide. LC/MS ret. time=0.970 min, m/z=348.20 [M+H]$^+$.

(2) Synthesis of N-(3-((2-azidopyrimidin-4-yl)amino)propyl)-5-phenylisoxazole-3-carboxamide (Compound 17)

1) Preparation of N-(3-((2-chloropyrimidin-4-yl)amino)propyl)-5-phenylisoxazole-3-carboxamide

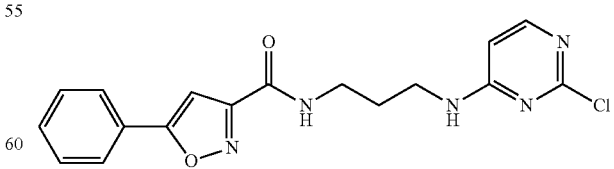

According to General Procedure A, N-(3-((2-chloropyrimidin-4-yl)amino)propyl)-5-phenylisoxazole-3-carboxamide was synthesized from N-(3-aminopropyl)-5-phenylisoxazole-3-carboxamide. $^1$H NMR (400 MHz, CD$_3$OD): δ 7.92-7.85 (m, 3H), 7.54-7.49 (m, 3H), 7.07 (s, 1H), 6.56

(br d, 1H, J=4.2 Hz), 3.64-3.58 (br m, 2H), 3.49 (t, 2H, J=6.6 Hz), 1.95 (t, 2H, J=6.5 Hz); LC/MS ret. time=1.037 min, m/z=358.20 [M+H]⁺.

ii) Preparation of N-(3-((2-azidopyrimidin-4-yl)amino)propyl)-5-phenylisoxazole-3-carboxamide (Compound 17)

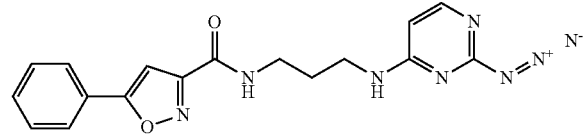

A mixture containing 18 mg (0.050 mmol) of N-(3-((2-chloropyrimidin-4-yl)amino)propyl)-5-phenylisoxazole-3-carboxamide, 7 mg (0.10 mmol) of sodium azide, and 5 mL of EtOH was heated at reflux overnight. The solvents were removed under reduced pressure and the residue was submitted to HPLC purification to give 4.7 mg (26%) of N-(3-((2-azidopyrimidin-4-yl)amino)propyl)-5-phenylisoxazole-3-carboxamide. $^1$H NMR (400 MHz, d⁶-DMSO): δ 8.93 (d, 1H, J=7.5 Hz), 8.88 (t, 1H, J=5.4 Hz), 8.44 (t, 1H, J=4.9 Hz), 7.93-7.90 (m, 2H), 7.56-7.52 (m, 3H), 7.34 (s, 1H), 6.60 (d, 1H, J=7.5 Hz), 3.47-3.42 (m, 2H), 3.40-3.35 (m, 2H), 1.91-1.83 (m, 2H); LC/MS ret. time=1.012 min, m/z=365.20 [M+H]⁺.

(3) Synthesis of N-(3-((5-methoxypyrimidin-2-yl)amino)propyl)-5-phenylisoxazole-3-carboxamide (Compound 19)

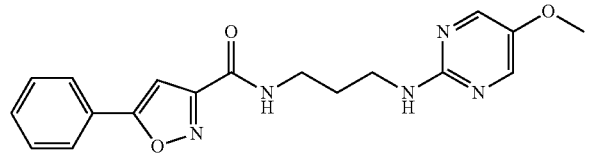 [SMILES: COc1cnc(NCCCNC(=O)c2cc(-c3ccccc3)on2)nc1]

According to General Procedure A, N-(3-(5-methoxypyrimidin-2-yl)amino)propyl)-5-phenylisoxazole-3-carboxamide was synthesized from N-(3-aminopropyl)-5-phenylisoxazole-3-carboxamide. $^1$H NMR (400 MHz, CD₃OD): δ 7.88-7.86 (m, 2H), 7.57-7.51 (m, 3H), 7.09 (s, 1H), 5.90 (s, 1H), 3.55-3.44 (m, 4H), 1.95-1.88 (m, 2H); LC/MS ret. time=0.981 min, m/z=353.0 [M+H]⁺.

(4) Synthesis of N-(3-((6-aminopyrimidin-4-yl)amino)propyl)-5-phenylisoxazole-3-carboxamide (Compound 20)

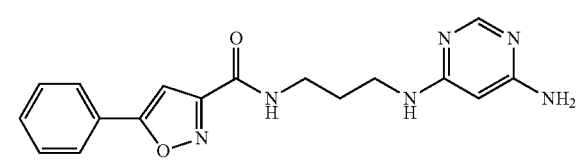 [SMILES: Nc1cc(NCCCNC(=O)c2cc(-c3ccccc3)on2)ncn1]

According to General Procedure A, N-(3-(6-aminopyrimidin-4-yl)amino)propyl)-5-phenylisoxazole-3-carboxamide was synthesized from N-(3-aminopropyl)-5-phenylisoxazole-3-carboxamide. LC/MS ret. time=0.943 min, m/z=339.0 [M+H]⁺.

(5) Synthesis of N-(3-((2-azidopyrimidin-4-yl)amino)propyl)-5-phenyl-1H-pyrazole-3-carboxamide (Compound 37)

1) Preparation of N-(3-((2-chloropyrimidin-4-yl)amino)propyl)-5-phenyl-1H-pyrazole-3-carboxamide

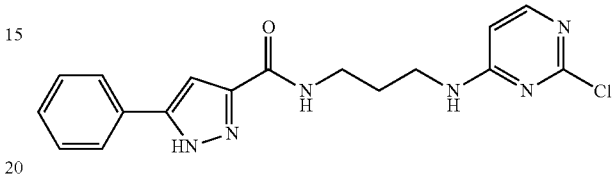

According to General Procedure A, N-(3-(2-chloropyrimidin-4-yl)amino)propyl)-5-phenyl-1H-pyrazole-3-carboxamide was synthesized from 5-phenyl-N-(3-((pyridin-2-ylmethyl)amino)propyl)-1H-pyrazole-3-carboxamide. LC/MS ret. time=0.912 min, m/z.

ii) Preparation of N-(3-((2-azidopyrimidin-4-yl)amino)propyl)-5-phenyl-1H-pyrazole-3-carboxamide (Compound 37)

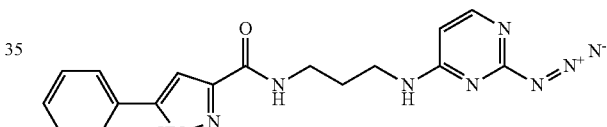

A solution containing 55 mg (0.154 mmol) of N-(3-((2-chloropyrimidin-4-yl)amino)propyl)-5-phenyl-1H-pyrazole-3-carboxamide, 30 mg (0.46 mmol) of sodium azide, and 5 mL of EtOH was heated at reflux overnight. The solvents were removed under reduced pressure and the residue was slurried in water. 30 mg (54%) of N-(3-((2-azidopyrimidin-4-yl)amino)propyl)-5-phenyl-1H-pyrazole-3-carboxamide was collected as a white solid. $^1$H NMR (400 MHz, CD₃OD): δ 8.73 (d, 1H, J=7.6 Hz), 7.80 (br s, 1H), 7.70 (d, 2H, J=7.2 Hz), 7.47-7.38 (m, 3H), 7.30 (br s, 1H), 7.02 (s, 1H), 6.59 (d, 1H, J=7.6 Hz), 3.62 (t, 2H, J=6.8 Hz), 3.51 (t, 2H, J=6.8 Hz), 2.10-1.95 (m, 2H); LC/MS ret. time=0.904 min, m/z=364.20 [M+H]⁺.

(6) Synthesis of N-(3-((4-chloropyrimidin-2-yl)amino)propyl)-5-phenyl-1H-pyrazole-3-carboxamide (Compound 38)

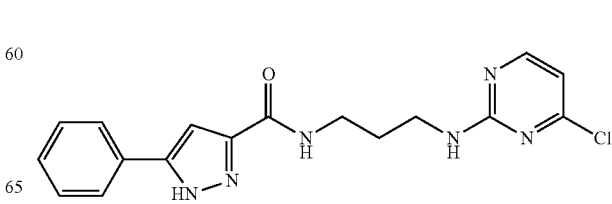

According to General Procedure A, N-(3-(4-chloropyrimidin-2-yl)amino)propyl)-5-phenyl-1H-pyrazole-3-carboxamide was synthesized from 5-phenyl-N-(3-((pyridin-2-ylmethyl)amino)propyl)-1H-pyrazole-3-carboxamide. LC/MS ret. time=1.026 min, m/z=357.20 [M+H]$^+$.

b. General Procedure for Reductive Amination (General Procedure B)

A mixture containing 1 equivalent of the required amine, 1.05 equivalents of the desired aldehyde, 2 equivalents of polymer-supported triacetoxyborohydride, 0.5-1.0 mL of methanol, and a suitable amount of THF or DCM (generally 2-5 mL), were shaken overnight. The reaction mixture was filtered and the solvents were removed under reduced pressure. The residue was subjected to preparative HPLC purification to give the final products. Mono- and di-alkylated products can both be produced from this method and are separable in purification.

(1) Synthesis of N-(3-(((1H-indol-3-yl)methyl)amino)propyl)-5-phenylisoxazole-3-carboxamide (Compound 2)

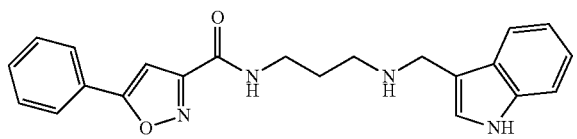 [SMILES: O=C(NCCCNCc1c[nH]c2ccccc12)c1cc(-c2ccccc2)on1]

According to General Procedure B, N-(3-(((1H-indol-3-yl)methyl)amino)propyl)-5-phenylisoxazole-3-carboxamide was synthesized from N-(3-aminopropyl)-5-phenylisoxazole-3-carboxamide. LC/MS ret. time=1.051 min, m/z=375.30 [M+H]$^+$.

(2) Synthesis of 5-phenyl-N-(3-((pyridin-3-ylmethyl)amino)propyl)isoxazole-3-carboxamide (Compound 3)

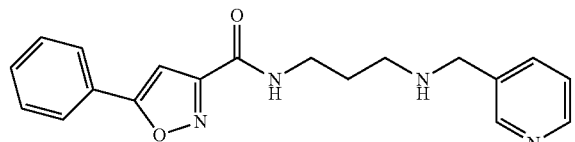

According to General Procedure B, 5-phenyl-N-(3-((pyridin-3-ylmethyl)amino)propyl)isoxazole-3-carboxamide was synthesized from N-(3-aminopropyl)-5-phenylisoxazole-3-carboxamide. $^1$H NMR (400 MHz, CD$_3$OD): δ 8.91 (d, 1H, J=1.3 Hz), 8.80 (d, 1H, J=5.1 Hz), 8.43 (d, 1H, J=8.0 Hz), 7.89-7.84 (m, 3H), 7.55-7.51 (m, 2H), 7.10 (s, 1H), 4.44 (s, 2H), 3.54 (t, 2H, J=6.4 Hz), 3.23 (t, 2H, J=7.4 Hz), 2.12-2.03 (m, 2H); LC/MS ret. time=0.755 min, m/z=326.20 [M+H]$^+$.

(3) Synthesis of N-(3-(((2-methyloxazol-5-yl)methyl)amino)propyl)-5-phenylisoxazole-3-carboxamide (Compound 4)

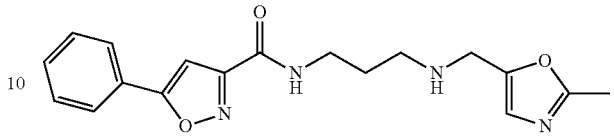

According to General Procedure B, N-(3-(((2-methyloxazol-5-yl)methyl)amino)propyl)-5-phenylisoxazole-3-carboxamide was synthesized from N-(3-aminopropyl)-5-phenylisoxazole-3-carboxamide. LC/MS ret. time=0.911 min, m/z=341.2 [M+H]$^+$.

(4) Synthesis of 5-phenyl-N-(3-((pyridin-2-ylmethyl)amino)propyl)isoxazole-3-carboxamide (Compound 5)

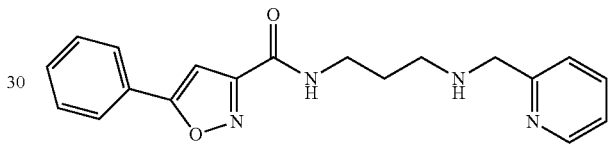

According to General Procedure B, 5-phenyl-N-(3-((pyridin-2-ylmethyl)amino)propyl)isoxazole-3-carboxamide was synthesized from N-(3-aminopropyl)-5-phenylisoxazole-3-carboxamide. $^1$H NMR (400 MHz, CD$_3$OD): δ 8.64 (d, 1H, J=4.8 Hz), 7.90-7.83 (m, 3H), 7.55-7.51 (3H), 7.47 (d, 1H, J=7.8 Hz), 7.41 (dd, 1H, J=7.4, 5.1 Hz), 7.10 (s, 1H), 4.40 (s, 2H), 3.54 (t, 2H, J=6.6 Hz), 3.22 (t, 2H, J=7.5 Hz), 2.14-2.06 (m, 2H); LC/MS ret. time=0.893 min, m/z=337.20 [M+H]$^+$.

(5) Synthesis of N-(3-(bis(pyridin-2-ylmethyl)amino)propyl)-5-phenylisoxazole-3-carboxamide (Compound 6)

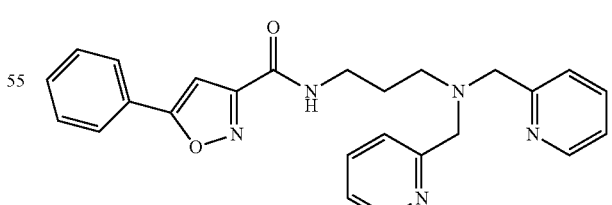

According to General Procedure B, N-(3-(bis(pyridin-2-ylmethyl)amino)propyl)-5-phenylisoxazole-3-carboxamide was synthesized from N-(3-aminopropyl)-5-phenylisoxazole-3-carboxamide. LC/MS ret. time=0.883 min, m/z=428.20 [M+H]$^+$.

(6) Synthesis of N-(3-(bis((2-methyloxazol-5-yl)methyl)amino)propyl)-5-phenylisoxazole-3-carboxamide (Compound 7)

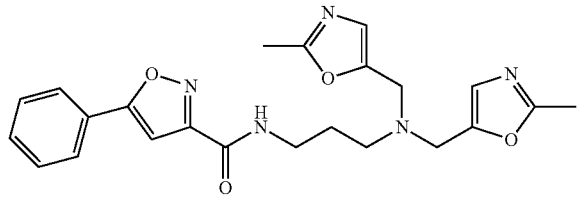 [SMILES: Cc1ncc(CN(CCCNC(=O)c2cc(-c3ccccc3)on2)Cc2cnc(C)o2)o1]

According to General Procedure B, N-(3-(bis((2-methyloxazol-5-yl)methyl)amino)propyl)-5-phenylisoxazole-3-carboxamide was synthesized from N-(3-aminopropyl)-5-phenylisoxazole-3-carboxamide. $^1$H NMR (400 MHz, CD$_3$OD): δ 8.04 (s, 2H), 7.91-7.86 (m, 2H), 7.58-7.51 (m, 3H), 7.10 (s, 1H), 4.33 (s, 4H), 3.50 (t, 2H, J=6.3 Hz), 3.29 (t, 2H, J=8.2 Hz), 2.44 (s, 6H), 2.26-2.15 (m, 2H); LC/MS ret. time=0.988 min, m/z=436.30 [M+H]$^+$.

(7) Synthesis of N-(3-((3,4-dihydroxybenzyl)amino)propyl)-5-phenylisoxazole-3-carboxamide (Compound 8)

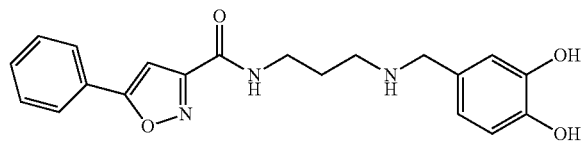 [SMILES: O=C(NCCCNCc1ccc(O)c(O)c1)c1cc(-c2ccccc2)on1]

According to General Procedure B, N-(3-((3,4-dihydroxybenzyl)amino)propyl)-5-phenylisoxazole-3-carboxamide was synthesized from N-(3-aminopropyl)-5-phenylisoxazole-3-carboxamide. $^1$H NMR (400 MHz, CD$_3$OD): δ 8.96 (br s, 1H), 7.89 (d, 1H, J=2.6 Hz), 7.88 (s, 1H), 7.54-7.51 (m, 3H), 7.10 (s, 1H), 6.93 (s, 1H), 6.81 (s, 2H), 4.05 (s, 2H), 3.50 (t, 2H, J=6.4 Hz), 3.08 (t, 2H, J=7.5 Hz), 2.04-21.97 (m, 2H) LC/MS ret. time=0.865 min, m/z=368.20 [M+H]$^+$.

(8) Synthesis of N-(3-(((5-methoxypyridin-3-yl)methyl)amino)propyl)-5-phenylisoxazole-3-carboxamide (Compound 9)

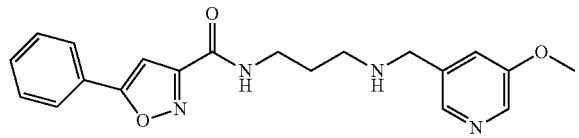 [SMILES: COc1cncc(CNCCCNC(=O)c2cc(-c3ccccc3)on2)c1]

According to General Procedure B, N-(3-(((5-methoxypyridin-3-yl)methyl)amino)propyl)-5-phenylisoxazole-3-carboxamide was synthesized from N-(3-aminopropyl)-5-phenylisoxazole-3-carboxamide. LC/MS ret. time=0.808 min, m/z=367.30 [M+H]$^+$.

(9) Synthesis of N-(3-(((1H-pyrrolo[2,3-B]pyridin-3-yl)methyl)amino)propyl)-5-phenylisoxazole-3-carboxamide (Compound 10)

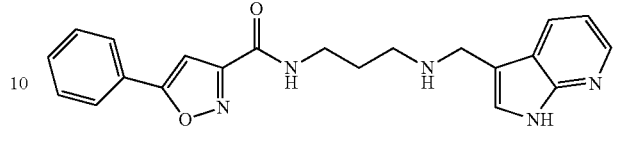

According to General Procedure B, N-(3-(((1H-pyrrolo[2,3-b]pyridin-3-yl)methyl)amino)propyl)-5-phenylisoxazole-3-carboxamide was synthesized from N-(3-aminopropyl)-5-phenylisoxazole-3-carboxamide. LC/MS ret. time=0.856 min, m/z=376.20 [M+H]$^+$.

(10) Synthesis of N-(3-(((3-methylisoxazol-5-yl)methyl)amino)propyl)-5-phenylisoxazole-3-carboxamide (Compound 11)

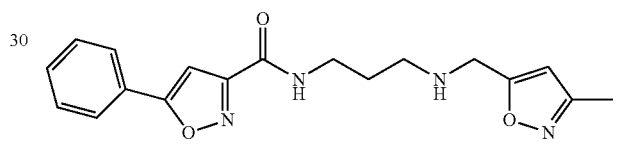

According to General Procedure B, N-(3-(((3-methylisoxazol-5-yl)methyl)amino)propyl)-5-phenylisoxazole-3-carboxamide was synthesized from N-(3-aminopropyl)-5-phenylisoxazole-3-carboxamide. LC/MS ret. time=0.911 min, m/z=341.20 [M+H]$^+$.

(11) Synthesis of N-(3-((2,4-dihydroxybenzyl)amino)propyl)-5-phenylisoxazole-3-carboxamide (Compound 12)

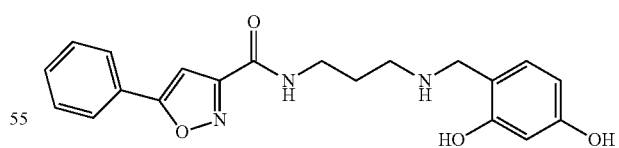

According to General Procedure B, N-(3-((2,4-dihydroxybenzyl)amino)propyl)-5-phenylisoxazole-3-carboxamide was synthesized from N-(3-aminopropyl)-5-phenylisoxazole-3-carboxamide. $^1$H NMR (400 MHz, CD$_3$OD): δ 7.89-7.86 (m, 2H), 7.55-7.50 (m, 3H), 7.10 (d, 1H, J=8.3 Hz), 7.08 (s, 1H), 6.39 (d, 1H, J=1.8 Hz), 6.32 (dd, 1H, J=8.2, 2.2 Hz), 4.12 (s, 2H), 3.50 (t, 2H, J=6.5 Hz), 3.08 (t, 2H, J=7.4 Hz), 2.08-1.98 (m, 2H); LC/MS ret. time=0.879 min, m/z=368.20 [M+H]+.

(12) Synthesis of N-(3-(((1-acetyl-1H-indol-3-yl)methyl)amino)propyl)-5-phenylisoxazole-3-carboxamide (Compound 13)

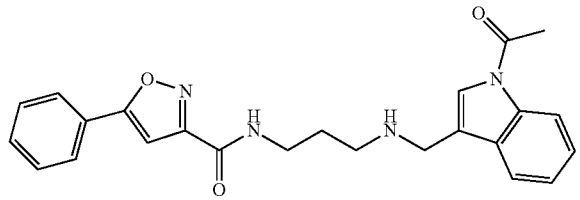 [SMILES: CC(=O)n1cc(CNCCCNC(=O)c2cc(-c3ccccc3)on2)c2ccccc21]

According to General Procedure B, N-(3-(((1-acetyl-1H-indol-3-yl)methyl)amino)propyl)-5-phenylisoxazole-3-carboxamide was synthesized from N-(3-aminopropyl)-5-phenylisoxazole-3-carboxamide. ¹H NMR (400 MHz, CD₃OD): δ 8.43-8.40 (m, 1H0, 7.99 (s, 1H), 7.91-7.88 (m, 3H), 7.82-7.79 (m, 1H), 7.60-7.52 (m, 4H), 7.42-7.38 (m, 2H), 7.02 (s, 1H), 4.47 (s, 2H), 3.55 (t, 2H, J=6.4 Hz), 3.22 (t, 2H, J=7.4 Hz), 2.71 (s, 3H), 2.11-2.06 (m, 2H), LC/MS ret. time=1.078 min, m/z=417.30 [M+H]⁺.

(13) Synthesis of N-(3-((isoxazol-4-ylmethyl)amino)propyl)-5-phenylisoxazole-3-carboxamide (Compound 14)

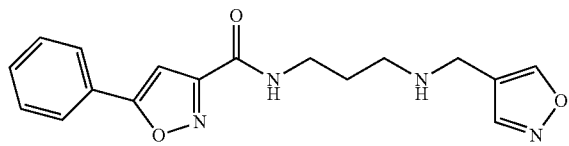 [SMILES: O=C(NCCCNCc1cnoc1)c1cc(-c2ccccc2)on1]

According to General Procedure B, N-(3-((isoxazol-4-ylmethyl)amino)propyl)-5-phenylisoxazole-3-carboxamide was synthesized from N-(3-aminopropyl)-5-phenylisoxazole-3-carboxamide LC/MS ret. time=0.862 min, m/z=327.30 [M+H]⁺.

(14) Synthesis of N-(3-(bis(isoxazol-4-ylmethyl)amino)propyl)-5-phenylisoxazole-3-carboxamide (Compound 15)

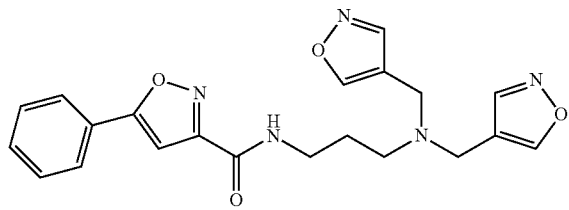 [SMILES: O=C(NCCCN(Cc1cnoc1)Cc1cnoc1)c1cc(-c2ccccc2)on1]

According to General Procedure B, N-(3-(bis(isoxazol-4-ylmethyl)amino)propyl)-5-phenylisoxazole-3-carboxamide was synthesized from N-(3-aminopropyl)-5-phenylisoxazole-3-carboxamide LC/MS ret. time=0.902 min, m/z=408.30 [M+H]⁺.

(15) Synthesis of N-(3-((2-hydroxybenzyl)amino)propyl)-5-phenylisoxazole-3-carboxamide (Compound 16)

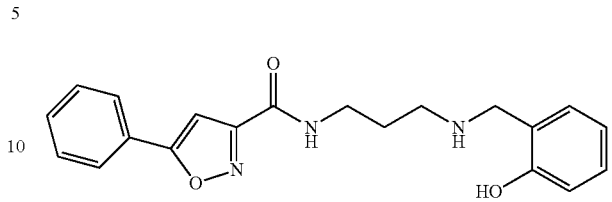

According to General Procedure B, N-(3-((2-hydroxybenzyl)amino)propyl)-5-phenylisoxazole-3-carboxamide was synthesized from N-(3-aminopropyl)-5-phenylisoxazole-3-carboxamide LC/MS ret. time=0.959 min, m/z=352.20 [M+H]⁺.

(16) Synthesis of N-(3-((2-hydroxybenzyl)amino)propyl)-5-phenyl-1H-pyrazole-3-carboxamide (Compound 21)

i) Preparation of tert-butyl (3-(5-phenyl-1H-pyrazole-3-carboxamido)propyl)carbamate

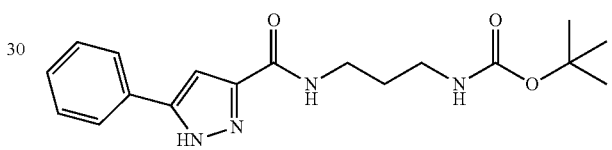

To a solution containing 0.31 g (1.65 mmol) of 5-phenyl-1H-pyrazole-3-carboxylic acid and 3 mL of DMF was added 0.77 g (1.82 mmol) of COMU, 0.28 g (1.73 mmol) of tert-butyl(3-aminopropyl)carbamate, and 0.45 mL (2.5 mmol) of DIPEA. The reaction mixture was allowed to stir at rt overnight, quenched by the addition of 10% HCl in water, and extracted with DCM. The combined organic layers were dried by passage through a phase separator cartridge and the solvent was removed under reduced pressure. The residue was subjected to silica gel chromatography to give 0.59 g (100%) of tert-butyl (3-(5-phenyl-1H-pyrazole-3-carboxamido)propyl)carbamate as a yellow oily solid. LC/MS ret. time=1.124 min, m/z=289.30 [M-C(CH₃)₃]⁺.

ii) Preparation of 5-phenyl-N-(3-((pyridin-2-ylmethyl)amino)propyl)-1H-pyrazole-3-carboxamide trifloroacetate

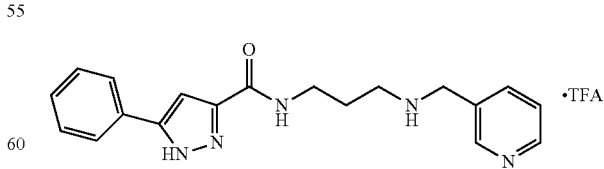

A solution containing 0.31 g (0.90 mmol) of tert-butyl (3-(5-phenyl-1H-pyrazole-3-carboxamido)propyl)carbamate, 5 ml of DCM, and 1.5 mL of TFA was allowed to stir at rt for 3 h. The solvents were removed under reduced pressure to give 0.31 g (99%) of 5-phenyl-N-(3-((pyridiniii) Preparation of N-(3-((2-hydroxybenzyl)amino)propyl)-5-phenyl-1H-pyrazole-3-carboxamide (Compound 21)

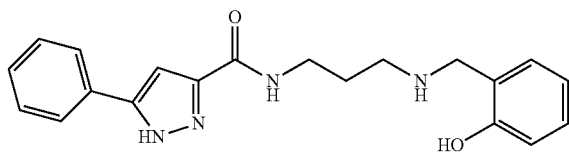 [SMILES: O=C(NCCCNCc1ccccc1O)c1cc(-c2ccccc2)[nH]n1]

According to General Procedure B, N-(3-((2-hydroxybenzyl)amino)propyl)-5-phenyl-1H-pyrazole-3-carboxamide was synthesized from 5-phenyl-N-(3-((pyridin-2-ylmethyl)amino)propyl)-1H-pyrazole-3-carboxamide. $^1$H NMR (400 MHz, CD$_3$OD): δ 7.71 (d, 2H, J=7.6 Hz), 7.46 (t, 2H, J=7.4 Hz), 7.38 (t, 1H, J=7.4 Hz), 7.32 (d, 1H, J=7.3 Hz), 7.28 (t, 1H, J=8.0 Hz), 7.11 (br s, 1H), 6.91-6.86 (m, 2H), 4.22 (s, 2H), 3.49 (t, 2H, J=6.3 Hz), 3.11 (t, 2H, J=7.2 Hz), 2.07-2.00 (m, 2H); LC/MS ret. time=0.902 min, m/z=351.30 [M+H]$^+$.

(17) Synthesis of 5-phenyl-N-(3-((pyridin-3-ylmethyl)amino)propyl)-1H-pyrazole-3-carboxamide (Compound 22)

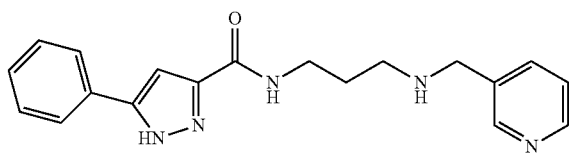 [SMILES: O=C(NCCCNCc1cccnc1)c1cc(-c2ccccc2)[nH]n1]

According to General Procedure B, 5-phenyl-N-(3-((pyridin-3-ylmethyl)amino)propyl)-1H-pyrazole-3-carboxamide was synthesized from 5-phenyl-N-(3-((pyridin-2-ylmethyl)amino)propyl)-1H-pyrazole-3-carboxamide. $^1$H NMR (400 MHz, CD$_3$OD): δ 8.33 (d, 1H, J=7.6 Hz), 7.84 (s, 1H), 7.72 (d, 2H, J=8.0), 7.48-7.44 (m, 3H), 7.41-7.37 (m, 2H), 4.40 (s, 2H), 3.53 (t, 2H, J=6.0 Hz), 3.19 (t, 2H, J=7.2 Hz), 2.06-2.02 (m, 2H); LC/MS ret. time=0.732 min, m/z=336.30 [M+H]$^+$.

(18) Synthesis of 5-phenyl-N-(3-((pyridin-2-ylmethyl)amino)propyl)-1H-pyrazole-3-carboxamide (Compound 23)

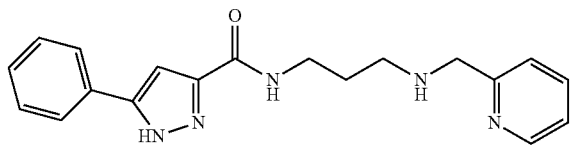

According to General Procedure B, 5-phenyl-N-(3-((pyridin-2-ylmethyl)amino)propyl)-1H-pyrazole-3-carboxamide was synthesized from 5-phenyl-N-(3-((pyridin-2-ylmethyl)amino)propyl)-1H-pyrazole-3-carboxamide. $^1$H NMR (400 MHz, CD$_3$OD): δ 8.62 (d, 1H, J=4.4 Hz), 7.85 (td, 1H, J=7.8, 1.7 Hz), 7.72 (d, 2H, J=7.5 Hz), 7.45 (t, 3H, J=7.4 Hz), 7.43-7.73 (m, 2H), 7.05 (s, 1H), 4.40 (s, 2H), 3.54 (t, 2H, J=6.4 Hz), 3.21 (t, 2H, J=7.4 Hz), 2.11-2.04 (m, 2H); LC/MS ret. time=0.824 min, m/z=336.30 [M+H]$^+$.

(19) Synthesis of N-(3-(((2-methyloxazol-5-yl)methyl)amino)propyl)-5-phenyl-(1H-pyrazole-3-carboxamide (Compound 24)

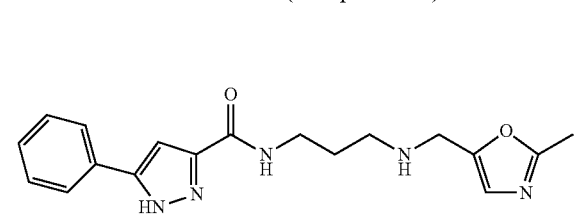

According to General Procedure B, N-(3-(((2-methyloxazol-5-yl)methyl)amino)propyl)-5-phenyl-1H-pyrazole-3-carboxamide was synthesized from 5-phenyl-N-(3-((pyridin-2-ylmethyl)amino)propyl)-1H-pyrazole-3-carboxamide. $^1$H NMR (400 MHz, CD$_3$OD): δ 7.93 (s, 1H), (7.71 (d, 2H, J=7.4 Hz), 7.45 (t, 2H, J=7.3 Hz), 7.38 (t, 1H, J=7.3 Hz), 7.05 (s, 1H), 4.15 (s, 2H), 3.52 (t, 2H, J=6.4 Hz), 3.15 (t, 2H, J=7.3 Hz), 2.42 (s, 3H), 2.05-1.98 (m, 2H); LC/MS ret. time=0.830 min, m/z=340.30 [M+H]$^+$.

(20) Synthesis of N-(3-(bis((2-methyloxazol-5-yl)methyl)amino)propyl)-5-phenyl-1H-pyrazole-3-carboxamide (Compound 25)

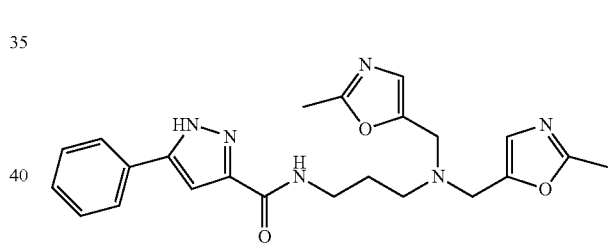

According to General Procedure B, N-(3-(bis((2-methyloxazol-5-yl)methyl)amino)propyl)-5-phenyl-1H-pyrazole-3-carboxamide was synthesized from 5-phenyl-N-(3-((pyridin-2-ylmethyl)amino)propyl)-1H-pyrazole-3-carboxamide. $^1$H NMR (400 MHz, CD$_3$OD): δ 8.05 (s, 2H), 7.72 (d, 2H, 7.72 Hz), 7.47 (t, 2H, J=7.8 Hz), 7.39 (t, 1H, J=7.3 Hz), 7.03) s, 1H), 4.33 (s, 4H), 3.50 (t, 2H, J=6.2 Hz), 3.29 (t, 2H, J=7.8 Hz, 2.41 (s, 6H), 2.24-2.13 (m, 2H); LC/MS ret. time=0.912 min, m/z=435.30 [M+H]$^+$.

(21) Synthesis of N-(3-(((1H-indol-3-yl)methyl)amino)propyl)-5-phenyl-1H-pyrazole-3-carboxamide (Compound 26)

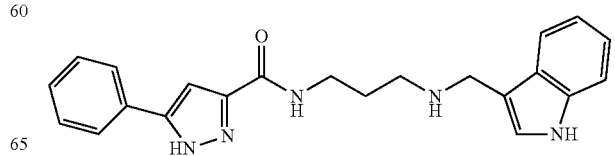

According to General Procedure B, N-(3-(((1H-indol-3-yl)methyl)amino)propyl)-5-phenyl-1H-pyrazole-3-carboxamide was synthesized from 5-phenyl-N-(3-((pyridin-2-ylmethyl)amino)propyl)-1H-pyrazole-3-carboxamide. $^1$H NMR (400 MHz, CD$_3$OD): δ 7.74 (d, 1H, J=7.8 Hz), 7.71 (d, 2H, J=7.4 Hz), 7.50 (s, 1H), 7.46 (t, 2H, J=7.4 Hz), 7.39 (t, 2H, J=6.9 Hz), 7.18 (t, 1H, J=7.0 Hz), 7.13 (t, 1H, J=7.8 Hz), 7.00 (s, 1H), 4.44 (s, 2H), 3.49 (t, 2H, J=6.4 Hz), 3.14 (t, 2H, J=7.3 Hz), 2.04-1.97 (m, 2H;) LC/MS ret. time=0.958 min, m/z=374.20 [M+H]$^+$.

(22) Synthesis of N-(3-(bis(3,4-dihydroxybenzyl)amino)propyl)-5-phenyl-(1H-pyrazole-3-carboxamide (Compound 27)

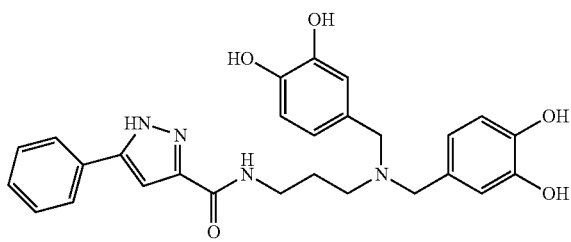 [SMILES: O=C(NCCCN(Cc1ccc(O)c(O)c1)Cc1ccc(O)c(O)c1)c1cc(-c2ccccc2)[nH]n1]

According to General Procedure B, N-(3-(bis(3,4-dihydroxybenzyl)amino)propyl)-5-phenyl-1H-pyrazole-3-carboxamide was synthesized from 5-phenyl-N-(3-((pyridin-2-ylmethyl)amino)propyl)-1H-pyrazole-3-carboxamide. LC/MS ret. time=0.819 min, m/z=367.30 [M+H]$^+$.

(23) Synthesis of N-(3-(((5-methoxypyridin-3-yl)methyl)amino)propyl)-5-phenyl-(1H-pyrazole-3-carboxamide (Compound 28)

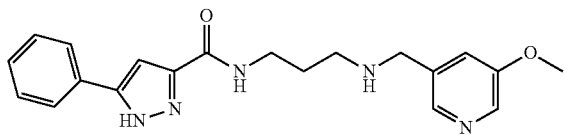 [SMILES: COc1cncc(CNCCCNC(=O)c2cc(-c3ccccc3)[nH]n2)c1]

According to General Procedure B, N-(3-(((5-methoxypyridin-3-yl)methyl)amino)propyl)-5-phenyl-1H-pyrazole-3-carboxamide was synthesized from 5-phenyl-N-(3-((pyridin-2-ylmethyl)amino)propyl)-1H-pyrazole-3-carboxamide. $^1$H NMR (400 MHz, CD$_3$OD): δ 8.15 (s, 1H), 8.10 (d, 1H, J=2.6 Hz), 7.71 (d, 2H, J=7.5 Hz), 7.48-7.42 (m, 3H), 7.37 (t, 1H, J=7.3 Hz), 7.01 (s, 1H), 3.85 (s, 3H), 3.80 (s, 2H), 3.46 (t, 2H, J=6.6 Hz), 2.71 (t, 2H, J=6.9 Hz), 1.88-1.81 (m, 2H); LC/MS ret. time=0.763 min, m/z=366.30 [M+H]$^+$.

(24) Synthesis of N-(3-(bis((5-methoxypyridin-3-yl)methyl)amino)propyl)-5-phenyl-1H-pyrazole-3-carboxamide (Compound 29)

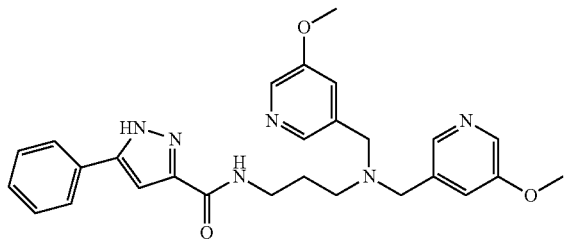 [SMILES: COc1cncc(CN(CCCNC(=O)c2cc(-c3ccccc3)[nH]n2)Cc2cncc(OC)c2)c1]

According to General Procedure B, N-(3-(bis((5-methoxypyridin-3-yl)methyl)amino)propyl)-5-phenyl-1H-pyrazole-3-carboxamide was synthesized from 5-phenyl-N-(3-((pyridin-2-ylmethyl)amino)propyl)-1H-pyrazole-3-carboxamide. $^1$H NMR (400 MHz, CD$_3$OD): δ 8.42 (s, 2H), 8.35 (s, 2H), 7.98 (s, 2H), 7.72 (d, 2H, J=7.5 Hz), 7.47 (t, 2H, J=7.4 Hz), 7.39 (t, 1H, J=7.3 Hz), 6.98 (s, 1H), 4.03 (s, 2H), 3.96 (s, 6H), 3.43 (t, 2H, J=6.5 Hz), 2.81 (t, 2H, J=6.8 Hz), 2.00-1.94 (m, 2H); LC/MS ret. time=0.842 min, m/z=487.30 [M+H]$^+$.

(25) Synthesis of N-(3-(((1H-pyrrolo[2,3-b]pyridin-3-yl)methyl)amino)propyl)-5-phenyl-1H-pyrazole-3-carboxamide (Compound 30)

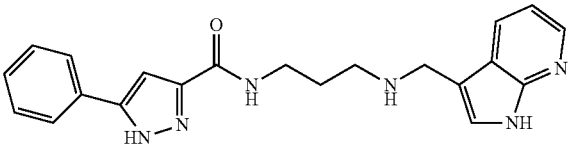 [SMILES: O=C(NCCCNCc1c[nH]c2ncccc12)c1cc(-c2ccccc2)[nH]n1]

According to General Procedure B, N-(3-(((1H-pyrrolo[2,3-b]pyridin-3-yl)methyl)amino)propyl)-5-phenyl-1H-pyrazole-3-carboxamide was synthesized from 5-phenyl-N-(3-((pyridin-2-ylmethyl)amino)propyl)-1H-pyrazole-3-carboxamide. $^1$H NMR (400 MHz, CD$_3$OD): δ 8.16-8.11 (m, 2H), 7.70 (d, 2H, J=7.4 Hz), 7.44 (t, 2H, J=7.4 Hz), 7.39-7.34 (m, 2H), 7.08 (dd, 1H, J=7.8, 4.9 Hz), 6.99 (s, 1H), 3.95 (s, 2H), 3.45 (t, 2H, J=6.6 Hz), 2.76 (t, 2H, J=8.8 Hz), 1.89-1.82 (m, 2H); LC/MS ret. time=0.761 min, m/z=375.30 [M+H]$^+$.

(26) Synthesis of N-(3-(((3-methylisoxazol-5-yl)methyl)amino)propyl)-5-phenyl-(1H-pyrazole-3-carboxamide (Compound 31)

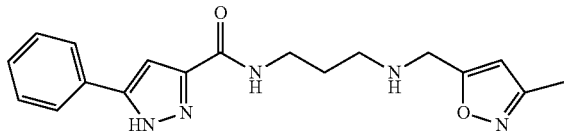 [SMILES: Cc1cc(CNCCCNC(=O)c2cc(-c3ccccc3)[nH]n2)on1]

According to General Procedure B, N-(3-(((3-methylisoxazol-5-yl)methyl)amino)propyl)-5-phenyl-1H-pyrazole-3-carboxamide was synthesized from 5-phenyl-N-(3-((pyridin-2-ylmethyl)amino)propyl)-1H-pyrazole-3-carboxamide. $^1$H NMR (400 MHz, CD$_3$OD): δ 7.71 (d, 2H, J=7.6 Hz), 7.46 (t, 2H, J=7.4 Hz), 7.38 (t, 1H, J=7.4 Hz), 7.05 (s, 1H), 6.30 (s, 1H), 4.33 (s, 2H), 3.52 (t, 2H, J=6.4 Hz), 3.19 (t, 2H, J=7.4 Hz), 2.45 (s, 3H), 2.07-2.00 (m, 2H); LC/MS ret. time=0.855 min, m/z=340.30 [M+H]$^+$.

(27) Synthesis of N-(3-(bis((3-methylisoxazol-5-yl)methyl)amino)propyl)-5-phenyl-1H-pyrazole-3-carboxamide (Compound 32)

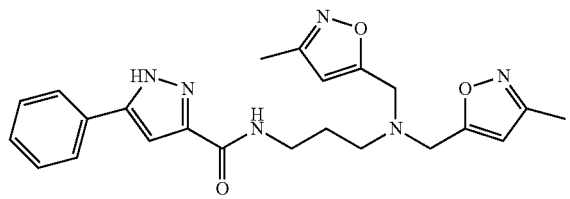 [SMILES: Cc1cc(CN(CCCNC(=O)c2cc(-c3ccccc3)[nH]n2)Cc2cc(C)no2)on1]

According to General Procedure B, N-(3-(bis((3-methylisoxazol-5-yl)methyl)amino)propyl)-5-phenyl-1H-pyrazole-3-carboxamide was synthesized from 5-phenyl-N-(3-((pyridin-2-ylmethyl)amino)propyl)-1H-pyrazole-3-carboxamide. LC/MS ret. time=0.951 min, m/z=435.3 [M+H]$^+$.

(28) Synthesis of N-(3-((2,4-dihydroxybenzyl)amino)propyl)-5-phenyl-(1H-pyrazole-3-carboxamide (Compound 33)

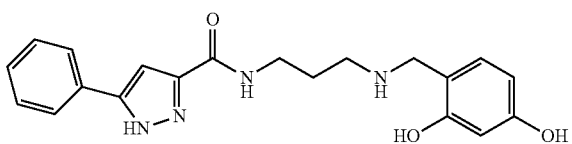 [SMILES: O=C(NCCCNCc1ccc(O)cc1O)c1cc(-c2ccccc2)[nH]n1]

According to General Procedure B, N-(3-((2,4-dihydroxybenzyl)amino)propyl)-5-phenyl-1H-pyrazole-3-carboxamide was synthesized from 5-phenyl-N-(3-((pyridin-2-ylmethyl)amino)propyl)-1H-pyrazole-3-carboxamide. LC/MS ret. time=0.768 min, m/z=366.30 [M+H]$^+$.

(29) Synthesis of N-(3-(((1-acetyl-1H-indol-3-yl)methyl)amino)propyl)-5-phenyl-(1H-pyrazole-3-carboxamide (Compound 34)

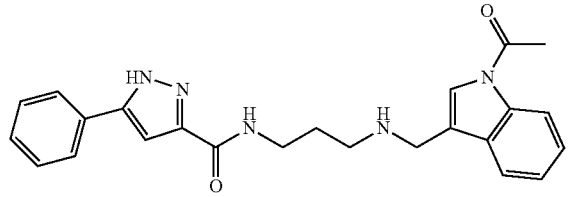 [SMILES: CC(=O)n1cc(CNCCCNC(=O)c2cc(-c3ccccc3)[nH]n2)c2ccccc21]

According to General Procedure B, N-(3-(((1-acetyl-1H-indol-3-yl)methyl)amino)propyl)-5-phenyl-1H-pyrazole-3-carboxamide was synthesized from 5-phenyl-N-(3-((pyridin-2-ylmethyl)amino)propyl)-1H-pyrazole-3-carboxamide. LC/MS ret. time=0.978 min, m/z=416.20 [M+H]$^+$.

(30) Synthesis of N-(3-((isoxazol-4-ylmethyl)amino)propyl)-5-phenyl-(1H-pyrazole-3-carboxamide (Compound 35)

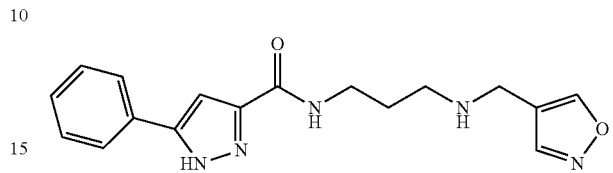

According to General Procedure B, N-(3-((isoxazol-4-ylmethyl)amino)propyl)-5-phenyl-1H-pyrazole-3-carboxamide was synthesized from 5-phenyl-N-(3-((pyridin-2-ylmethyl)amino)propyl)-1H-pyrazole-3-carboxamide. LC/MS ret. time=0.786 min, m/z=326.20 [M+H]$^+$.

(31) Synthesis of N-(3-(bis(isoxazol-4-ylmethyl)amino)propyl)-5-phenyl-1H-pyrazole-3-carboxamide (Compound 36)

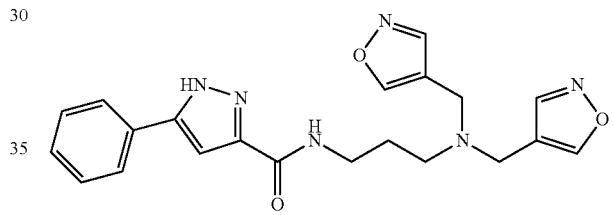

According to General Procedure B, N-(3-(bis(isoxazol-4-ylmethyl)amino)propyl)-5-phenyl-1H-pyrazole-3-carboxamide was synthesized from 5-phenyl-N-(3-((pyridin-2-ylmethyl)amino)propyl)-1H-pyrazole-3-carboxamide. LC/MS ret. time=840 min, m/z=407.20 [M+H]$^+$.

c. Synthesis of N-(3-((2-morpholinopyrimidin-4-yl)amino)propyl)-5-phenylisoxazole-3-carboxamide (Compound 18)

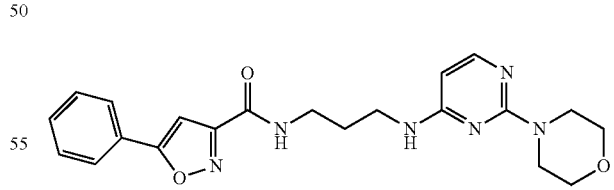

A mixture containing 50 mg (0.140 mmol) of N-(3-((2-chloropyrimidin-4-yl)amino)propyl)-5-phenylisoxazole-3-carboxamide, 24 μL (0.28 mmol) of morpholine, and 5 mL of isopropanol was heated at reflux overnight. The solvents were removed under reduced pressure and the residue was submitted to HPLC purification to give 40 mg (80%) of N-(3-(2-morpholinopyrimidin-4-yl)amino)propyl)-5-phenylisoxazole-3-carboxamide as a clear oily solid. LC/MS ret. time=0.996 min, m/z=409.0 [M+H]$^+$.

d. Synthesis of N-(3-((4-azidopyrimidin-2-yl)amino)propyl)-5-phenyl-1H-pyrazole-3-carboxamide (Compound 39)

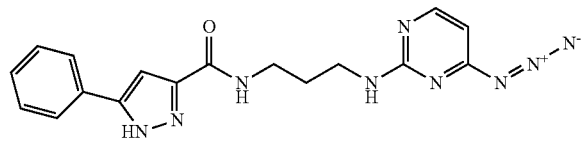 [SMILES: [NH-][NH+]=Nc1ccnc(NCCCNC(=O)c2cc(-c3ccccc3)[nH]n2)n1]

A reaction mixture containing 22 mg (0.061 mmol)N-(3-(4-chloropyrimidin-2-yl)amino)propyl)-5-phenyl-1H-pyrazole-3-carboxamide, 12 mg (0.184 mmol) of sodium azide, and 5 mL of EtOH was heated at reflux overnight. The solvents were removed under reduced pressure and the residue was subjected to HPLC purification to give 6 mg (27%) of N-(3-(4-azidopyrimidin-2-yl)amino)propyl)-5-phenyl-1H-pyrazole-3-carboxamide. LC/MS ret. time=0.963 min, m/z=364.30 [M+H]$^+$.

2. Biology Experimental Methods

SW620 and H520 cells ($5 \times 10^4$/100 µL) were seeded in a 96-well plate prior to treatment. Cells were treated with 10 µM concentration of synthesized compound in quadruplicate for 24 hours in RPMI 1640 supplemented medium and 100 µg/mL penicillin-streptomycin. The cells were then fixed with 100% methanol for 20 minutes at 4° C. The wells were then washed 2 times with PBS, permeabilized in 2% bovine serum albumin (BSA) and 0.2% TritonX-100 in PBS for 30 minutes at room temperature with gentle agitation, and blocked in LI-COR blocking buffer for 30 minutes at room temperature with gentle agitation. The cells were then incubated with the following primary antibodies: anti-E-Cadherin (1:500) and anti-α-Tubulin (1:1000) diluted in blocking buffer (1:1 dilution in PBS) for 2 hours at room temperature with gentle agitation. The cells were washed 4 times in PBS-T for 5 minutes each, and then incubated with the following secondary antibodies conjugated to a fluorescent entity: IRDye 800-conjugated goat anti-rabbit IgG (1:1000) and IRDye-700-conjugated goat anti-mouse IgG (1:2000) in blocking buffer (1:1 dilution in PBS) with gentle agitation for 1 h at room temperature. The cells were washed 4 times in PBS-T for 5 minutes each followed by a single wash with PBS. All liquid was removed from the wells and the plates were visualized and analyzed on the Odyssey IR imaging system (LI-COR Biosciences).

The assay was further optimized in the following manner. The cells were washed 2 times with PBS, fixed in 100% methanol at room temperature for 15 minutes, and again washed 2 times with PBS. The cells were then incubated with the following primary antibodies: anti-E-Cadherin (1:200) and anti-α-Tubulin (1:2000) diluted in ice cold 2% bovine serum albumin (BSA) and 0.2% TritonX-100 in PBS for 1 hour at room temperature with gentle agitation. The cells were washed 2 times in PBS and then incubated with the following secondary antibodies conjugated to a fluorescent entity: Licor 800-conjugated goat anti-rabbit IgG (1:2000) and IRDye-700-conjugated goat anti-mouse IgG (1:2000) in ice cold 2% BSA and 0.2% TritonX-100 in PBS with gentle agitation for 45 minutes at room temperature. The wells were washed 2 times in PBS, dried, and analyzed as previously mentioned.

3. Characterization of Exemplary Compounds

The compounds below in Table 1 were synthesized with methods identical or analogous to those described herein. The requisite starting materials were commercially available, described in the literature, or readily synthesized by one skilled in the art of organic synthesis. The mass spectrometry data were obtained using the general LC-MS methods as described above. LC-MS [M+H]$^+$ means the protonated mass of the free base of the compound.

TABLE I

| No. | Compound | LC-MS [M + H]$^+$ |
|---|---|---|
| 1 |  | 348.20 |
| 2 |  | 375.30 |
| 3 |  | 326.20 |

TABLE I-continued

| No. | Compound | LC-MS [M + H]+ |
|-----|----------|----------------|
| 4 | 5-phenyl-N-(3-((2-methyloxazol-5-yl)methylamino)propyl)isoxazole-3-carboxamide | 341.2 |
| 5 | 5-phenyl-N-(3-((pyridin-2-ylmethyl)amino)propyl)isoxazole-3-carboxamide | 337.20 |
| 6 | 5-phenyl-N-(3-(bis(pyridin-2-ylmethyl)amino)propyl)isoxazole-3-carboxamide | 428.20 |
| 7 | 5-phenyl-N-(3-(bis((2-methyloxazol-5-yl)methyl)amino)propyl)isoxazole-3-carboxamide | 436.30 |
| 8 | 5-phenyl-N-(3-((3,4-dihydroxybenzyl)amino)propyl)isoxazole-3-carboxamide | 368.20 |
| 9 | 5-phenyl-N-(3-(((5-methoxypyridin-3-yl)methyl)amino)propyl)isoxazole-3-carboxamide | 367.30 |
| 10 | 5-phenyl-N-(3-(((1H-pyrrolo[3,2-b]pyridin-3-yl)methyl)amino)propyl)isoxazole-3-carboxamide | 376.20 |
| 11 | 5-phenyl-N-(3-(((3-methylisoxazol-5-yl)methyl)amino)propyl)isoxazole-3-carboxamide | 341.20 |
| 12 | 5-phenyl-N-(3-((2,4-dihydroxybenzyl)amino)propyl)isoxazole-3-carboxamide | 368.20 |

TABLE I-continued

| No. | Compound | LC-MS [M + H]+ |
|---|---|---|
| 13 | | 417.30 |
| 14 | | 327.30 |
| 15 | | 408.30 |
| 16 | | 352.20 |
| 17 | | 365.20 |
| 18 | | 409.0 |
| 19 | | 353.0 |
| 20 | | 339.0 |

TABLE I-continued

| No. | Compound | LC-MS [M + H]+ |
|---|---|---|
| 21 | 5-phenyl-1H-pyrazole-3-carboxamide-N-propyl-NH-CH2-(2-hydroxyphenyl) | 351.30 |
| 22 | 5-phenyl-1H-pyrazole-3-carboxamide-N-propyl-NH-CH2-(pyridin-3-yl) | 336.30 |
| 23 | 5-phenyl-1H-pyrazole-3-carboxamide-N-propyl-NH-CH2-(pyridin-2-yl) | 336.30 |
| 24 | 5-phenyl-1H-pyrazole-3-carboxamide-N-propyl-NH-CH2-(2-methyloxazol-5-yl) | 340.30 |
| 25 | 5-phenyl-1H-pyrazole-3-carboxamide-N-propyl-N(CH2-(2-methyloxazol-5-yl))2 | 435.30 |
| 26 | 5-phenyl-1H-pyrazole-3-carboxamide-N-propyl-NH-CH2-(1H-indol-3-yl) | 374.20 |
| 27 | 5-phenyl-1H-pyrazole-3-carboxamide-N-propyl-N(CH2-(3,4-dihydroxyphenyl))2 | 367.30 |
| 28 | 5-phenyl-1H-pyrazole-3-carboxamide-N-propyl-NH-CH2-(5-methoxypyridin-3-yl) | 366.30 |

TABLE I-continued

| No. | Compound | LC-MS [M + H]+ |
|---|---|---|
| 29 | | 487.30 |
| 30 | | 375.30 |
| 31 | | 340.30 |
| 32 | | 435.3 |
| 33 | | 366.30 |
| 34 | | 416.20 |
| 35 | | 326.20 |
| 36 | | 407.20 |

TABLE I-continued

| No. | Compound | LC-MS [M + H]+ |
|---|---|---|
| 37 | | 364.20 |
| 38 | | 357.20 |
| 39 | | 364.30 |

4. Activity of N-(3-(arylamino)alkyl)-5-arylisoxazole-3-carboxamide Analogs in a Cell-Based Assay N-(3-(Arylamino)alkyl)-5-arylisoxazole-3-carboxamide analogs were synthesized as described above. Changes in expression level of E-cadherin in response to 10 μM compound in SW620 cells was determined in the cell-based functional assay as described above, and the data are shown in Table II. The compound number corresponds to the compound numbers used in Table I.

TABLE II

| Compound No. | Fold Change SW620 ICW | Compound No. | Fold Change SW620 ICW |
|---|---|---|---|
| 1 | 0.63 | 9 | 0.89 |
| 2 | 0.68 | 10 | 0.91 |
| 3 | 0.70 | 11 | 0.90 |
| 4 | 0.71 | 12 | 0.91 |
| 5 | 0.71 | 13 | 0.91 |
| 23 | 1.44 | 14 | 0.94 |
| 24 | 1.50 | 15 | 0.95 |
| 25 | 1.54 | 16 | 0.98 |
| 26 | 1.64 | 17 | 1.07 |
| 27 | 1.67 | 21 | 1.14 |
| 6 | 0.82 | 22 | 1.16 |
| 7 | 0.83 | 28 | 1.80 |
| 8 | 0.84 | 29 | 2.09 |
| 30 | 2.33 | 35 | 3.59 |
| 31 | 2.52 | 36 | 5.77 |
| 32 | 3.06 | 37 | 6.09 |
| 33 | 3.40 | 38 | 7.36 |
| 34 | 3.58 | 39 | 15.89 |

$EC_{50}$ of inducement of E-cadherin expression in SW620 cells was determined in the cell-based functional assay as described above, and the data are shown in Table III. The compound number corresponds to the compound numbers used in Table I.

TABLE III

| Compound No. | $EC_{50}$ SW620 ICW |
|---|---|
| 36 | 11.99 |
| 37 | 15.02 |
| 38 | 22.91 |
| 39 | 5.32 |

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

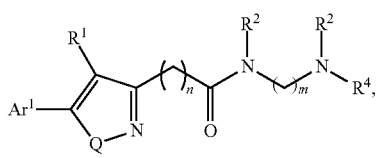

wherein m is an integer selected from 3 and 4;
wherein n is an integer selected from 0 and 1;
wherein Q is selected from $NR^5$, O, and S;
  wherein $R^5$, when present, is selected from hydrogen and C1-C4 alkyl;
wherein each of $R^1$ and $R^2$ is independently selected from hydrogen and C1-C4 alkyl;
wherein $R^3$ is selected from hydrogen and $(CHR^6)_p Ar^2$;
  wherein p, when present, is an integer selected from 0 and 1;

wherein $R^6$, when present, is selected from hydrogen and C1-C4 alkyl;

wherein $Ar^2$, when present, is selected from aryl and heteroaryl, and $Ar^2$ is substituted with 0, 1, 2, or 3 groups independently selected from halogen, —OH, —CN, —$N_3$, —$NH_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino;

wherein $R^4$ is selected from $CH_2Ar^3$ and $Ar^4$;

wherein $Ar^3$, when present, is selected from aryl and heteroaryl, and $Ar^3$ is substituted with 0, 1, 2, or 3 groups independently selected from halogen, —OH, —CN, —$N_3$, —$NH_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino, provided that when $R^2$ is hydrogen then $Ar^3$, when present, cannot be a structure selected from:

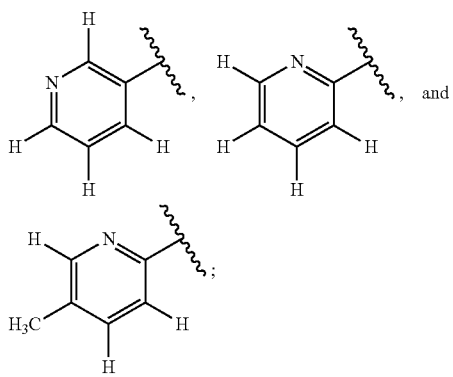

wherein $Ar^4$, when present, is selected from aryl and heteroaryl, and $Ar^4$ is substituted with 0, 1, 2, or 3 groups independently selected from halogen, —OH, —CN, —$N_3$, —$NH_2$, —C(O)(C1-C4 alkyl), C1-C4 alkyl, C1-C4 alkoxy, C1-C4 monohaloalkyl, C1-C4 polyhaloalkyl, C1-C4 alkylamino, and C1-C4 dialkylamino, provided that when $R^2$ is hydrogen then $Ar^4$, when present, cannot be a structure selected from:

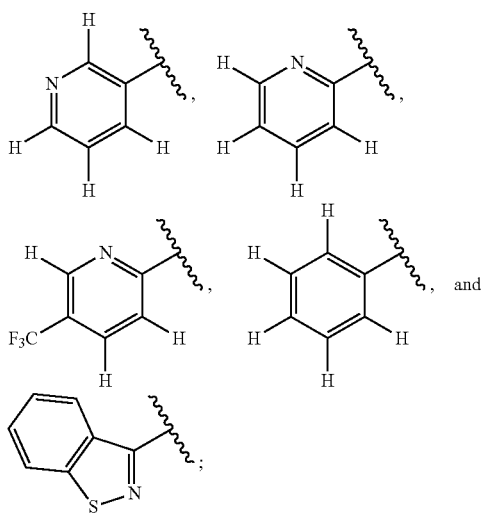

and wherein $Ar^1$, when present, is selected from aryl and heteroaryl, and wherein $Ar^1$, when present, is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino, or a pharmaceutically acceptable salt thereof.

2. The compound of claim 1, wherein $R^3$ is $(CHR^6)_pAr^2$.

3. The compound of claim 1, wherein $R^3$ is $(CH_2)_pAr^2$.

4. The compound of claim 1, wherein $R^4$ is $CH_2Ar^3$.

5. The compound of claim 1, wherein $R^4$ is $Ar^4$.

6. The compound of claim 1, wherein $Ar^1$ is aryl, and $Ar^1$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino.

7. The compound of claim 1, wherein $Ar^1$ is phenyl, and $Ar^1$ is substituted with 0, 1, 2, or 3 groups independently selected from halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino.

8. The compound of claim 1, wherein $R^2$ is hydrogen and $Ar^3$ is not substituted or unsubstituted pyridinyl.

9. The compound of claim 1, wherein $R^2$ is hydrogen and $Ar^4$ is not substituted or unsubstituted pyridinyl, phenyl, or benzo[d]isothiazole.

10. The compound of claim 1, wherein the compound has a structure represented by a formula:

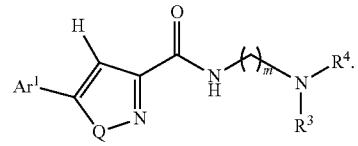

11. The compound of claim 1, wherein the compound has a structure represented by a formula:

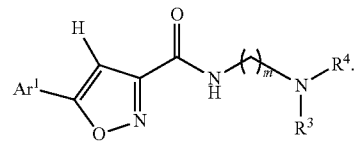

12. The compound of claim 1, wherein the compound has a structure represented by a formula:

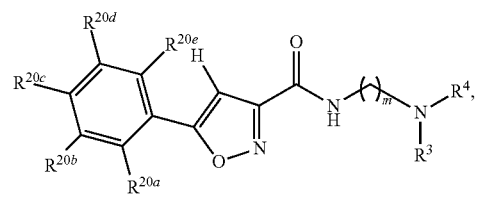

wherein each of $R^{20a}$, $R^{20b}$, $R^{20c}$, $R^{20d}$, and $R^{20e}$ are independently selected from hydrogen, halogen, —OH, —CN, —$N_3$, —$NH_2$, C1-C4 alkyl, C1-C4 alkoxy, C1-C4 monohaloalkyl, C1-C4 polyhaloalkyl, C1-C4 alkylamino, and C1-C4 dialkylamino, provided that at least two of $R^{20a}$, $R^{20b}$, $R^{20c}$, $R^{20d}$, and $R^{20e}$ are hydrogen.

13. The compound of claim 1, wherein the compound has a structure represented by a formula:

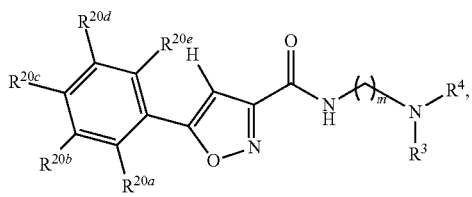

wherein each of $R^{20b}$, $R^{20c}$, and $R^{20d}$ are hydrogen and each of $R^{20a}$ and $R^{20e}$ are independently selected from hydrogen, halogen, —OH, —CN, —N$_3$, —NH$_2$, C1-C4 alkyl, C1-C4 alkoxy, C1-C4 monohaloalkyl, C1-C4 polyhaloalkyl, C1-C4 alkylamino, and C1-C4 dialkylamino.

14. The compound of claim 1, wherein the compound has a structure represented by a formula:

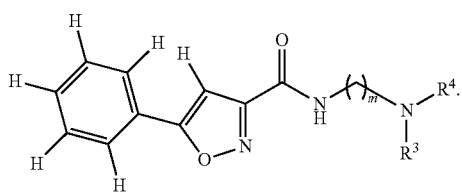

15. A compound having a structure selected from:

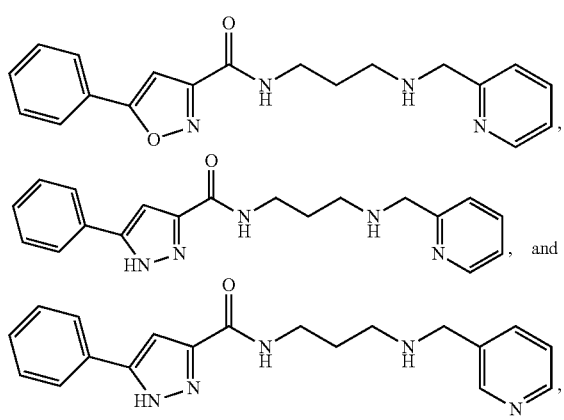

or a pharmaceutically acceptable salt thereof.

16. The compound of claim 1, wherein the compound has a structure represented by a formula:

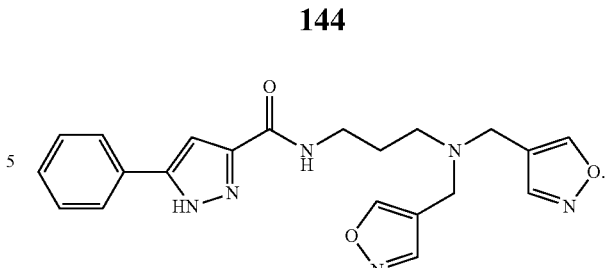

17. The compound of claim 1, wherein the compound has a structure represented by a formula:

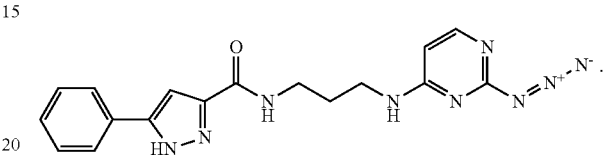

18. the compound of claim 1, wherein the compound has a structure represented by a formula:

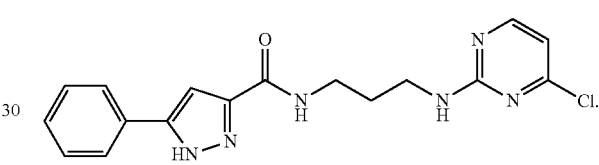

19. The compound of claim 1, wherein the compound has a structure represented by a formula:

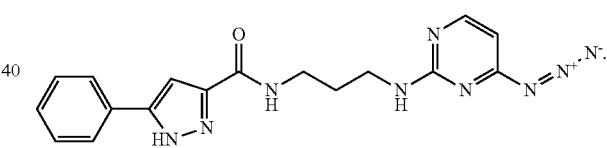

20. The compound of claim 1, wherein the compound has a structure represented by a formula:

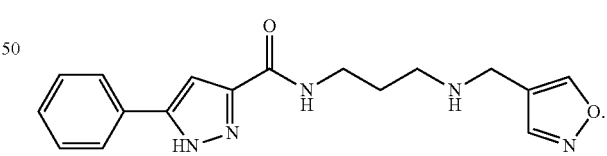

* * * * *

UNITED STATES PATENT AND TRADEMARK OFFICE
CERTIFICATE OF CORRECTION

PATENT NO. : 9,505,729 B2
APPLICATION NO. : 14/828286
DATED : November 29, 2016
INVENTOR(S) : Craig W. Lindsley et al.

It is certified that error appears in the above-identified patent and that said Letters Patent is hereby corrected as shown below:

In the Claims

In Column 140, Line 50, compound:

" 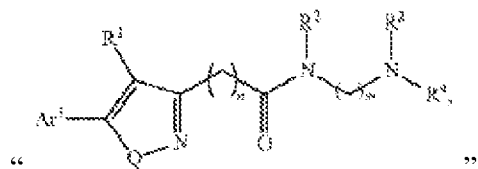 "

Should be:

-- 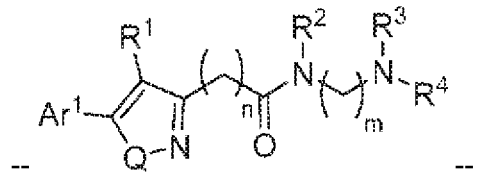 --

Signed and Sealed this
Eighteenth Day of April, 2017

Michelle K. Lee
*Director of the United States Patent and Trademark Office*